United States Patent
Wang et al.

(10) Patent No.: US 11,220,510 B2
(45) Date of Patent: Jan. 11, 2022

(54) PYRROLE TRICYCLIC COMPOUNDS AS A2A / A2B INHIBITORS

(71) Applicant: Incyte Corporation, Wilmington, DE (US)

(72) Inventors: Xiaozhao Wang, Mt. Laurel, NJ (US); Peter Niels Carlsen, Claymont, DE (US); Chunhong He, Boothwyn, PA (US); Taisheng Huang, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/377,793

(22) Filed: Apr. 8, 2019

(65) Prior Publication Data

US 2019/0337957 A1 Nov. 7, 2019

Related U.S. Application Data

(60) Provisional application No. 62/654,950, filed on Apr. 9, 2018.

(51) Int. Cl.
*C07D 487/14* (2006.01)

(52) U.S. Cl.
CPC .................. *C07D 487/14* (2013.01)

(58) Field of Classification Search
CPC ...... C07D 487/14; A61P 35/00; A61K 31/519
USPC .......................................... 544/251; 514/257
See application file for complete search history.

(56) References Cited

U.S. PATENT DOCUMENTS

| 5,521,184 A | 5/1996 | Zimmermann |
| 2006/0122392 A1 | 6/2006 | Nakai et al. |
| 2007/0225286 A1 | 9/2007 | Ren et al. |
| 2012/0035172 A1 | 2/2012 | Zheng et al. |
| 2013/0231307 A1 | 9/2013 | Agrofoglio et al. |
| 2015/0280137 A1 | 10/2015 | Bilyk et al. |
| 2018/0219159 A1 | 8/2018 | Yersin et al. |
| 2018/0312535 A1 | 11/2018 | Butora et al. |

FOREIGN PATENT DOCUMENTS

| WO | WO 00/009495 | 2/2000 |
| WO | WO 00/053595 | 9/2000 |
| WO | WO 01/014402 | 3/2001 |
| WO | WO 01/064655 | 9/2001 |
| WO | WO 02/000196 | 1/2002 |
| WO | WO 03/024967 | 3/2003 |
| WO | WO 03/037347 | 5/2003 |
| WO | WO 03/099771 | 12/2003 |
| WO | WO 2004/005281 | 1/2004 |
| WO | WO 2004/046120 | 6/2004 |
| WO | WO 2004/056786 | 7/2004 |
| WO | WO 2004/080980 | 9/2004 |
| WO | WO 2005/028444 | 3/2005 |
| WO | WO 2011/031740 | 3/2011 |
| WO | WO 2017/066789 | 4/2017 |
| WO | WO 2017/066791 | 4/2017 |
| WO | WO 2017/066793 | 4/2017 |
| WO | WO 2017/066797 | 4/2017 |
| WO | WO 2020/052631 | 3/2020 |
| WO | WO 2020/106560 | 5/2020 |

OTHER PUBLICATIONS

Atzrodt et al. Angew. Chem. Int. Ed. 2007, 46, 7744-7765.*
Cecil Textbook of Medicine, edited by Bennet, J.C., and Plum F., 20th edition,vol. 1, 1004-1010, 1996.*
Freshney et al Culture of Animal Cells, A Manual of Basic Technique, Alan R. Liss, Inc., 1983, New York, p. 4.*
Dermer et al., Bio/Technology, 1994, 12:320.*
PubChem Search pccompound 1-13,Create Date Dec. 1, 2008 & Nov. 30, 2012.*
Cheong et al. International Journal of Medicinal Chemistry, vol. 2011, p. 1-15. (Year: 2011).*
Effendi et al. Cells 2020, 9, 785, p. 1-36 (Year: 2020).*
Allard et al., "Immunosuppressive activities of adenosine in cancer," Current Opinion in Pharmacology, Aug. 2016, 29:7-16.
Antonioli et al., "Immunity, inflammation and cancer: a leading role for adenosine," Nature Reviews Cancer, 2013, 13(12):842-857.
Atzrodt et al., "The Renaissance ofH/D Exchange," Angew Chem Int Ed., Oct. 4, 2007, pp. 7744-7765.
Baraldi et al., "Adenosine receptor antagonists: translating medicinal chemistry and pharmacology into clinical utility," Chem Rev., Jan. 2008, 108(1):238-263.
Beavis et al., "Blockade of A2A receptors potently suppresses the metastasis of CD73+ tumors," Proc Natl Acad Sci USA., Sep. 3, 2013, 110(36):14711-14716.
Berge et al., "Pharmaceutical Salts", Journal of Pharmaceutical Science, 66:1-19 (1977).
Borrmann et al.,"1-alkyl-8-(piperazine-1-sulfonyl)phenylxanthines: development and characterization of adenosine A2B receptor antagonists and a new radioligand with subnanomolar affinity and subtype specificity," J Med. Chem., Jul. 9, 2009, 52(13):3994-4006.

(Continued)

*Primary Examiner* — Emily A Bernhardt
(74) *Attorney, Agent, or Firm* — Fish & Richardson P.C.

(57) ABSTRACT

This application relates to compounds of Formula (I):

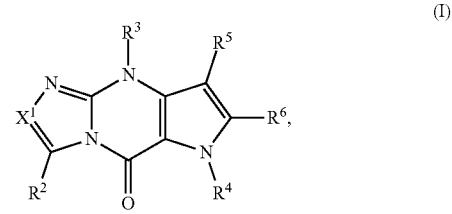

(I)

or pharmaceutically acceptable salts or stereoisomers thereof, which modulate the activity of adenosine receptors, such as subtypes A2A and A2B receptors, and are useful in the treatment of diseases related to the activity of adenosine receptors including, for example, cancer, inflammatory diseases, cardiovascular diseases, and neurodegenerative diseases.

2 Claims, No Drawings

(56) References Cited

OTHER PUBLICATIONS

Blom et al., "Preparative LC-MS Purification: Improved Compound Specific Method Optimization," J Cambi Chem., Nov.-Dec. 2004, 6(6):874-883.
Blom et al., "Two-Pump at Column Dilution Configuration for Preparative LC-MS," J Com Chem., Jul.-Aug. 2002, 4(4):295-301.
Blom et al., "Optimizing Preparative LC-MS Configurations and Methods for Parallel Synthesis Purification," J Cambi Chem., Jul. 29, 2003, 5(5):670-683.
Carlsson et al., "Structure-based discovery of A2A adenosine receptor ligands," J Med Chem., May 13, 2010, 53(9):3748-3755.
Cekic et al., "Adenosine A2B receptor blockade slows growth of bladder and breast tumors," J Immunol., Jan. 1, 2012, 188(1):198-205.
"Corvus Pharmaceuticals Announces Interim Results from Ongoing Phase 1/1b Study Demonstrating Safety and Clinical Activity of Lead Checkpoint Inhibitor CPI-444 in Patients with Advanced Cancers," https://globenewswire.com/news-release/2017/04/04/954192/0/en/Corvus-Pharmaceuticals-Announces-Interim-Results-from-Ongoing-Phase-1-1b-Study-Demonstrating-Safety-and-Clinical-Activity-of-Lead-Checkpoint-Inhibitor-CPI-444-in-Patients-with-Adva.html.
Collins et al., "The novel adenosine A2A antagonist Lu AA47070 reverses the motor and motivational effects produced by dopamine D2 receptor blockade," Pharmacol Biochem Behav., Jan. 2012, 100(3):498-505.
Eisenstein et al., "The Many Faces of the A2b Adenosine Receptor in Cardiovascular and Metabolic Diseases," J Cell Physiol., Dec. 2015, 230(12):2891-2897.
Figler et al., "Links between insulin resistance, adenosine A2B receptors, and inflammatory markers in mice and humans," Diabetes, Feb. 2011, 60(2):669-679.
Hasko at al., "Shaping of monocyte and macrophage function by adenosine receptors," Pharmacol. Ther., Feb. 2007, 113(2):264-275.
Iannone et al., "Blockade of A2b Adenosine Receptor Reduces Tumor Growth and Immune Suppression Mediated by Myeloid-Derived Suppressor Cells in a Mouse Model of Melanoma," Neoplasia, Dec. 2013, 15(12):1400-1410.
Iannone et al., "Adenosine limits the therapeutic effectiveness of anti-CTLA4 mAb in a mouse melanoma model," Am. J Cancer Res., Mar. 1, 2014, 4(2):172-181.
Kerekes et al., "Aurora kinase inhibitors based on the imidazo[1,2-a]pyrazine core: fluorine and deuterium incorporation improve oral absorption and exposure," J Med Chem., Jan. 2011, 54(1):201-210.
Livingston et al., "Adenosine, inflammation and asthma—a review," Inflamm. Res., 2004, 53(5):171-178.
Matsumoto et al., "Alterations in vasoconstrictor responses to the endothelium-derived contracting factor uridine adenosine tetraphosphate are region specific in DOCA-salt hypertensive rats," Pharmacol. Res., Jan. 2012, 65(1):81-90.
Nakanishi et al., "Structure of the fluorescent Y base from yeast phenylalanine transfer ribonucleic acid," J Am Chem Soc., Dec. 30, 1970, 92(26):7617-7619.
Remington's Pharmaceutical Sciences, 17th ed., Mack Publishing Company, Easton, Pa., 1985, p. 1418.
Ryzhov et al., "Host A(2B) adenosine receptors promote carcinoma growth," Neoplasia Sep. 2008, 10(9):987-995.
Sachdeva et al., "Adenosine and its receptors as therapeutic targets: An overview," Saudi Pharmaceutical Journal, Jul. 2013, 21(3):245-253.
Sattin et al., "The effect of adenosine and adenine nucleotides on the cyclic adenosine 3', 5'-phosphate content of guinea pig cerebral cortex slices," 1970, Mol Pharmacol., 6(1):13-23.
Tautenhahn et al., "Purinergic modulation of the excitatory synaptic input onto rat striatal neurons," Neuropharmacology, Mar. 2012, 62(4):1756-1766.
Xu et. al., "Design, synthesis and biological evaluation of deuterated nintedanib for improving pharmacokinetic properties," J. Label Compd. Radiopharm., Jun. 15, 2015, 58(7):308-312.
Hulikal, "Deuterium Labeled Compounds in Drug Discovery Process," 2010 [retrieved on Aug. 20, 2020], retrieved from URL <https://www.hwb.gov.in/sites/default/files/nuclear/L15.pdf>, 1 page (Abstract only).

\* cited by examiner

PYRROLE TRICYCLIC COMPOUNDS AS A2A / A2B INHIBITORS

TECHNICAL FIELD

The present invention provides pyrrole tricyclic compounds that modulate the activity of adenosine receptors, such as subtypes A2A and A2B, and are useful in the treatment of diseases related to the activity of adenosine receptors including, for example, cancer, inflammatory diseases, cardiovascular diseases and neurodegenerative diseases.

BACKGROUND

Adenosine is an extracellular signaling molecule that can modulate immune responses through many immune cell types. Adenosine was first recognized as a physiologic regulator of coronary vascular tone by Drury and Szent-Györgyu (Sachdeva, S. and Gupta, M. *Saudi Pharmaceutical Journal*, 2013, 21, 245-253), however it was not until 1970 that Sattin and Rall showed that adenosine regulates cell function via occupancy of specific receptors on the cell surface (Sattin, A., and Rall, T. W., 1970. Mol. Pharmacol. 6, 13-23; Hasko', G., at al., 2007, *Pharmacol. Ther.* 113, 264-275).

Adenosine plays a vital role in various other physiological functions. It is involved in the synthesis of nucleic acids, when linked to three phosphate groups; it forms ATP, the integral component of the cellular energy system. Adenosine can be generated by the enzymatic breakdown of extracellular ATP, or can be also released from injured neurons and glial cells by passing the damaged plasma membrane (Tautenhahn, M. et al. *Neuropharmacology*, 2012, 62, 1756-1766). Adenosine produces various pharmacological effects, both in periphery and in the central nervous system, through an action on specific receptors localized on cell membranes (Matsumoto, T. et al. Pharmacol. Res., 2012, 65, 81-90). Alternative pathways for extracellular adenosine generation have been described. These pathways include the production of adenosine from nicotinamide dinucleotide (NAD) instead of ATP by the concerted action of CD38, CD203a and CD73. CD73-independent production of adenosine can also occur by other phosphates such as alkaline phosphatase or prostate-specific phosphatase.

There are four known subtypes of adenosine receptor in humans including A1, A2A, A2B and A3 receptors. A1 and A2A are high affinity receptors, whereas A2B and A3 are low affinity receptors. Adenosine and its agonists can act via one or more of these receptors and can modulate the activity of adenylate cyclase, the enzyme responsible for increasing cyclic AMP (cAMP). The different receptors have differential stimulatory and inhibitory effects on this enzyme. Increased intracellular concentrations of cAMP can suppress the activity of immune and inflammatory cells (Livingston, M. et al., *Inflamm. Res.*, 2004, 53, 171-178).

The A2A adenosine receptor can signal in the periphery and the CNS, with agonists explored as anti-inflammatory drugs and antagonists explored for neurodegenerative diseases (Carlsson, J. et al., *J. Med. Chem.*, 2010, 53, 3748-3755). In most cell types the A2A subtype inhibits intracellular calcium levels whereas the A2B potentiates them. The A2A receptor generally appears to inhibit inflammatory response from immune cells (Borrmann, T. et al., *J. Med. Chem.*, 2009, 52(13), 3994-4006).

A2B receptors are highly expressed in the gastrointestinal tract, bladder, lung and on mast cells (Antonioli, L. et al., *Nature Reviews Cancer*, 2013, 13, 842-857). The A2B receptor, although structurally closely related to the A2A receptor and able to activate adenylate cyclase, is functionally different. It has been postulated that this subtype may utilize signal transduction systems other than adenylate cyclase (Livingston, M. et al., *Inflamm. Res.*, 2004, 53, 171-178). Among all the adenosine receptors, the A2B adenosine receptor is a low affinity receptor that is thought to remain silent under physiological conditions and to be activated in consequence of increased extracellular adenosine levels (Ryzhov, S. et al. *Neoplasia*, 2008, 10, 987-995). Activation of A2B adenosine receptor can stimulate adenylate cyclase and phospholipase C through activation of Gs and Gq proteins, respectively. Coupling to mitogen activated protein kinases has also been described (Borrmann, T. et al., *J. Med. Chem.*, 2009, 52(13), 3994-4006).

In the immune system, engagement of adenosine signaling can be a critical regulatory mechanism that protects tissues against excessive immune reactions. Adenosine can negatively modulate immune responses through many immune cell types, including T-cells, natural-killer cells, macrophages, dendritic cells, mast cells and myeloid-derived suppressor cells (Allard, B. et al. *Current Opinion in Pharmacology*, 2016, 29, 7-16).

In tumors, this pathway is hijacked by tumor micro-environments and sabotages the antitumor capacity of immune system, promoting cancer progression. In the tumor micro-environment, adenosine was mainly generated from extracellular ATP by CD39 and CD73. Multiple cell types can generate adenosine by expressing CD39 and CD73. This is the case for tumor cells, T-effector cells, T-regulatory cells, tumor associated macrophages, myeloid derived suppressive cells (MDSCs), endothelial cells, cancer-associated fibroblast (CAFs) and mesenchymal stromal/stem cells (MSCs). Hypoxia, inflammation and other immune-suppressive signaling in tumor micro-environment can induce expression of CD39, CD73 and subsequent adenosine production. As a result, adenosine level in solid tumors is unusually high compared to normal physiological conditions.

A2A are mostly expressed on lymphoid-derived cells, including T-effector cells, T regulatory cells and nature killing cells. Blocking A2A receptor can prevent downstream immunosuppressive signals that temporarily inactivate T cells. A2B receptors are mainly expressed on monocyte-derived cells including dendritic cells, tumor-associated macrophages, myeloid derived suppressive cells (MDSCs), and mesenchymal stromal/stem cells (MSCs). Blocking A2B receptor in preclinical models can suppress tumor growth, block metastasis, and increase the presentation of tumor antigens.

In terms of safety profile of ADORA2A/ADORA2B (A2A/A2B) blockage, the A2A and A2B receptor knockout mice are all viable, showing no growth abnormalities and are fertile (Allard, B. et al. *Current Opinion in Pharmacology*, 2016, 29, 7-16). A2A KO mice displayed increased levels of pro-inflammatory cytokines only upon challenge with LPS and no evidence of inflammation at baseline (Antonioli, L. et al., *Nature Reviews Cancer*, 2013, 13, 842-857). A2B KO mice exhibited normal platelet, red blood, and white cell counts but increased inflammation at baseline (TNF-alpha, IL-6) in naive A2B KO mice (Antonioli, L. et al., *Nature Reviews Cancer*, 2013, 13, 842-857). Exaggerated production of TNF-alpha and IL-6 was detected following LPS treatment. A2B KO mice also exhibited increased vascular adhesion molecules that mediate inflammation as well leukocyte adhesion/rolling; enhanced mast-cell activation;

increased sensitivity to IgE-mediated anaphylaxis and increased vascular leakage and neutrophil influx under hypoxia (Antonioli, L. et al., *Nature Reviews Cancer,* 2013, 13, 842-857).

In summary, there is a need to develop new adenosine receptor selective ligands, such as for subtypes A2A and A2B, for the treatment of diseases such as cancer, inflammatory diseases, cardiovascular diseases and neurodegenerative diseases. This application is directed to this need and others.

SUMMARY

The present invention relates to, inter alia, compounds of Formula (I):

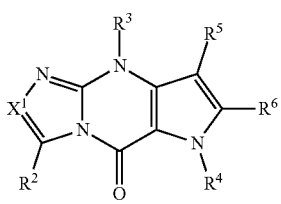

(I)

or pharmaceutically acceptable salts thereof, wherein constituent members are defined herein.

The present invention further provides pharmaceutical compositions comprising a compound of Formula (I), or a pharmaceutically acceptable salt thereof, and a pharmaceutically acceptable carrier.

The present invention further provides methods of inhibiting an activity of an adenosine receptor, comprising contacting the receptor with a compound of Formula (I), or a pharmaceutically acceptable salt thereof.

The present invention further provides methods of treating a disease or a disorder associated with abnormal expression of adenosine receptors, comprising administering to said patient a therapeutically effective amount of a compound of Formula (I), or a pharmaceutically acceptable salt thereof.

The present invention further provides a compound of Formula (I), or a pharmaceutically acceptable salt thereof, for use in any of the methods described herein.

The present invention further provides use of a compound of Formula (I), or a pharmaceutically acceptable salt thereof, for the preparation of a medicament for use in any of the methods described herein.

DETAILED DESCRIPTION

Compounds

The present application provides, inter alia, compounds of Formula (I):

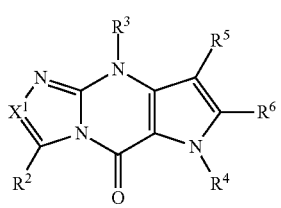

(I)

or a pharmaceutically acceptable salt thereof; wherein:

$X^1$ is N or $CR^1$;

$R^1$ is selected from H, D, halo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, CN, OH, and $NH_2$, wherein the $C_{1-6}$ alkyl is optionally substituted with OH, CN, and $NH_2$;

$R^2$ is selected from H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $OR^{a2}$, $OC(O)NR^{c2}R^{d2}$, $NHOR^{a2}$, $C(O)R^{b2}$, $C(O)NR^{c2}R^{d2}$, $C(O)NR^{c2}(OR^{a2})$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$alkyl-, and (4-7 membered heterocycloalkyl)-$C_{1-6}$ alkyl- of $R^2$ are each optionally substituted with 1, 2, 3, or 4 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, and $C_{3-7}$ cycloalkyl, wherein the $C_{1-6}$ alkyl, $C_{2-6}$ alkenyl, $C_{2-6}$ alkynyl, and $C_{3-7}$ cycloalkyl of $R^{a2}$, $R^{b2}$, $R^{c2}$, and $R^{d2}$ are each optionally substituted with 1, 2, 3, or 4 independently selected $R^{2A}$ substituents;

each $R^{2A}$ is independently selected from OH, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

$R^3$ is selected from H, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b3}$, $C(O)NR^{c3}R^{d3}$, $C(O)OR^{a3}$, $C(=NR^{e3})R^{b3}$, $C(=NR^{e3})NR^{c3}R^{d3}$, $S(O)_2R^{b3}$, and $S(O)_2NR^{c3}R^{d3}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^3$ are each optionally substituted with 1, 2, 3, or 4 independently selected $R^{3A}$ substituents;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a3}$, $R^{b3}$, $R^{c3}$, and $R^{d3}$, are each optionally substituted with 1, 2, 3, or 4 independently selected $R^{3A}$ substituents;

or, any $R^{c3}$ and $R^{d3}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{3A}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^4$ is selected from H, $C_{1-6}$ alkyl, $C_{1-6}$ haloalkyl, $C_{2-6}$ alkenyl, and $C_{2-6}$ alkynyl, wherein the $C_{1-6}$ alkyl are each optionally substituted with OH, CN and $NH_2$;

$R^5$ and $R^6$ are each independently selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^a$, $SR^a$, $NHOR^a$, $C(O)R^b$, $C(O)NR^cR^d$, $C(O)NR^c(OR^a)$, $C(O)OR^a$, $OC(O)R^b$, $OC(O)NR^cR^d$, $NR^cR^d$, $NR^c$-$NR^cR^d$, $NR^cC(O)R^b$, $NR^cC(O)OR^a$, $NR^cC(O)NR^cR^d$, $C(=NR^e)R^b$, $C(=NOH)R^b$, $C(=NCN)R^b$, $C(=NR^e)NR^cR^d$, $NR^cC(=NR^e)NR^cR^d$, $NR^cC(=NOH)NR^cR^d$, $NR^cC(=NCN)NR^cR^d$, $NR^cC(=NR^e)R^b$, $NR^cS(O)NR^cR^d$, $NR^cS(O)R^b$, $NR^cS(O)_2R^b$, $NR^cS(O)(=NR^e)R^b$, $NR^cS(O)_2NR^cR^d$, $S(O)R^b$, $S(O)NR^cR^d$, $S(O)_2R^b$, $S(O)_2NR^cR^d$, $OS(O)(=NR^e)R^b$, $OS(O)_2R^b$, $SF_5$, $P(O)R^fR^g$, $OP(O)(OR^h)(OR^i)$, $P(O)(OR^h)(OR^i)$, and $BR^jR^k$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ and $R^6$ are each optionally substituted with 1, 2, 3, or 4 independently selected $R^A$ substituents;

each $R^a$, $R^b$, $R^c$, and $R^d$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^a$, $R^b$, $R^c$, and $R^d$, are each optionally substituted with 1, 2, 3, or 4 independently selected $R^A$ substituents;

or, any $R^c$ and $R^d$, attached to the same N atom, together with the N atom to which they are attached, form a 5- or 6-membered heteroaryl or a 4-10-membered heterocycloalkyl group, wherein the 5- or 6-membered heteroaryl or 4-10-membered heterocycloalkyl group is optionally substituted with 1, 2, 3, or 4 independently selected $R^A$ substituents;

each $R^e$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^f$ and $R^g$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^h$ and $R^i$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^j$ and $R^k$ is independently selected from OH, $C_{1-6}$ alkoxy, and $C_{1-6}$ haloalkoxy;

or any $R^j$ and $R^k$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^A$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a16}$, $SR^{a16}$, $NHOR^{a16}$, $C(O)R^{b16}$, $C(O)NR^{c16}R^{d16}$, $C(O)NR^{c16}(OR^{a16})$, $C(O)OR^{a16}$, $OC(O)R^{b16}$, $OC(O)NR^{c16}R^{d16}$, $NR^{c16}R^{d16}$, $NR^{c16}NR^{c16}R^{d16}$, $NR^{c16}C(O)R^{b16}$, $NR^{c16}C(O)OR^{a16}$, $NR^{c16}C(O)NR^{c16}R^{d16}$, $C(=NR^{e16})R^{b16}$, $C(=NOH)R^{b16}$, $C(=NCN)R^{b16}$, $C(=NR^{e16})NR^{c16}R^{d16}$, $NR^{c16}C(=NR^{e16})NR^{c16}R^{d16}$, $NR^{c16}C(=NOH)NR^{c16}R^{d16}$, $NR^{c16}C(=NCN)NR^{c16}R^{d16}$, $NR^{16}C(=NR^{e16})R^{b16}$, $NR^{c16}S(O)NR^{c16}R^{d16}$, $NR^{c16}S(O)R^{b16}$, $NR^{c16}S(O)_2R^{b16}$, $NR^{c16}S(O)(=NR^{e16})R^{b16}$, $NR^{c16}S(O)_2NR^{c16}R^{d16}$, $S(O)R^{b16}$, $S(O)NR^{c16}R^{d16}$, $S(O)_2R^{b16}$, $S(O)_2NR^{c16}R^{d16}$, $OS(O)(=NR^{e16})R^{b16}$, $OS(O)_2R^{b16}$, $SF_5$, $P(O)R^{f16}R^{g16}$, $OP(O)(OR^{h16})(OR^{i16})$, $P(O)(OR^{h16})(OR^{i16})$, and $BR^{j16}R^{k16}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents;

each $R^{a16}$, $R^{b16}$, $R^{c16}$, and $R^{d16}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a16}$, $R^{b16}$, $R^{c16}$, and $R^{d16}$, are each optionally substituted with 1, 2, 3, or 4 independently selected $R^B$ substituents;

or, any $R^{c16}$ and $R^{d16}$, attached to the same N atom, together with the N atom to which they are attached, form a 5- or 6-membered heteroaryl or a 4-10-membered heterocycloalkyl group, wherein the 5- or 6-membered heteroaryl or 4-10-membered heterocycloalkyl group is optionally substituted with 1, 2, 3, or 4 independently selected $R^B$ substituents;

each $R^{e16}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f16}$ and $R^{g16}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h16}$ and $R^{i16}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j16}$ and $R^{k16}$ is independently selected from OH, $C_{1-6}$ alkoxy, and $C_{1-6}$ haloalkoxy;

or any $R^{j16}$ and $R^{k16}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^B$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a26}$, $SR^{a26}$, $NHOR^{a26}$, $C(O)R^{b26}$, $C(O)NR^{c26}R^{d26}$, $C(O)NR^{c26}(OR^{a26})$, $C(O)OR^{a26}$, $OC(O)R^{b26}$, $OC(O)NR^{c26}R^{d26}$, $NR^{c26}R^{d26}$, $NR^{c26}NR^{c26}R^{d26}$, $NR^{c26}C(O)R^{b26}$, $NR^{c26}C(O)OR^{a26}$, $NR^{c26}C(O)NR^{c26}R^{d26}$, $C(=NR^{e26})R^{b26}$, $C(=NOH)R^{b26}$, $C(=NCN)R^{b26}$, $C(=NR^{e26})NR^{c26}R^{d26}$, $NR^{c26}C(=NR^{e26})NR^{c26}R^{d26}$, $NR^{c26}C(=NOH)NR^{c26}R^{d26}$, $NR^{c26}C(=NCN)NR^{c26}R^{d26}$, $NR^{c26}C(=NR^{e26})R^{b26}$, $NR^{c26}S(O)NR^{c26}R^{d26}$, $NR^{c26}S(O)R^{b26}$, $NR^{c26}S(O)_2R^{b26}$, $NR^{c26}S(O)(=NR^{e26})R^{b26}$, $NR^{c26}S(O)_2NR^{c26}R^{d26}$, $S(O)R^{b26}$, $S(O)NR^{c26}R^{d26}$, $S(O)_2R^{b26}$, $S(O)_2NR^{c26}R^{d26}$, $OS(O)(=NR^{e26})R^{b26}$, $OS(O)_2R^{b26}$, $SF_5$, $P(O)R^{f26}R^{g26}$, $OP(O)(OR^{h26})(OR^{i26})$, $P(O)(OR^{h26})(OR^{i26})$, and $BR^{j26}R^{k26}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ are each optionally substituted with 1, 2, 3, or 4 independently selected $R^C$ substituents;

each $R^{a26}$, $R^{b26}$, $R^{c26}$, and $R^{d26}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a26}$, $R^{b26}$, $R^{c26}$, and $R^{d26}$, are each optionally substituted with, 1, 2, 3, or 4 independently selected $R^C$ substituents;

or, any $R^{c26}$ and $R^{d26}$, attached to the same N atom, together with the N atom to which they are attached, form a 5- or 6-membered heteroaryl or a 4-10-membered heterocycloalkyl group, wherein the 5- or 6-membered heteroaryl or 4-10-membered heterocycloalkyl group is optionally substituted with 1, 2, 3, or 4 independently selected $R^C$ substituents;

each $R^{e26}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{e26}$ and $R^{g26}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h26}$ and $R^{i26}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j26}$ and $R^{k26}$ is independently selected from OH, $C_{1-6}$ alkoxy, and $C_{1-6}$ haloalkoxy;

or any $R^{j26}$ and $R^{k26}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^C$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a36}$, $SR^{a36}$, $NHOR^{a36}$, $C(O)R^{b36}$, $C(O)NR^{c36}R^{d36}$, $C(O)NR^{c36}(OR^{a36})$, $C(O)OR^{a36}$, $OC(O)R^{b36}$, $OC(O)NR^{c36}R^{d36}$, $NR^{c36}R^{d36}$ $NR^{c36}NR^{c36}R^{d36}$, $NR^{c36}C(O)R^{b36}$, $NR^{c36}C(O)OR^{a36}$, $NR^{c36}C(O)NR^{c36}R^{d36}$, $C(=NR^{e36})R^{b36}$, $C(=NOH)R^{b36}$, $C(=NCN)R^{b36}$, $C(=NR^{e36})NR^{c36}R^{d36}$, $NR^{c36}C(=NR^{e36})NR^{c36}R^{d36}$ $NR^{c36}C(=NOH)NR^{c36}R^{d36}$, $NR^{c36}C(=NCN)NR^{c36}R^{d36}$, $NR^{c36}C(=NR^{e36})R^{b36}$, $NR^{c36}S(O)NR^{c36}R^{d36}$ $NR^{c36}S(O)R^{b36}$, $NR^{c36}S(O)_2R^{b36}$, $NR^{c36}S(O)(=NR^{e36})R^{b36}$, $NR^{c36}S(O)_2NR^{c36}R^{d36}$, $S(O)R^{b36}$, $S(O)NR^{c36}R^{d36}$, $S(O)_2R^{b36}$, $S(O)_2NR^{c36}R^{d36}$, $OS(O)(=NR^{e36})R^{b36}$, $OS(O)_2R^{b36}$, $SF_5$, $P(O)R^{f36}R^{g36}$, $OP(O)(OR^{h36})(OR^{i36})$, $P(O)(OR^{c36})(OR^{c36})$, and $BR^{j36}R^{k36}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^C$ are each optionally substituted with 1, 2, 3, or 4 independently selected $R^D$ substituents;

each $R^{a36}$, $R^{b36}$, $R^{c36}$, and $R^{d36}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a36}$, $R^{b36}$, $R^{c36}$, and $R^{d36}$, are each optionally substituted with 1, 2, 3, or 4 independently selected $R^D$ substituents;

or, any $R^{c36}$ and $R^{d36}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^D$ substituents;

each $R^{e36}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f36}$ and $R^{g36}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h36}$ and $R^{i36}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j36}$ and $R^{k36}$ is independently selected from OH, $C_{1-6}$ alkoxy, and $C_{1-6}$ haloalkoxy;

or any $R^{j36}$ and $R^{k36}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^D$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a46}$, $SR^{a46}$, $NHOR^{a46}$, $C(O)R^{b46}$, $C(O)NR^{c46}R^{d46}$, $C(O)NR^{c46}(OR^{a46})$, $C(O)OR^{a46}$, $OC(O)R^{b46}$, $OC(O)NR^{c46}R^{d46}$, $NR^{c46}R^{d46}$, $NR^{c46}NR^{c46}R^{d46}$, $NR^{c46}C(O)R^{b46}$, $NR^{c46}C(O)OR^{a46}$, $NR^{c46}C(O)NR^{c46}R^{d46}$, $C(=NR^{e46})R^{b46}$, $C(=NOH)R^{b46}$, $C(=NCN)R^{b46}$, $C(=NR^{e46})NR^{c46}R^{d46}$, $NR^{c46}C(=NR^{e46})NR^{c46}R^{d46}$ $NR^{c46}C(=NOH)NR^{c46}R^{d46}$, $NR^{c46}C(=NCN)NR^{c46}R^{d46}$, $NR^{c46}C(=NR^{e46})R^{b46}$, $NR^{c46}S(O)NR^{c46}R^{d46}$ $NR^{c46}S(O)R^{b46}$, $NR^{c46}S(O)_2R^{b46}$, $NR^{c46}S(O)(=NR^{e46})R^{b46}$, $NR^{c46}S(O)_2NR^{c46}R^{d46}$, $S(O)R^{b46}$ $S(O)NR^{c46}R^{d46}$, $S(O)_2R^{b46}$, $S(O)_2NR^{c46}R^{d46}$, $OS(O)(=NR^{e46})R^{b46}$, $OS(O)_2R^{b46}$, $SF_5$, $P(O)R^{f46}R^{g46}$, $OP(O)(OR^{h46})(OR^{i46})$, $P(O)(OR^{h46})(OR^{i46})$, and $BR^{j46}R^{k46}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^D$ are each optionally substituted with 1, 2, 3, or 4 independently selected $R^E$ substituents;

each $R^{a46}$, $R^{b46}$, $R^{c46}$, and $R^{d46}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a46}$, $R^{b46}$, $R^{c46}$, and $R^{d46}$, are each optionally substituted with 1, 2, 3, or 4 independently selected $R^E$ substituents;

or, any $R^{c46}$ and $R^{d46}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^E$ substituents;

each $R^{e46}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f46}$ and $R^{g46}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h46}$ and $R^{i46}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{j46}$ and $R^{k46}$ is independently selected from OH, $C_{1-6}$ alkoxy, and $C_{1-6}$ haloalkoxy;

or any $R^{j46}$ and $R^{k46}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^E$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-6}$ alkyl-" linking groups, are optionally replaced by deuterium atoms.

In some embodiments:

$X^1$ is N or $CR^1$;

$R^1$ is selected from H, D and $C_{1-6}$ alkyl;

$R^2$ is selected from H, D, halo, $C_{1-6}$ alkyl and $C_{1-6}$ haloalkyl;

$R^3$ is selected from H and $C_{1-6}$ alkyl;

$R^4$ is selected from H and $C_{1-6}$ alkyl;

$R^5$ is selected from H, D, halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl- and CN, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 substituents independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl- and (4-10 membered heterocycloalkyl)-$C_{1-6}$ alkyl-;

$R^6$ is selected from H, D, halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^A$ substituents;

$R^A$ is selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a16}$, $SR^{a16}$, $NHOR^{a16}$, $C(O)R^{b16}$, $C(O)NR^{c16}R^{d16}$, $C(O)NR^{c16}(OR^{a16})$, $C(O)OR^{a16}$, $OC(O)R^{b16}$, $OC(O)NR^{c16}R^{d16}$, $NR^{c16}R^{d16}$, $NR^{c16}NR^{c16}R^{d16}$, $NR^{c16}C(O)R^{b16}$, $NR^{c16}C(O)OR^{a16}$, $NR^{c16}C(O)NR^{c16}R^{d16}$, $C(=NR^{e16})R^{b16}$ $C(=NOH)R^{b16}$, $C(=NCN)R^{b16}$, $C(=NR^{e16})NR^{c16}R^{d16}$, $NR^{c16}C(=NR^{e16})NR^{c16}R^{d16}$, $NR^{c16}C(=NOH)NR^{c16}R^{d16}$, $NR^{c16}C(=NCN)NR^{c16}R^{d16}$, $NR^{c16}C(=NR^{e16})R^{b16}$, $NR^{c16}S(O)NR^{c16}R^{d16}$, $NR^{c16}S(O)R^{b16}$, $NR^{c16}S(O)_2R^{b16}$, $NR^{c16}S(O)(=NR^{e16})R^{b16}$, $NR^{c16}S(O)_2NR^{c16}R^{d16}$, $S(O)R^{b16}$, $S(O)NR^{c16}R^{d16}$, $S(O)_2R^{b16}$, $S(O)_2NR^{c16}R^{d16}$, $OS(O)(=NR^{e16})R^{b16}$, $OS(O)_2R^{b16}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents;

each $R^{a16}$, $R^{b16}$, $R^{c16}$, and $R^{d16}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a16}$, $R^{b16}$, $R^{c16}$, and $R^{d16}$, are each optionally substituted with 1, 2, 3, or 4 independently selected $R^B$ substituents;

or, any $R^{c16}$ and $R^{d16}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^B$ substituents;

each $R^{e16}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

$R^B$ is selected from halo, $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a26}$, $SR^{a26}$, $NHOR^{a26}$, $C(O)R^{b26}$, $C(O)NR^{c26}R^{d26}$, $C(O)NR^{c26}(OR^{a26})$, $C(O)OR^{a26}$, $OC(O)R^{b26}$, $OC(O)NR^{c26}R^{d26}$, $NR^{c26}R^{d26}$, $NR^{c26}NR^{c26}R^{d26}$, $NR^{c26}C(O)R^{b26}$, $NR^{c26}C(O)OR^{a26}$, $NR^{c26}C(O)NR^{c26}R^{d26}$, $C(=NR^{e26})R^{b26}$, $C(=NOH)R^{b26}$, $C(=NCN)R^{b26}$, $C(=NR^{e26})NR^{c26}R^{d26}$, $NR^{c26}C(=NR^{e26})NR^{c26}R^{d26}$, $NR^{c26}C(=NOH)NR^{c26}R^{d26}$, $NR^{c26}C(=NCN)NR^{c26}R^{d26}$, $NR^{c26}C(=NR^{e26})R^{b26}$, $NR^{c26}S(O)NR^{c26}R^{d26}$, $NR^{c26}S(O)R^{b26}$, $NR^{c26}S(O)_2R^{b26}$, $NR^{c26}S(O)(=NR^{e26})R^{b26}$, $NR^{c26}S(O)_2NR^{c26}R^{d26}$, $S(O)R^{b26}$, $S(O)NR^{c26}R^{d26}$, $S(O)_2R^{b26}$, $S(O)_2NR^{c26}R^{d26}$, $OS(O)(=NR^{e26})R^{b26}$, $OS(O)_2R^{b26}$, and $SF_5$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ are each optionally substituted with 1, 2, 3, or 4 independently selected $R^C$ substituents;

each $R^{a26}$, $R^{b26}$, $R^{c26}$, and $R^{d26}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a26}$, $R^{b26}$, $R^{c26}$, and $R^{d26}$, are each optionally substituted with 1, 2, 3, or 4 independently selected $R^C$ substituents;

or, any $R^{c26}$ and $R^{d26}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^C$ substituents;

each $R^{e26}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

$R^C$ is selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a36}$, $SR^{a36}$, $NHOR^{a36}$, $C(O)R^{b36}$, $C(O)NR^{c36}R^{d36}$, $C(O)NR^{c36}(OR^{a36})$, $C(O)OR^{a36}$, $OC(O)R^{b36}$, $OC(O)NR^{c36}R^{d36}$, $NR^{c36}R^{d36}$, $NR^{c36}NR^{c36}R^{d36}$, $NR^{c36}C(O)R^{b36}$, $NR^{c36}C(O)OR^{a36}$, $NR^{c36}C(O)NR^{c36}R^{d36}$, $C(=NR^{e36})R^{b36}$, $C(=NOH)R^{b36}$, $C(=NCN)R^{b36}$, $C(=NR^{e36})NR^{c36}R^{d36}$, $NR^{c36}C(=NR^{e36})NR^{c36}R^{d36}$, $NR^{c36}C(=NOH)NR^{c36}R^{d36}$ $NR^{c36}C(=NCN)NR^{c36}R^{d36}$, $NR^{c36}C(=NR^{e36})R^{b36}$, $NR^{c36}S(O)NR^{c36}R^{d36}$, $NR^{c36}S(O)R^{b36}$, $NR^{c36}S(O)_2R^{b36}$, $NR^{c36}S(O)(=NR^{e36})R^{b36}$, $NR^{c36}S(O)_2NR^{c36}R^{d36}$, $S(O)R^{b36}$, $S(O)NR^{c36}R^{d36}$ $S(O)_2R^{b36}$, $S(O)_2NR^{c36}R^{d36}$, $OS(O)(=NR^{e36})R^{b36}$, $OS(O)_2R^{b36}$, and $SF_5$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^C$ are each optionally substituted with 1, 2, 3, or 4 independently selected $R^D$ substituents;

each $R^{a36}$, $R^{b36}$, $R^{c36}$, and $R^{d36}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a36}$, $R^{b36}$, $R^{c36}$, and $R^{d36}$, are each optionally substituted with 1, 2, 3, or 4 independently selected $R^D$ substituents;

or, any $R^{c36}$ and $R^{d36}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^D$ substituents;

each $R^{e36}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

$R^D$ is selected from halo, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- CN, $NO_2$, $OR^{a46}$, $SR^{a46}$, $NHOR^{a46}$, $C(O)R^{b46}$, $C(O)NR^{c46}R^{d46}$, $C(O)NR^{c46}(OR^{a46})$, $C(O)OR^{a46}$, $OC(O)R^{b46}$, $OC(O)NR^{c46}R^{d46}$, $NR^{c46}R^{d46}$, $NR^{c46}NR^{c46}R^{d46}$, $NR^{c46}C(O)R^{b46}$, $NR^{c46}C(O)OR^{a46}$, $NR^{c46}C(O)NR^{c46}R^{d46}$, $C(=NR^{e46})R^{b46}$, $C(=NOH)R^{b46}$, $C(=NCN)R^{b46}$, $C(=NR^{e46})NR^{c46}R^{d46}$, $NR^{c46}C(=NR^{e46})NR^{c46}R^{d46}$, $NR^{c46}C(=NOH)NR^{c46}R^{d46}$, $NR^{c46}C(=NCN)NR^{c46}R^{d46}$, $NR^{c46}C(=NR^{e46})R^{b46}$, $NR^{c46}S(O)NR^{c46}R^{d46}$, $NR^{c46}S(O)R^{b46}$, $NR^{c46}S(O)_2R^{b46}$, $NR^{c46}S(O)(=NR^{e46})R^{b46}$, $NR^{c46}S(O)_2NR^{c46}R^{d46}$, $S(O)R^{b46}$, $S(O)NR^{c46}R^{d46}$, $S(O)_2R^{b46}$, $S(O)_2NR^{c46}R^{d46}$, $OS(O)(=NR^{e46})R^{b46}$, $OS(O)_2R^{b46}$, and $SF_5$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^D$ are each optionally substituted with 1, 2, 3, or 4 independently selected $R^E$ substituents;

each $R^{a46}$, $R^{b46}$, $R^{c46}$, and $R^{d46}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a46}$, $R^{b46}$, $R^{c46}$, and $R^{d46}$, are each optionally substituted with 1, 2, 3, or 4 independently selected $R^E$ substituents;

or, any $R^{c46}$ and $R^{d46}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^E$ substituents;

each $R^{e46}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^E$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylcarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

wherein 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-6}$ alkyl-" linking groups, are optionally replaced by deuterium atoms.

In some embodiments, $R^1$ is selected from H, D, halo and $C_{1-6}$ alkyl.

In some embodiments, $R^1$ is selected from H, D and $C_{1-6}$ alkyl.

In some embodiments, $R^1$ is selected from H, $C_{1-6}$ alkyl, and $C_{1-6}$ haloalkyl.

In some embodiments, $R^1$ is selected from H and $C_{1-6}$ alkyl.

In some embodiments, $R^1$ is H, $CH_3$, or $CD_3$.

In some embodiments, $R^1$ is H or methyl.

In some embodiments, $R^1$ is H.

In some embodiments, $R^2$ is selected H, D, halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- and CN, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^2$ are each optionally substituted with 1, 2, 3, or 4 independently selected $R^{2A}$ substituents.

In some embodiments, $R^2$ is selected from H, D, halo, $C_{1-6}$ alkyl, $C_{1-6}$ haloalkyl, $C_{2-6}$ alkenyl, $C_{2-6}$ alkynyl, CN, $OR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl of $R^2$ are each optionally substituted with 1, 2, 3, or 4 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, and $C_{2-6}$ alkynyl wherein the $C_{1-6}$ alkyl, $C_{2-6}$ alkenyl, and $C_{2-6}$ alkynyl of $R^{a2}$, $R^{b2}$, $R^{c2}$, and $R^{d2}$ are each optionally substituted with 1, 2, 3, or 4 independently selected $R^{2A}$ substituents; and each $R^{2A}$ is independently selected from D, OH, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino.

In some embodiments, $R^2$ is selected H, D, halo, $C_{1-6}$ alkyl, and $C_{1-6}$ haloalkyl.

In some embodiments, $R^2$ is selected from H, $C_{1-6}$ alkyl, and $C_{1-6}$ haloalkyl.

In some embodiments, $R^2$ is selected from H, $CH_3$, $CD_3$, and $CF_3$.

In some embodiments, $R^2$ is selected from $CH_3$ and $CF_3$.

In some embodiments, $R^2$ is selected from H, D, methyl and $CF_3$.

In some embodiments, $R^2$ is selected from H, methyl and $CF_3$.

In some embodiments, $R^2$ is methyl.

In some embodiments, $R^2$ is $CF_3$.

In some embodiments, $R^3$ is selected from H, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^3$ are each optionally substituted with 1, 2, 3, or 4 independently selected $R^{3A}$ substituents.

In some embodiments, $R^3$ is selected from H, $C_{1-6}$ alkyl, $C_{2-6}$ alkenyl, $C_{2-6}$ alkynyl, $C_{1-6}$ haloalkyl, $C(O)R^{b3}$, $C(O)NR^{c3}R^{d3}$, $C(O)OR^{a3}$, $C(=NR^{e3})R^{b3}$, $C(=NR^{e3})NR^{c3}R^{d3}$, $S(O)_2R^{b3}$, and $S(O)_2NR^{c3}R^{d3}$, wherein the $C_{1-6}$ alkyl, $C_{2-6}$ alkenyl, and $C_{2-6}$ alkynyl of $R^3$ are each optionally substituted with 1, 2, 3, or 4 independently selected $R^{3A}$ substituents.

In some embodiments, $R^3$ is selected from H, $C_{1-6}$ alkyl and $C_{1-6}$ haloalkyl.

In some embodiments, $R^3$ is selected from H and $C_{1-6}$ alkyl.

In some embodiments, $R^3$ is $C_{1-6}$ alkyl.

In some embodiments, $R^3$ is selected from methyl, ethyl, propyl, butyl, and pentyl.

In some embodiments, $R^3$ is selected from pentyl and butyl.

In some embodiments, $R^3$ is pentyl.

In some embodiments, $R^3$ is butyl

In some embodiments, $R^3$ is propyl

In some embodiments, $R^3$ is ethyl.

In some embodiments, $R^3$ is methyl.

In some embodiments, $R^3$ is H.

In some embodiments, $R^4$ is selected from H and $C_{1-6}$ alkyl, wherein the $C_{1-6}$ alkyl is optionally substituted with OH, CN, and $NH_2$.

In some embodiments, $R^4$ is selected from H and $C_{1-6}$ alkyl.

In some embodiments, $R^4$ is selected from H and methyl.

In some embodiments, $R^4$ is H.

In some embodiments, $R^5$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^a$, $C(O)R^b$, $C(O)NR^cR^d$, $C(O)NR^c(OR^a)$, $C(O)OR^a$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)R^b$, $S(O)_2R^b$, and $S(O)_2NR^cR^d$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^4$ substituents.

In some embodiments, $R^5$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl- and CN, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 substituents, independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-.

In some embodiments, $R^5$ is selected from H, D, halo, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl- and CN, wherein the $C_{1-6}$ alkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^5$ are each optionally substituted with 1, 2, 3, or 4 substituents independently selected from halo, $C_{1-6}$ alkyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl, and (4-7 membered heterocycloalkyl)-$C_{1-6}$ alkyl-.

In some embodiments, $R^5$ is selected from H, D, halo, CN, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein said $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are optionally substituted by 1, 2, 3, or 4 independently selected $R^4$ substituents.

In some embodiments, $R^5$ is selected from H, D, halo, CN, $C_{1-6}$ alkyl, $C_{6-10}$ aryl, and (5-10 membered heteroaryl)-$C_{1-6}$ alkyl-, wherein said $C_{6-10}$ aryl and (5-10 membered heteroaryl)-$C_{1-6}$ alkyl- of $R^5$ are optionally substituted by 1, 2, 3, or 4 independently selected $R^4$ substituents.

In some embodiments, $R^5$ is selected from H, halo, CN, $C_{1-6}$ alkyl, $C_{6-10}$ aryl, and (5-10 membered heteroaryl)-$C_{1-6}$ alkyl-, wherein said $C_{6-10}$ aryl and (5-10 membered heteroaryl)-$C_{1-6}$ alkyl- of $R^5$ are optionally substituted by 1 $R^4$ substituent.

In some embodiments, $R^5$ is selected from $C_{6-10}$ aryl and (5-10 membered heteroaryl)-$C_{1-6}$ alkyl-, wherein said $C_{6-10}$ aryl and (5-10 membered heteroaryl)-$C_{1-6}$ alkyl- of $R^5$ are optionally substituted by 1, 2, 3, or 4 independently selected $R^4$ substituents.

In some embodiments, $R^5$ is selected from H, Br, CN, $CH_3$, phenyl, and pyrazol-4-yl, wherein the pyrazol-4-yl of $R^5$ is optionally substituted with benzyl.

In some embodiments, $R^5$ is selected from H, D, halo, $C_{1-6}$ alkyl, phenyl, (5-6 membered heteroaryl)-$C_{1-6}$ alkyl-, (4-7 membered heterocycloalkyl)-$C_{1-6}$ alkyl- and CN, wherein the phenyl, (5-6 membered heteroaryl)-$C_{1-6}$ alkyl-, and (4-7 membered heterocycloalkyl)-$C_{1-6}$ alkyl- of $R^5$ are each optionally substituted with phenyl.

In some embodiments, $R^5$ is pyrazolyl $C_{1-6}$ alkyl, optionally substituted with phenyl.

In some embodiments, $R^5$ is 1-benzyl-1H-pyrazole.

In some embodiments, $R^5$ is halo.

In some embodiments, $R^5$ is $C_{1-6}$ alkyl.

In some embodiments, $R^5$ is methyl.

In some embodiments, $R^5$ is phenyl.

In some embodiments, $R^5$ is cyano.

In some embodiments, $R^6$ is selected from H, D, Cl, F, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^a$, $SR^a$, $NHOR^a$, $C(O)R^b$, $C(O)NR^cR^d$, $C(O)NR^c(OR^a)$, $C(O)OR^a$, $OC(O)R^b$, $OC(O)NR^cR^d$, $NR^cR^d$, $NR^c\text{-}NR^cR^d$, $NR^cC(O)R^b$, $NR^cC(O)OR^a$, $NR^cC(O)NR^cR^d$, $C(=NR^e)R^b$, $C(=NOH)R^b$, $C(=NCN)R^b$, $C(=NR^e)NR^c$ $R^d$, $NR^cC(=NR^e)NR^cR^d$, $NR^cC(=NOH)NR^cR^d$, $NR^cC(=NCN)NR^cR^d$, $NR^cC(=NR^e)R^b$, $NR^cS(O)NR^cR^d$, $NR^cS(O)R^b$, $NR^cS(O)_2R^b$, $NR^cS(O)(=NR^e)R^b$, $NR^cS(O)_2NR^c R^d$, $S(O)R^b$, $S(O)NR^cR^d$, $S(O)_2R^b$, $S(O)_2NR^cR^d$, $OS(O)(=NR^e)R^b$, $OS(O)_2R^b$, $SF_5$, $P(O)R^fR^g$, $OP(O)(OR^h)(OR^i)$, $P(O)(OR^h)(OR^i)$, and $BR^jR^k$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^A$ substituents.

In some embodiments, $R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^a$, $C(O)R^b$, $C(O)NR^cR^d$, $C(O)NR^c(OR^a)$, $C(O)OR^a$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)R^b$, $S(O)_2R^b$, and $S(O)_2NR^c R^d$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^A$ substituents.

In some embodiments, $R^6$ is selected from H, D, halo, CN, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein said $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are optionally substituted by 1, 2, 3, or 4 independently selected $R^A$ substituents.

In some embodiments, $R^6$ is selected from H, D, halo, CN, $C_{1-6}$ alkyl, $C_{6-10}$ aryl, and (5-10 membered heteroaryl)-$C_{1-6}$ alkyl-, wherein said $C_{6-10}$ aryl and (5-10 membered heteroaryl)-$C_{1-6}$ alkyl- of $R^6$ are optionally substituted by 1, 2, 3, or 4 independently selected $R^A$ substituents.

In some embodiments, $R^6$ is selected from H, $C_{6-10}$ aryl, and (5-10 membered heteroaryl)-$C_{1-6}$ alkyl-, wherein said $C_{6-10}$ aryl and (5-10 membered heteroaryl)-$C_{1-6}$ alkyl- of $R^6$ are optionally substituted by 1, 2, 3, or 4 independently selected $R^A$ substituents.

In some embodiments, $R^6$ is selected from $C_{6-10}$ aryl and (5-10 membered heteroaryl)-$C_{1-6}$ alkyl-, wherein said $C_{6-10}$ aryl and (5-10 membered heteroaryl)-$C_{1-6}$ alkyl- of $R^6$ are optionally substituted by 1 $R^A$ substituent.

In some embodiments, $R^6$ is selected from H, phenyl, and pyrazol-4-yl, wherein said phenyl and pyrazol-4-yl of $R^6$ are each independently substituted by 1, 2, 3, or 4 independently selected $R^A$ substituents.

In some embodiments:

each $R^A$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a16}$, $SR^{a16}$, $NHOR^{a16}$, $C(O)R^{b16}$, $C(O)NR^{c16}R^{d16}$, $C(O)NR^{c16}(OR^{a16})$, $C(O)OR^{a16}$, $OC(O)R^{b16}$, $OC(O)NR^{c16}R^{d16}$, $NR^{c16}R^{d16}$, $NR^{16}C(O)R^{b16}$, $NR^{c16}C(O)OR^{a16}$, $NR^{16}C(O)NR^{c16}R^{d16}$, $NR^{c16}S(O)_2R^{b16}$, $NR^{c16}S(O)_2NR^{c16}R^{d16}$, $S(O)_2R^{b16}$, and $S(O)_2NR^{c16}R^{d16}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents; and each $R^{a16}$, $R^{b16}$, $R^{c16}$, and $R^{d16}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a16}$, $R^{b16}$, $R^{c16}$, and $R^{d16}$, are each optionally substituted with 1, 2, 3, or 4 independently selected $R^B$ substituents.

In some embodiments:

each $R^A$ is independently selected from (5-10 membered heteroaryl)-$C_{1-6}$ alkyl-, (4-10 membered heterocycloalkyl)-$C_{1-6}$ alkyl-, and $S(O)_2NR^{c16}R^{d16}$, wherein the (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents; and each $R^{i16}$ and $R^{d16}$ is independently selected from H and $C_{6-10}$ aryl, wherein the $C_{6-10}$ aryl of $R^{C16}$ and $R^{d16}$ is optionally substituted with 1, 2, 3, or 4 independently selected $R^B$ substituents.

In some embodiments, each $R^A$ is independently selected from $S(O)_2NR^{c16}R^{d16}$, benzyl, azetidin-3-yl, pyridin-3-yl, thieno[3,2-b]pyridin-6-ylmethyl, imidazo[1,2-a]pyridin-7-ylmethyl, 1,5-naphthyridin-3-ylmethyl, 1H-pyrazolo[4,3-b]pyridin-6-ylmethyl, and 1,2,3,4-tetrahydroisoquinolin-6-ylmethyl, each which are optionally substituted by 1, 2, 3, or 4 independently selected $R^B$ substituents.

In some embodiments:

each $R^B$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a26}$, $SR^{a26}$, $NHOR^{a26}$, $C(O)R^{b26}$, $C(O)NR^{c26}R^{d26}$, $C(O)OR^{a26}$, $OC(O)R^{b26}$, $OC(O)NR^{c26}R^{d26}$, $NR^{c26}R^{d26}$, $NR^{c26}C(O)R^{b26}$, $NR^{c26}C(O)OR^{a26}$, $NR^{c26}C(O)NR^{c26}R^{d26}$, $NR^{c26}S(O)_2R^{b26}$, $NR^{c26}S(O)_2NR^{c26}R^{d26}$, $S(O)_2R^{b26}$, and $S(O)_2NR^{c26}R^{d26}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ are each optionally substituted with 1, 2, 3, or 4 independently selected $R^C$ substituents; and each $R^{a26}$, $R^{b26}$, $R^{c26}$, and $R^{d26}$ is independently selected from H, $C_{1-6}$ alkyl, and $C_{1-6}$ haloalkyl, wherein the $C_{1-6}$ alkyl of $R^{a26}$, $R^{b26}$, $R^{c26}$, and $R^{d26}$ is optionally substituted with 1, 2, 3, or 4 independently selected $R^C$ substituents.

In some embodiments:

each $R^B$ is independently selected from halo, $C_{1-6}$ alkyl, 5-10 membered heteroaryl, $C(O)R^{b26}$, and $C(O)NR^{c26}R^{d26}$, wherein the 5-10 membered heteroaryl of $R^B$ are each optionally substituted with 1, 2, 3, or 4 independently selected $R^C$ substituents; and each $R^{b26}$, $R^{c26}$, and $R^{d26}$ is independently selected from H and $C_{1-6}$ alkyl, wherein the $C_{1-6}$ alkyl of $R^{b26}$, $R^{c26}$, and $R^{d26}$ is optionally substituted with 1, 2, 3, or 4 independently selected $R^C$ substituents.

In some embodiments:

each $R^C$ is independently selected from halo, $C_{1-6}$ alkyl, $C_{1-6}$ haloalkyl, $C_{2-6}$ alkenyl, $C_{2-6}$ alkynyl, CN, $OR^{a36}$, $SR^{a36}$, $NHOR^{a36}$, $C(O)R^{b36}$, $C(O)NR^{c36}R^{d36}$, $C(O)OR^{a36}$, $OC(O)R^{b36}$, $OC(O)NR^{c36}R^{d36}$, $NR^{c36}R^{d36}$, $NR^{c36}C(O)R^{b36}$, $NR^{c36}C(O)OR^{a36}$, $NR^{c36}C(O)NR^{c36}R^{d36}$ $NR^{c36}S(O)_2R^{b36}$, $NR^{c36}S(O)_2NR^{c36}R^{d36}$, $S(O)_2R^{b36}$, and $S(O)_2NR^{c36}R^{d36}$, wherein the $C_{1-6}$ alkyl, $C_{2-6}$ alkenyl, and $C_{2-6}$ alkynyl of $R^C$ are each optionally substituted with 1, 2, 3, or 4 independently selected $R^D$ substituents; and each $R^{a36}$, $R^{b36}$, $R^{c36}$, and $R^{d36}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{a36}$, $R^{b36}R^{c36}$, and $R^{d36}$ are each optionally substituted with 1, 2, 3, or 4 independently selected $R^D$ substituents.

In some embodiments:

each $R^C$ is independently selected from halo, $C_{1-6}$ alkyl, CN, $OR^{a36}$, and $NR^{c36}R^{d36}$, wherein the $C_{1-6}$ alkyl of $R^c$ is optionally substituted with 1, 2, 3, or 4 independently selected $R^D$ substituents; and each $R^{a36}$, $R^{c36}$, and $R^{d36}$ is independently selected from H, $C_{1-6}$ alkyl, wherein the $C_{1-6}$ alkyl of $R^{a36}$, $R^{c36}$, and $R^{d36}$ is optionally substituted with 1, 2, 3, or 4 independently selected $R^D$ substituents.

In some embodiments, each $R^D$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylcarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In some embodiments, each $R^D$ is independently selected from OH, CN, halo, $C_{1-3}$ alkyl, $C_{1-3}$ haloalkyl, $C_{1-3}$ alkoxy, $C_{1-3}$ haloalkoxy, amino, $C_{1-3}$ alkylamino, and di($C_{1-3}$ alkyl) amino.

In some embodiments, each $R^D$ is OH.

In some embodiments:

$X^1$ is $CR^1$ or N;

$R^1$ is H;

$R^2$ is selected from $C_{1-6}$ alkyl and $C_{1-6}$ haloalkyl;

$R^3$ is selected from H, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b3}$, $C(O)NR^{c3}R^{d3}$, $C(O)OR^{a3}$, $C(=NR^{e3})R^{b3}$, $C(=NR^{e3})NR^{c3}R^{d3}$, $S(O)_2R^{b3}$, and $S(O)_2NR^{c3}R^{d3}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^3$ are each optionally substituted with 1, 2, 3, or 4 independently selected $R^{3A}$ substituents;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a3}$, $R^{b3}$, $R^{c3}$, and $R^{d3}$, are each optionally substituted with 1, 2, 3, or 4 independently selected $R^{3A}$ substituents;

or, any $R^{c3}$ and $R^{d3}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{3A}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl) aminosulfonylamino, aminocarbonylamino, $C_{1-3}$ alkylaminocarbonylamino, and di($C_{1-3}$ alkyl)aminocarbonylamino;

$R^4$ is H;

$R^5$ is selected from H, D, halo, CN, $C_{1-6}$ alkyl, and $C_{1-6}$ haloalkyl, wherein the $C_{1-6}$ alkyl of $R^5$ is optionally substituted by OH, CN, $C_{1-4}$ alkoxy, $C_{1-4}$ haloaloxy, amino, $C_{1-4}$ alkylamino, and di($C_{1-4}$ alkyl)amino;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^a$, $SR^a$, $NHOR^a$, $C(O)R^b$, $C(O)NR^cR^d$, $C(O)NR^c(OR^a)$, $C(O)OR^a$, $OC(O)R^b$, $OC(O)NR^cR^d$, $NR^cR^d$, $NR^cNR^cR^d$, $NR^cC(O)R^b$, $NR^cC(O)OR^a$, $NR^cC(O)NR^cR^d$, $C(=NR^e)R^b$, $C(=NOH)R^b$, $C(=NCN)R^b$, $C(=NR^e)NR^cR^d$, $NR^cC(=NR^e)NR^cR^d$, $NR^cC(=NOH)NR^cR^d$, $NR^cC(=NCN)NR^cR^d$, $NR^cC(=NR^e)R^b$, $NR^cS(O)NR^cR^d$, $NR^cS(O)R^b$, $NR^cS(O)_2R^b$, $NR^cS(O)(=NR^e)R^b$, $NR^cS(O)_2NR^cR^d$, $S(O)R^b$, $S(O)NR^cR^d$, $S(O)_2R^b$, $S(O)_2NR^cR^d$, $OS(O)(=NR^e)R^b$, $OS(O)_2R^b$, $SF_5$, $P(O)R^fR^g$, $OP(O)(OR^h)(OR^i)$, $P(O)(OR^h)(OR^i)$, and $BR^jR^k$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^A$ substituents;

each $R^a$, $R^b$, $R^c$, and $R^d$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^a$, $R^b$, $R^c$, and $R^d$, are each optionally substituted with 1, 2, 3, or 4 independently selected $R^A$ substituents;

or, any $R^c$ and $R^d$, attached to the same N atom, together with the N atom to which they are attached, form a 5- or 6-membered heteroaryl or a 4-10-membered heterocycloalkyl group, wherein the 5- or 6-membered heteroaryl or 4-10-membered heterocycloalkyl group is optionally substituted with 1, 2, 3, or 4 independently selected $R^A$ substituents;

each $R^e$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^f$ and $R^g$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^h$ and $R^i$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^j$ and $R^k$ is independently selected from OH, $C_{1-6}$ alkoxy, and $C_{1-6}$ haloalkoxy; or any $R^j$ and $R^k$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^A$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a16}$, $SR^{a16}$, $NHOR^{a16}$, $C(O)R^{b16}$, $C(O)NR^{e16}R^{d16}$, $C(O)NR^{c16}(OR^{a16})$, $C(O)OR^{a16}$, $OC(O)R^{b16}$, $OC(O)NR^{c16}R^{d16}$, $NR^{c16}R^{d16}$, $NR^{16}NR^{c16}R^{d16}$, $NR^{a16}C(O)R^{b16}$, $NR^{16}C(O)OR^{a16}$, $NR^{c16}C(O)NR^{c16}R^{d16}$, $C(=NR^{e16})R^{b16}$, $C(=NOH)R^{b16}$, $C(=NCN)R^{b16}$, $C(=NR^{e16})NR^{e16}R^{d16}$, $NR^{e16}C(=NR^{e16})NR^{e16}R^{d16}$, $NR^{c16}C(=NOH)NR^{c16}R^{d16}$, $NR^{c16}C(=NCN)NR^{c16}R^{d16}$, $NR^{16}C(=NR^{e16})R^{b16}$, $NR^{c16}S(O)NR^{e16}R^{d16}$, $NR^{c16}S(O)R^{b16}$, $NR^{c16}S(O)_2R^{b16}$, $NR^{c16}S(O)(=NR^{e16})R^{b16}$, $NR^{c16}S(O)_2NR^{e16}R^{d16}$, $S(O)R^{b16}$, $S(O)NR^{e16}R^{d16}$, $S(O)_2R^{b16}$, $S(O)_2NR^{e16}R^{d16}$, $OS(O)(=NR^{e16})R^{b16}$, $OS(O)_2R^{b16}$, $SF_5$, $P(O)R^{f16}R^{g16}$, $OP(O)(OR^{h16})(OR^{i16})$, $P(O)(OR^{h16})(OR^{i16})$, and $BR^{j16}R^{k16}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents;

each $R^{a16}$, $R^{b16}$, $R^{c16}$, and $R^{d16}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a16}$, $R^{b16}$, $R^{c16}$, and $R^{d16}$, are each optionally substituted with 1, 2, 3, or 4 independently selected $R^B$ substituents;

or, any $R^{c16}$ and $R^{d16}$, attached to the same N atom, together with the N atom to which they are attached, form a 5- or 6-membered heteroaryl or a 4-10-membered heterocycloalkyl group, wherein the 5- or 6-membered heteroaryl or 4-10-membered heterocycloalkyl group is optionally substituted with 1, 2, 3, or 4 independently selected $R^B$ substituents;

each $R^{e16}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f16}$ and $R^{g16}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{h16}$ and $R^{i16}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered hetereocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered hetereocycloalkyl)-$C_{1-6}$ alkyl-;

each $R^{j16}$ and $R^{k16}$ is independently selected from OH, $C_{1-6}$ alkoxy, and $C_{1-6}$ haloalkoxy;

or any $R^{j16}$ and $R^{k16}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^B$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $NO_2$, $OR^{a26}$, $SR^{a26}$, $NHOR^{a26}$, $C(O)R^{b26}$, $C(O)NR^{c26}R^{d26}$, $C(O)NR^{c26}(OR^{a26})$, $C(O)OR^{a26}$, $OC(O)R^{b26}$, $OC(O)NR^{c26}R^{d26}$, $NR^{c26}R^{d26}$, $NR^{c26}NR^{c26}R^{d26}$, $NR^{c26}C(O)R^{b26}$, $NR^{c26}C(O)OR^{a26}$, $NR^{c26}C(O)NR^{c26}R^{d26}$, $C(=NR^{e26})R^{b26}$, $C(=NOH)R^{b26}$, $C(=NCN)R^{b26}$, $C(=NR^{e26})NR^{c26}R^{d26}$, $NR^{c26}C(=NR^{e26})NR^{c26}R^{d26}$, $NR^{c26}C(=NOH)NR^{c26}R^{d26}$, $NR^{c26}C(=NCN)NR^{c26}R^{d26}$, $NR^{c26}C(=NR^{e26})R^{b26}$, $NR^{c26}S(O)NR^{c26}R^{d26}$, $NR^{c26}S(O)R^{b26}$, $NR^{c26}S(O)_2R^{b26}$, $NR^{c26}S(O)(=NR^{e26})R^{b26}$, $NR^{c26}S(O)_2NR^{c26}R^{d26}$, $S(O)R^{b26}$, $S(O)NR^{c26}R^{d26}$, $S(O)_2R^{b26}$, $S(O)_2NR^{c26}R^{d26}$, $OS(O)(=NR^{e26})R^{b26}$, $OS(O)_2R^{b26}$, $SF_5$, $P(O)R^{f26}R^{g26}$, $OP(O)(OR^{h26})(OR^{i26})$, $P(O)(OR^{h26})(OR^{i26})$, and $BR^{j26}R^{k26}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ are each optionally substituted with 1, 2, 3, or 4 independently selected $R^C$ substituents;

each $R^{a26}$, $R^{b26}$, $R^{c26}$, and $R^{d26}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a26}$, $R^{b26}$, $R^{c26}$, and $R^{d26}$, are each optionally substituted with 1, 2, 3, or 4 independently selected $R^C$ substituents;

or, any $R^{c26}$ and $R^{d26}$, attached to the same N atom, together with the N atom to which they are attached, form a 5- or 6-membered heteroaryl or a 4-10-membered heterocycloalkyl group, wherein the 5- or 6-membered heteroaryl or 4-10-membered heterocycloalkyl group is optionally substituted with 1, 2, 3, or 4 independently selected $R^C$ substituents;

each $R^{e26}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f26}$ and $R^{g26}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{h26}$ and $R^{i26}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-;

each $R^{j26}$ and $R^{k26}$ is independently selected from OH, $C_{1-6}$ alkoxy, and $C_{1-6}$ haloalkoxy;

or any $R^{j26}$ and $R^{k26}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^C$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a36}$, $SR^{a36}$, $NHOR^{a36}$, $C(O)R^{b36}$, $C(O)NR^{c36}R^{d36}$, $C(O)NR^{c36}(OR^{a36})$, $C(O)OR^{a36}$, $OC(O)R^{b36}$, $OC(O)NR^{c36}R^{d36}$, $NR^{c36}R^{d36}$, $NR^{c36}NR^{c36}R^{d36}$, $NR^{c36}C(O)R^{b36}$, $NR^{c36}C(O)OR^{a36}$, $NR^{c36}C(O)NR^{c36}R^{d36}$, $C(=NR^{e36})R^{b36}$, $C(=NOH)R^{b36}$, $C(=NCN)R^{b36}$, $C(=NR^{e36})NR^{c36}R^{d36}$, $NR^{c36}C(=NR^{e36})NR^{c36}R^{d36}$, $NR^{c36}C(=NOH)NR^{c36}R^{d36}$, $NR^{c36}C(=NCN)NR^{c36}R^{d36}$, $NR^{c36}C(=NR^{e36})R^{b36}$, $NR^{c36}S(O)NR^{c36}R^{d36}$, $NR^{c36}S(O)R^{b36}$, $NR^{c36}S(O)_2R^{b36}$, $NR^{c36}S(O)(=NR^{e36})R^{b36}$, $NR^{c36}S(O)_2NR^{c36}R^{d36}$, $S(O)R^{b36}$, $S(O)NR^{c36}R^{d36}$, $S(O)_2R^{b36}$, $S(O)_2NR^{c36}R^{d36}$, $OS(O)(=NR^{e36})R^{b36}$, $OS(O)_2R^{b36}$, $SF_5$, $P(O)R^{f36}R^{g36}$, $OP(O)(OR^{h36})(OR^{i36})$, $P(O)(OR^{h36})(OR^{i36})$, and $BR^{j36}R^{k36}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^C$ are each optionally substituted with 1, 2, 3, or 4 independently selected $R^D$ substituents;

each $R^{a36}$, $R^{b36}$, $R^{c36}$, and $R^{d36}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a36}$, $R^{b36}$, $R^{c36}$, and $R^{d36}$, are each optionally substituted with 1, 2, 3, or 4 independently selected $R^D$ substituents;

or, any $R^{c36}$ and $R^{d36}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^D$ substituents;

each $R^{e36}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f36}$ and $R^{g36}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h36}$ and $R^{i36}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$alkyl-, and (4-7 membered heterocycloalkyl)-$C_{1-6}$ alkyl-;

each $R^{j36}$ and $R^{k36}$ is independently selected from OH, $C_{1-6}$ alkoxy, and $C_{1-6}$ haloalkoxy;

or any $R^{j36}$ and $R^{k36}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl;

each $R^D$ is independently selected from halo, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, CN, $NO_2$, $OR^{a46}$, $SR^{a46}$, $NHOR^{a46}$, $C(O)R^{b46}C(O)NR^{c46}R^{d46}$, $C(O)NR^{c46}(OR^{a46})$, $C(O)OR^{a46}$, $OC(O)R^{b46}$, $OC(O)NR^{c46}R^{d46}$, $NR^{c46}R^{d46}$, $NR^{c46}NR^{c46}R^{d46}$, $NR^{c46}C(O)R^{b46}$, $NR^{c46}C(O)OR^{a46}$, $NR^{c46}C(O)NR^{c46}R^{d46}$, $C(=NR^{e46})R^{b46}$, $C(=NOH)R^{b46}$, $C(=NCN)R^{b46}$, $C(=NR^{e46})NR^{c46}R^{d46}$, $NR^{c46}C(=NR^{e46})NR^{c46}R^{d46}$, $NR^{c46}C(=NOH)NR^{c46}R^{d46}$, $NR^{c46}C(=NCN)NR^{c46}R^{d46}$, $NR^{c46}C(=NR^{e46})R^{b46}$, $NR^{c46}S(O)NR^{c46}R^{d46}$, $NR^{c46}S(O)R^{b46}$, $NR^{c46}S(O)_2R^{b46}$, $NR^{c46}S(O)(=NR^{e46})R^{b46}$, $NR^{c46}S(O)_2NR^{c46}R^{d46}$, $S(O)R^{b46}$, $S(O)NR^{c46}R^{d46}$, $S(O)_2R^{b46}$, $S(O)_2NR^{c46}R^{d46}$, $OS(O)(=NR^{e46})R^{b46}$, $OS(O)_2R^{b46}$, $SF_5$, $P(O)R^{f46}R^{g46}$, $OP(O)(OR^{h46})(OR^{i46})$, $P(O)(OR^{h46})(OR^{i46})$, and $BR^{j46}R^{k46}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^D$ are each optionally substituted with 1, 2, 3, or 4 independently selected $R^E$ substituents;

each $R^{a46}$, $R^{b46}$, $R^{c46}$, and $R^{d46}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a46}$, $R^{b46}$, $R^{c46}$, and $R^{d46}$, are each optionally substituted with 1, 2, 3, or 4 independently selected $R^E$ substituents;

or, any $R^{c46}$ and $R^{d46}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^E$ substituents;

each $R^{e46}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{f46}$ and $R^{g46}$ is independently selected from H, $C_{1-6}$ alkyl, $C_{1-6}$ alkoxy, $C_{1-6}$ haloalkyl, $C_{1-6}$ haloalkoxy, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-;

each $R^{h46}$ and $R^{i46}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$alkyl-, and (4-7 membered heterocycloalkyl)-$C_{1-6}$ alkyl-;

each $R^{j46}$ and $R^{k46}$ is independently selected from OH, $C_{1-6}$ alkoxy, and $C_{1-6}$ haloalkoxy;

or any $R^{j46}$ and $R^{k46}$ attached to the same B atom, together with the B atom to which they are attached, form a 5- or 6-membered heterocycloalkyl group optionally substituted with 1, 2, 3, or 4 substituents independently selected from $C_{1-6}$ alkyl and $C_{1-6}$ haloalkyl; and each $R^E$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkoxycarbonylamino, $C_{1-3}$ alkylcarbonyloxy, aminocarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

wherein 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-6}$ alkyl-" linking groups, are optionally replaced by deuterium atoms.

In some embodiments:

$X^1$ is $CR^1$ or N;

$R^1$ is H, $C_{1-6}$ alkyl or $C_{1-6}$ haloalkyl;

$R^2$ is selected from H, D, halo, $C_{1-6}$ alkyl, $C_{1-6}$ haloalkyl, $C_{2-6}$ alkenyl, $C_{2-6}$ alkynyl, CN, $OR^{a2}$, $NHOR^{a2}$, $C(O)R^{b2}$, $C(O)NR^{c2}R^{d2}$, $C(O)NR^{c2}(OR^{a2})$, $C(O)OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl of $R^2$ are each optionally substituted with 1, 2, 3, or 4 independently selected $R^{2A}$ substituents;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, and $C_{2-6}$ alkynyl wherein the $C_{1-6}$ alkyl, $C_{2-6}$ alkenyl, and $C_{2-6}$ alkynyl of $R^{a2}$, $R^{b2}$, $R^{c2}$, and $R^{d2}$ are each optionally substituted with 1, 2, 3, or 4 independently selected $R^{2A}$ substituents;

each $R^{2A}$ is independently selected from D, OH, CN, halo, $C_{1-3}$ alkyl, $C_{2-3}$ alkenyl, $C_{2-3}$ alkynyl, $C_{1-3}$ haloalkyl, $C_{1-3}$ alkoxy, $C_{1-3}$ haloalkoxy, amino, $C_{1-3}$ alkylamino, and di($C_{1-3}$ alkyl)amino;

$R^3$ is selected from H, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, (4-7 membered heterocycloalkyl)-$C_{1-6}$ alkyl-, $C(O)R^{b3}$, $C(O)NR^{c3}R^{d3}$, $C(O)OR^{a3}$, $C(=NR^{e3})R^{b3}$, $C(=NR^{e3})NR^{c3}R^{d3}$, $S(O)_2R^{b3}$, and $S(O)_2NR^{c3}R^{d3}$, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^3$ are each optionally substituted with 1, 2, 3, or 4 independently selected $R^{3A}$ substituents;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl-, wherein the $C_{1-6}$ alkyl, $C_{2-6}$ alkenyl, $C_{2-6}$ alkynyl, phenyl, $C_{3-7}$ cycloalkyl, 5-6 membered heteroaryl, 4-7 membered heterocycloalkyl, phenyl-$C_{1-6}$ alkyl-, $C_{3-7}$ cycloalkyl-$C_{1-6}$ alkyl-, (5-6 membered heteroaryl)-$C_{1-6}$ alkyl-, and (4-7 membered heterocycloalkyl)-$C_{1-6}$ alkyl- of $R^{a3}$, $R^{b3}$, $R^{c3}$, and $R^{d3}$, are each optionally substituted with 1, 2, 3, or 4 independently selected $R^{3A}$ substituents;

or, any $R^{c3}$ and $R^{d3}$, attached to the same N atom, together with the N atom to which they are attached, form a 5- or 6-membered heteroaryl or a 4-, 5-, 6-, or 7-membered heterocycloalkyl group, wherein the 5- or 6-membered heteroaryl or 4-, 5-, 6-, or 7-membered heterocycloalkyl group is optionally substituted with 1, 2, 3, or 4 independently selected $R^{3A}$ substituents;

each $R^{e3}$ is independently selected from H, OH, CN, $C_{1-6}$ alkyl, $C_{1-6}$ alkoxy, $C_{1-6}$ haloalkyl, $C_{1-6}$ haloalkoxy, $C_{2-6}$ alkenyl, and $C_{2-6}$ alkynyl;

each $R^{3A}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylcarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

$R^4$ is selected from H, $C_{1-6}$ alkyl, or $C_{1-6}$ haloalkyl;

$R^5$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^a$, $C(O)R^b$, $C(O)NR^cR^d$, $C(O)NR^c(OR^a)$, $C(O)OR^a$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)R^b$, $S(O)_2R^b$, and $S(O)_2NR^cR^d$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are each optionally substituted with 1, 2, 3, or 4 independently selected $R^A$ substituents;

$R^6$ is selected from H, D, halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^a$, $C(O)R^b$, $C(O)NR^cR^d$, $C(O)NR^c(OR^a)$, $C(O)OR^a$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)R^b$, $S(O)_2R^b$, and $S(O)_2NR^cR^d$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are each optionally substituted with 1, 2, 3, or 4 independently selected $R^A$ substituents;

each $R^A$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a16}$, $SR^{a16}$, $NHOR^{a16}$, $C(O)R^{b16}$, $C(O)NR^{c16}R^{d16}$, $C(O)NR^{c16}(OR^{a16})$, $C(O)OR^{a16}$, $OC(O)R^{b16}$, $OC(O)NR^{c16}R^{d16}$, $NR^{c16}R^{d16}$, $NR^{c16}C(O)R^{b16}$ $NR^{c16}C(O)OR^{a16}$, $NR^{c16}C(O)NR^{c16}R^{d16}$, $NR^{c16}S(O)_2R^{b16}$, $NR^{c16}S(O)_2NR^{c16}R^{d16}$, $S(O)_2R^{b16}$, and $S(O)_2NR^{c16}R^{d16}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents;

each $R^{a16}$, $R^{b16}$, $R^{c16}$, and $R^{d16}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a16}$, $R^{b16}$, $R^{c16}$, and $R^{d16}$, are each optionally substituted with 1, 2, 3, or 4 independently selected $R^B$ substituents;

each $R^B$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a26}$, $SR^{a26}$, $NHOR^{a26}$, $C(O)R^{b26}$, $C(O)NR^{c26}R^{d26}$, $C(O)OR^{a26}$, $OC(O)R^{b26}$, $OC(O)NR^{c26}R^{d26}$, $NR^{c26}R^{d26}$, $NR^{c26}C(O)R^{b26}$, $NR^{c26}C(O)OR^{a26}$, $NR^{c26}C(O)NR^{c26}R^{d26}$, $NR^{c26}S(O)_2R^{b26}$, $NR^{c26}S(O)_2NR^{c26}R^{d26}$, $S(O)_2R^{b26}$, and $S(O)_2NR^{c26}R^{d26}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ are each optionally substituted with 1, 2, 3, or 4 independently selected $R^C$ substituents;

each $R^{a26}$, $R^{b26}$, $R^{c26}$, and $R^{d26}$ is independently selected from H, $C_{1-6}$ alkyl, and $C_{1-6}$ haloalkyl, wherein the $C_{1-6}$ alkyl of $R^{a26}$, $R^{b26}$, $R^{c26}$, and $R^{d26}$ are each optionally substituted with 1, 2, 3, or 4 independently selected $R^C$ substituents;

each $R^C$ is independently selected from halo, $C_{1-6}$ alkyl, $C_{1-6}$ haloalkyl, $C_{2-6}$ alkenyl, $C_{2-6}$ alkynyl, CN, $OR^{a36}$, $SR^{a36}$, $NHOR^{a36}$, $C(O)R^{b36}$, $C(O)NR^{c36}R^{d36}$, $C(O)OR^{a36}$, $OC(O)R^{b36}$, $OC(O)NR^{c36}R^{d36}$, $NR^{c36}R^{d36}$, $NR^{c36}C(O)R^{b36}$, $NR^{c36}C(O)OR^{a36}$, $NR^{c36}C(O)NR^{c36}R^{d36}$, $NR^{c36}S(O)_2R^{b36}$, $NR^{c36}S(O)_2NR^{c36}R^{d36}$, $S(O)_2R^{b36}$, and $S(O)_2NR^{c36}R^{d36}$, wherein the $C_{1-6}$ alkyl, $C_{2-6}$ alkenyl, and $C_{2-6}$ alkynyl of $R^C$ are each optionally substituted with 1, 2, 3, or 4 independently selected $R^D$ substituents; and each $R^{a36}$, $R^{b36}$, $R^{c36}$, and $R^{d36}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{a36}$, $R^{b36}$, $R^{c36}$, and $R^{d36}$ are each optionally substituted with 1, 2, 3, or 4 independently selected $R^D$ substituents; and each $R^D$ is independently selected from OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylcarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

wherein 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-6}$ alkyl-" linking groups, are optionally replaced by deuterium atoms.

In some embodiments:

$X^1$ is $CR^1$ or N;

$R^1$ is H;

$R^2$ is selected from H, $C_{1-6}$ alkyl, and $C_{1-6}$ haloalkyl;

$R^3$ is selected from H, $C_{1-6}$ alkyl, and $C_{1-6}$ haloalkyl;

$R^4$ is H;

$R^5$ is selected from H, D, halo, CN, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein said $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are optionally substituted by 1, 2, 3, or 4 independently selected $R^A$ substituents;

$R^6$ is selected from H, D, halo, CN, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein said $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are optionally substituted by 1, 2, 3, or 4 independently selected $R^A$ substituents;

each $R^A$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a16}$, $SR^{a16}$, $NHOR^{a16}$, $C(O)R^{b16}$, $C(O)NR^{c16}R^{d16}$, $C(O)NR^{c16}(OR^{a16})$, $C(O)OR^{a16}$, $OC(O)R^{b16}$, $OC(O)NR^{c16}R^{d16}$, $NR^{c16}R^{d16}$, $NR^{c16}C(O)R^{b16}$, $NR^{c16}C(O)OR^{a16}$, $NR^{c16}C(O)NR^{c16}R^{d16}$, $NR^{c16}S(O)_2R^{b16}$, $NR^{c16}S(O)_2NR^{c16}R^{d16}$, $S(O)_2R^{b16}$, and $S(O)_2NR^{c16}R^{d16}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents;

each $R^{a16}$, $R^{b16}$, $R^{c16}$, and $R^{d16}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^{a16}$, $R^{b16}$, $R^{c16}$, and $R^{d16}$, are each optionally substituted with 1, 2, 3, or 4 independently selected $R^B$ substituents;

each $R^B$ is independently selected from halo, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, (4-10 membered heterocycloalkyl)-$C_{1-6}$ alkyl-, CN, $OR^{a26}$, $SR^{a26}$, $NHOR^{a26}$, $C(O)R^{b26}$, $C(O)NR^{c26}R^{d26}$, $C(O)OR^{a26}$, $OC(O)R^{b26}$, $OC(O)NR^{c26}R^{d26}$, $NR^{c26}R^{d26}$, $NR^{c26}C(O)R^{b26}$, $NR^{c26}C(O)OR^{a26}$, $NR^{c26}C(O)NR^{c26}R^{d26}$, $NR^{c26}S(O)_2R^{b26}$, $NR^{c26}S(O)_2NR^{c26}R^{d26}$, $S(O)_2R^{b26}$, and $S(O)_2NR^{c26}R^{d26}$, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^B$ are each optionally substituted with 1, 2, 3, or 4 independently selected $R^C$ substituents;

each $R^{a26}$, $R^{b26}$, $R^{c26}$, and $R^{d26}$ is independently selected from H, $C_{1-6}$ alkyl, and $C_{1-6}$ haloalkyl, wherein the $C_{1-6}$ alkyl of $R^{a26}$, $R^{b26}$, $R^{c26}$, and $R^{d26}$ are each optionally substituted with 1, 2, 3, or 4 independently selected $R^C$ substituents;

each $R^C$ is independently selected from halo, $C_{1-6}$ alkyl, $C_{1-6}$ haloalkyl, $C_{2-6}$ alkenyl, $C_{2-6}$ alkynyl, CN, $OR^{a36}$, $SR^{a36}$, $NHOR^{a36}$, $C(O)R^{b36}$, $C(O)NR^{c36}R^{d36}$, $C(O)OR^{a36}$, $OC(O)R^{b36}$, $OC(O)NR^{c36}R^{d36}$, $NR^{c36}R^{d36}$, $NR^{c36}C(O)R^{b36}$, $NR^{c36}C(O)OR^{a36}$, $NR^{c36}C(O)NR^{c36}R^{d36}$, $NR^{c36}S(O)_2R^{b36}$, $NR^{c36}S(O)_2NR^{c36}R^{d36}$, $S(O)_2R^{b36}$, and $S(O)_2NR^{c36}R^{d36}$, wherein the $C_{1-6}$ alkyl, $C_{2-6}$ alkenyl, and $C_{2-6}$ alkynyl of $R^C$ are each optionally substituted with 1, 2, 3, or 4 independently selected $R^D$ substituents; and each $R^{a36}$, $R^{b36}$, $R^{c36}$, and $R^{d36}$ is independently selected from H, $C_{1-6}$ alkyl, $C_{1-6}$ haloalkyl, $C_{2-6}$ alkenyl, and $C_{2-6}$ alkynyl, wherein the $C_{1-6}$ alkyl, $C_{2-6}$ alkenyl, and $C_{2-6}$ alkynyl of $R^{a36}$, $R^{b36}$, $R^{c36}$, and $R^{d36}$ are each optionally substituted with 1, 2, 3, or 4 independently selected $R^D$ substituents; and each $R^D$ is independently selected from OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylcarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

wherein 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-6}$ alkyl-" linking groups, are optionally replaced by deuterium atoms.

In some embodiments:

$X^1$ is $CR^1$ or N;

$R^1$ is H;

$R^2$ is selected from H, $C_{1-6}$ alkyl, and $C_{1-6}$ haloalkyl;

$R^3$ is selected from H, $C_{1-6}$ alkyl, and $C_{1-6}$ haloalkyl;

$R^4$ is H;

$R^5$ is selected from H, D, halo, CN, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein said $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^5$ are optionally substituted by 1, 2, 3, or 4 independently selected $R^A$ substituents;

$R^6$ is selected from H, D, halo, CN, $C_{1-6}$ alkyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl-, wherein said $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl-, $C_{3-10}$ cycloalkyl-$C_{1-6}$ alkyl-, (5-10 membered heteroaryl)-$C_{1-6}$ alkyl-, and (4-10 membered heterocycloalkyl)-$C_{1-6}$ alkyl- of $R^6$ are optionally substituted by 1, 2, 3, or 4 independently selected $R^A$ substituents;

each $R^A$ is independently selected from (5-10 membered heteroaryl)-$C_{1-6}$ alkyl-, (4-10 membered heterocycloalkyl)-$C_{1-6}$ alkyl-, and $S(O)_2NR^{c16}R^{d16}$, wherein the (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents; and each $R^{c16}$ and $R^{d16}$ is independently selected from H and $C_{6-10}$ aryl, wherein the $C_{6-10}$ aryl of $R^{c16}$ and $R^{d16}$ is optionally substituted with 1, 2, 3, or 4 independently selected $R^B$ substituents;

each $R^B$ is independently selected from halo, $C_{1-6}$ alkyl, 5-10 membered heteroaryl, $C(O)R^{b26}$, and $C(O)NR^{c26}R^{d26}$, wherein the 5-10 membered heteroaryl of $R^B$ are each optionally substituted with 1, 2, 3, or 4 independently selected $R^C$ substituents;

each $R^{b26}$, $R^{c26}$, and $R^{d26}$ is independently selected from H and $C_{1-6}$ alkyl, wherein the $C_{1-6}$ alkyl of $R^{b26}$, $R^{c26}$, and $R^{d26}$ are each optionally substituted with 1, 2, 3, or 4 independently selected $R^C$ substituents;

each $R^C$ is independently selected from halo, $C_{1-6}$ alkyl, CN, $OR^{a36}$, and $NR^{c36}R^{d36}$, wherein the $C_{1-6}$ alkyl of $R^C$ are each optionally substituted with 1, 2, 3, or 4 independently selected $R^D$ substituents; and each $R^{a36}$, $R^{c36}$, and $R^{d36}$ is independently selected from H, $C_{1-6}$ alkyl, wherein the $C_{1-6}$ alkyl of $R^{a36}$, $R^{c36}$, and $R^{d36}$ is optionally substituted with 1, 2, 3, or 4 independently selected $R^D$ substituents; and each $R^D$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylcarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

wherein 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-6}$ alkyl-" linking groups, are optionally replaced by deuterium atoms.

In some embodiments:

$X^1$ is $CR^1$ or N;

$R^1$ is H;

$R^2$ is selected from $C_{1-6}$ alkyl and $C_{1-6}$ haloalkyl;

$R^3$ is $C_{1-6}$ alkyl;

$R^4$ is H;

$R^5$ is selected from H, D, halo, CN, $C_{1-6}$ alkyl, $C_{6-10}$ aryl, and (5-10 membered heteroaryl)-$C_{1-6}$ alkyl-, wherein said $C_{6-10}$ aryl and (5-10 membered heteroaryl)-$C_{1-6}$ alkyl- of $R^5$ are optionally substituted by 1, 2, 3, or 4 independently selected $R^A$ substituents;

$R^6$ is selected from H, $C_{6-10}$ aryl and (5-10 membered heteroaryl)-$C_{1-6}$ alkyl-, wherein said $C_{6-10}$ aryl and (5-10 membered heteroaryl)-$C_{1-6}$ alkyl- of $R^6$ are optionally substituted by 1, 2, 3, or 4 independently selected $R^A$ substituents;

each $R^A$ is independently selected from (5-10 membered heteroaryl)-$C_{1-6}$ alkyl-, (4-10 membered heterocycloalkyl)-$C_{1-6}$ alkyl-, and $S(O)_2NR^{c16}R^{d16}$, wherein the (5-10 membered heteroaryl)-$C_{1-6}$ alkyl-, and (4-10 membered heterocycloalkyl)-$C_{1-6}$ alkyl- of $R^A$ are each optionally substituted with 1, 2, 3, or 4 independently selected $R^B$ substituents; and each $R^{c16}$ and $R^{d16}$ is independently selected from H and $C_{6-10}$ aryl, wherein the $C_{6-10}$ aryl of $R^{c16}$ and $R^{d16}$ is optionally substituted with 1, 2, 3, or 4 independently selected $R^B$ substituents;

each $R^B$ is independently selected from halo, $C_{1-6}$ alkyl, 5-10 membered heteroaryl, $C(O)R^{b26}$, and $C(O)NR^{c26}R^{d26}$, wherein the 5-10 membered heteroaryl of $R^B$ are each optionally substituted with 1, 2, 3, or 4 independently selected $R^C$ substituents;

each $R^{b26}$, $R^{c26}$, and $R^{d26}$ is independently selected from H and $C_{1-6}$ alkyl, wherein the $C_{1-6}$ alkyl of $R^{b26}$, $R^{c26}$, and $R^{d26}$ are each optionally substituted with 1, 2, 3, or 4 independently selected $R^C$ substituents;

each $R^C$ is independently selected from halo, $C_{1-6}$ alkyl, CN, $OR^{a36}$, and $NR^{c36}R^{d36}$, wherein the $C_{1-6}$ alkyl of $R^C$ are each optionally substituted with 1, 2, 3, or 4 independently selected $R^D$ substituents; and each $R^{a36}$, $R^{c36}$, and $R^{d36}$ is independently selected from H, $C_{1-6}$ alkyl, wherein the $C_{1-6}$ alkyl of $R^{a36}$, $R^{c36}$, and $R^{d36}$ is optionally substituted with 1, 2, 3, or 4 independently selected $R^D$ substituents; and each $R^D$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-5}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylcarbonyloxy, $C_{1-3}$ alkylaminocarbonyloxy, di($C_{1-3}$ alkyl)aminocarbonyloxy, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

wherein 1, 2, 3, 4, 5, 6, 7, or 8 hydrogen atoms, attached to carbon atoms of "alkyl", "alkenyl", "alkynyl", "aryl", "phenyl", "cycloalkyl", "heterocycloalkyl", or "heteroaryl" substituents or "—$C_{1-6}$ alkyl-" linking groups, are optionally replaced by deuterium atoms.

In some embodiments, the compound is a compound of Formula (II):

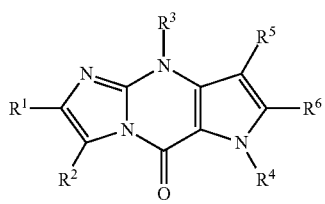

or a pharmaceutically acceptable salt thereof.

In some embodiments, the compound is a compound of Formula (III):

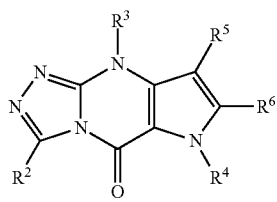

or a pharmaceutically acceptable salt thereof.

In some embodiments, only one of $R^5$ and $R^6$ contains cyclic groups.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

As used herein, the phrase "each 'variable' is independently selected from" means substantially the same as wherein "at each occurrence 'variable' is selected from."

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl (Me), ethyl (Et), n-propyl (n-Pr), isopropyl (iPr), n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms. As used herein, the term "$C_{n-m}$ alkoxy", employed alone or in combination with other terms, refers to a group of formula-O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "amino" refers to a group of formula —$NH_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, the aryl group has from 5 to 10 carbon atoms. In some embodiments, the aryl group is phenyl or naphthyl. In some embodiments, the aryl is phenyl.

As used herein, "halo" refers to F, Cl, Br, or I. In some embodiments, halo is F, Cl, or Br. In some embodiments, halo is F or Cl. In some embodiments, halo is F. In some embodiments, halo is Cl.

As used herein, "$C_{n-m}$ haloalkoxy" refers to a group of formula —O-haloalkyl having n to m carbon atoms. Example haloalkoxy groups include $OCF_3$ and $OCHF_2$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms. Example haloalkyl groups include $CF_3$, $C_2F_5$, $CHF_2$, $CH_2F$, $CCl_3$, $CHCl_2$, $C_2Cl_5$ and the like.

As used herein, the term "thio" refers to a group of formula —SH.

As used herein, the term "carbamyl" to a group of formula —C(O)NH$_2$.

As used herein, the term "carbonyl", employed alone or in combination with other terms, refers to a —C(O)— group.

As used herein, the term "C$_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "C$_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "C$_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "C$_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "C$_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di(C$_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "C$_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "C$_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "C$_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "cyano-C$_{1-6}$ alkyl" refers to a group of formula —(C$_{1-6}$ alkylene)-CN.

As used herein, the term "HO—C$_{1-6}$ alkyl" refers to a group of formula —(C$_{1-6}$ alkylene)-OH.

As used herein, the term "C$_{1-6}$ alkoxy-C$_{1-6}$ alkyl" refers to a group of formula —(C$_{1-6}$ alkylene)-O(C$_{1-6}$ alkyl).

As used herein, the term "carboxy" refers to a group of formula —C(O)OH.

As used herein, the term "di(C$_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di(C$_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "C$_{n-m}$ alkylcarbonyloxy" is a group of formula —OC(O)-alkyl, wherein the alkyl group has n to m carbon atoms.

As used herein, "aminocarbonyloxy" is a group of formula —OC(O)—NH$_2$.

As used herein, "C$_{n-m}$ alkylaminocarbonyloxy" is a group of formula —OC(O)—NH-alkyl, wherein the alkyl group has n to m carbon atoms.

As used herein, "di(C$_{n-m}$ alkyl)aminocarbonyloxy" is a group of formula —OC(O)—N(alkyl)$_2$, wherein each alkyl group has, independently, n to m carbon atoms.

As used herein C$_{n-m}$ alkoxycarbonylamino refers to a group of formula —NHC(O)—O-alkyl, wherein the alkyl group has n to m carbon atoms.

As used herein, "cycloalkyl" refers to non-aromatic cyclic hydrocarbons including cyclized alkyl and alkenyl groups. Cycloalkyl groups can include mono- or polycyclic (e.g., having 2, 3 or 4 fused rings) groups, spirocycles, and bridged rings (e.g., a bridged bicycloalkyl group). Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, 12, 13, or 14 ring-forming carbons (i.e., C$_{3-14}$). In some embodiments, the cycloalkyl is a C$_{3-14}$ monocyclic or bicyclic cycloalkyl. In some embodiments, the cycloalkyl is a C$_{3-7}$ monocyclic cycloalkyl. In some embodiments, the cycloalkyl is a C$_{4-7}$ monocyclic cycloalkyl. In some embodiments, the cycloalkyl is a C$_{4-10}$ spirocycle or bridged cycloalkyl (e.g., a bridged bicycloalkyl group). Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cubane, adamantane, bicyclo[1.1.1]pentyl, bicyclo[2.1.1]hexyl, bicyclo[2.2.1]heptanyl, bicyclo[3.1.1]heptanyl, bicyclo [2.2.2]octanyl, spiro[3.3]heptanyl, and the like. In some embodiments, cycloalkyl is cyclopropyl, cyclobutyl, cyclopentyl, or cyclohexyl.

As used herein, "heteroaryl" refers to a monocyclic or polycyclic (e.g., having 2, 3, or 4 fused rings) aromatic heterocycle having at least one heteroatom ring member selected from N, O, S and B. In some embodiments, the heteroaryl ring has 1, 2, 3, or 4 heteroatom ring members independently selected from N, O, S and B. In some embodiments, any ring-forming N in a heteroaryl moiety can be an N-oxide. In some embodiments, the heteroaryl is a 5-10 membered monocyclic or bicyclic heteroaryl having 1, 2, 3, or 4 heteroatom ring members independently selected from N, O, S, and B. In some embodiments, the heteroaryl is a 5-10 membered monocyclic or bicyclic heteroaryl having 1, 2, 3, or 4 heteroatom ring members independently selected from N, O, S and B. In some embodiments, the heteroaryl is a 5-10 membered monocyclic or bicyclic heteroaryl having 1, 2, 3, or 4 heteroatom ring members independently selected from N, O, and S. In some embodiments, the heteroaryl is a 5-6 monocyclic heteroaryl having 1 or 2 heteroatom ring members independently selected from N, O, S and B. In some embodiments, the heteroaryl is a 5-6 monocyclic heteroaryl having 1 or 2 heteroatom ring members independently selected from N, O, and S. In some embodiments, the heteroaryl group contains 5-10 or 5-6 ring-forming atoms. In some embodiments, the heteroaryl group has 1 to 4 ring-forming heteroatoms, 1 to 3 ring-forming heteroatoms, 1 to 2 ring-forming heteroatoms or 1 ring-forming heteroatom. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine, thieno[3,2-b]pyridine, imidazo[1,2-a]pyridine, 1,5-naphthyridine, 1H-pyrazolo[4,3-b]pyridine, and the like.

A five-membered heteroaryl is a heteroaryl group having five ring-forming atoms wherein one or more (e.g., 1, 2, or 3) of the ring-forming atoms are independently selected from N, O, S or B. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl and 1,2-dihydro-1,2-azaborine.

A six-membered heteroaryl ring is a heteroaryl with a ring having six ring atoms wherein one or more (e.g., 1, 2, or 3) ring atoms are independently selected from N, O, S and B. Exemplary six-membered ring heteroaryls are pyridyl, pyrazinyl, pyrimidinyl, triazinyl and pyridazinyl.

As used herein, "heterocycloalkyl" refers to monocyclic or polycyclic heterocycles having at least one non-aromatic ring (saturated or partially unsaturated ring), wherein one or more of the ring-forming carbon atoms of the heterocycloalkyl is replaced by a heteroatom selected from N, O, S and B, wherein the ring-forming carbon atoms and heteroatoms of a heterocycloalkyl group can be optionally substituted by one or more oxo or sulfido (e.g., C(O), S(O), C(S), or S(O)$_2$, etc.). Heterocycloalkyl groups include monocyclic and polycyclic (e.g., having 2, 3 or 4 fused rings) systems. Included in heterocycloalkyl are monocyclic and polycyclic 3-14 or 4-14 membered heterocycloalkyl groups. Heterocycloalkyl groups can also include spirocycles and bridged rings (e.g., a 5-14 membered bridged biheterocycloalkyl ring having one or more of the ring-forming carbon atoms replaced by a heteroatom selected from N, O, S and B). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the non-aromatic heterocyclic ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group contains 3 to 14 ring-forming atoms, 4 to 14 ring-forming atoms, 3 to 7 ring-forming atoms, or 5 to 6 ring-forming atoms. In some embodiments, the heterocycloalkyl group has 1 to 4 heteroatoms, 1 to 3 heteroatoms, 1 to 2 heteroatoms or 1 heteroatom. In some embodiments, the heterocycloalkyl is a monocyclic 4-6 membered heterocycloalkyl having 1 or 2 heteroatoms independently selected from N, O, S and B and having one or more oxidized ring members.

In some embodiments, the heterocycloalkyl is a monocyclic or bicyclic 5-10 membered heterocycloalkyl having 1, 2, 3, or 4 heteroatoms independently selected from N, O, S and B and having one or more oxidized ring members. In some embodiments, the heterocycloalkyl is a monocyclic or bicyclic 5-10 membered heterocycloalkyl having 1, 2, 3, or 4 heteroatoms independently selected from N, O, and S and having one or more oxidized ring members. In some embodiments, the heterocycloalkyl is a monocyclic 5-6 membered heterocycloalkyl having 1, 2, 3, or 4 heteroatoms independently selected from N, O, and S and having one or more oxidized ring members. Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, azabicyclo[3.1.0]hexanyl, diazabicyclo[3.1.0]hexanyl, oxabicyclo[2.1.1]hexanyl, azabicyclo[2.2.1]heptanyl, diazabicyclo[2.2.1]heptanyl, azabicyclo[3.1.1]heptanyl, diazabicyclo[3.1.1]heptanyl, azabicyclo[3.2.1]octanyl, diazabicyclo[3.2.1]octanyl, oxabicyclo[2.2.2]octanyl, azabicyclo[2.2.2]octanyl, azaadamantanyl, diazaadamantanyl, oxa-adamantanyl, azaspiro[3.3]heptanyl, diazaspiro[3.3]heptanyl, oxa-azaspiro[3.3]heptanyl, azaspiro[3.4]octanyl, diazaspiro[3.4]octanyl, oxa-azaspiro[3.4]octanyl, azaspiro[2.5]octanyl, diazaspiro[2.5]octanyl, azaspiro[4.4]nonanyl, diazaspiro[4.4]nonanyl, oxa-azaspiro[4.4]nonanyl, azaspiro[4.5]decanyl, diazaspiro[4.5]decanyl, diazaspiro[4.4]nonanyl, oxa-diazaspiro[4.4]nonanyl and the like. In some embodiments, example heterocycloalkyl group are pyrrolidonyl, pyrrolidin-2-one, 1,3-isoxazolidin-2-one, pyranyl, tetrahydropuran, oxetanyl, azetidinyl, morpholinyl, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, and 1,2,3,4-tetrahydroisoquinoline.

As used herein, "$C_{o-p}$ cycloalkyl-$C_{n-m}$ alkyl-" refers to a group of formula cycloalkyl-alkylene-, wherein the cycloalkyl has o to p carbon atoms and the alkylene linking group has n to m carbon atoms.

As used herein "$C_{o-p}$ aryl-$C_{n-m}$ alkyl-" refers to a group of formula aryl-alkylene-, wherein the aryl has o to p carbon atoms and the alkylene linking group has n to m carbon atoms.

As used herein, "heteroaryl-$C_{n-m}$ alkyl-" refers to a group of formula heteroaryl-alkylene-, wherein alkylene linking group has n to m carbon atoms.

As used herein "heterocycloalkyl-$C_{n-m}$ alkyl-" refers to a group of formula heterocycloalkyl-alkylene-, wherein alkylene linking group has n to m carbon atoms.

As used herein, an "alkyl linking group" is a bivalent straight chain or branched alkyl linking group ("alkylene group"). For example, "$C_{o-p}$ cycloalkyl-$C_{n-m}$ alkyl-", "$C_{o-p}$ aryl-$C_{n-m}$ alkyl-", "phenyl-$C_{n-m}$ alkyl-", "heteroaryl-$C_{n-m}$ alkyl-", and "heterocycloalkyl-$C_{n-m}$ alkyl-" contain alkyl linking groups. Examples of "alkyl linking groups" or "alkylene groups" include methylene, ethan-1,1-diyl, ethan-1,2-diyl, propan-1,3-diyl, propan-1,2-diyl, propan-1,1-diyl and the like.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom (i.e., =O) as a divalent substituent, forming a carbonyl group when attached to a carbon (e.g., C=O or C(O)), or attached to a nitrogen or sulfur heteroatom forming a nitroso, sulfinyl or sulfonyl group.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present disclosure are described and may be isolated as a mixture of isomers or as separated isomeric forms. In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, 2-hydroxypyridine and 2-pyridone, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein.

Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

As will be appreciated, the compounds provided herein, including salts and stereoisomers thereof, can be prepared using known organic synthesis techniques and can be synthesized according to any of numerous possible synthetic routes.

A compound of formula 10 can be prepared using the synthetic route outlined in Scheme 1. Commercially available ethyl 3-amino-1H-pyrrole-2-carboxylate (1) is subjected to chemical transformations, such as reductive amination with an aldehyde containing $R^3$, to afford compound 2. Condensation of compound 2 with ethoxycarbonyl isothiocyanate, followed by treatment with ethanolic sodium ethoxide at elevated temperature, affords bicyclic compound 3. Compound 3 is treated with hydrazine hydrate at elevated temperature to afford bicyclic compound 4. Compound 4 is reacted with an adduct of formula 5 or 6 at elevated temperature to afford compound 7. Compound 7 is first activated by treatment with benzenesulfonyl chloride and suitable bases, such as triethylamine and 4-dimethylaminopyridine, to afford adduct 7a. The phenylsulfone intermediate 7a is subjected to deprotonation using a strong non-nucleophilic base, such as lithium isopropylamide, and then halogenation with an appropriate reagent, such as 1,2-dibromo-1,1,2,2-tetrachloroethane, to furnish compound 8 (Hal is a halide, such as F, Cl, Br, or I). Compound 8 is coupled to an adduct of formula 9, in which M is a boronic acid, a boronic ester or an appropriately substituted metal [e.g., M is $B(OR)_2$, $Sn(alkyl)_3$, Zn-Hal, etc.], under standard Suzuki cross-coupling conditions (e.g., in the presence of a palladium catalyst and a suitable base), or standard Stille cross-coupling conditions (e.g. in the presence of a palladium catalyst) or standard Negishi cross-coupling conditions (e.g. in the presence of a palladium catalyst). The phenylsulfonyl group is then removed under basic conditions, such as sodium hydroxide, to afford a derivative of formula 10. Alternatively, compound 8 can first be treated with an appropriate reagent, such as tetrabutylammonium fluoride, to facilitate the removal of the phenylsulfonyl group prior to cross-coupling; the resulting intermediate is then coupled to an adduct of formula 9, as described above, to furnish a derivative of formula 10.

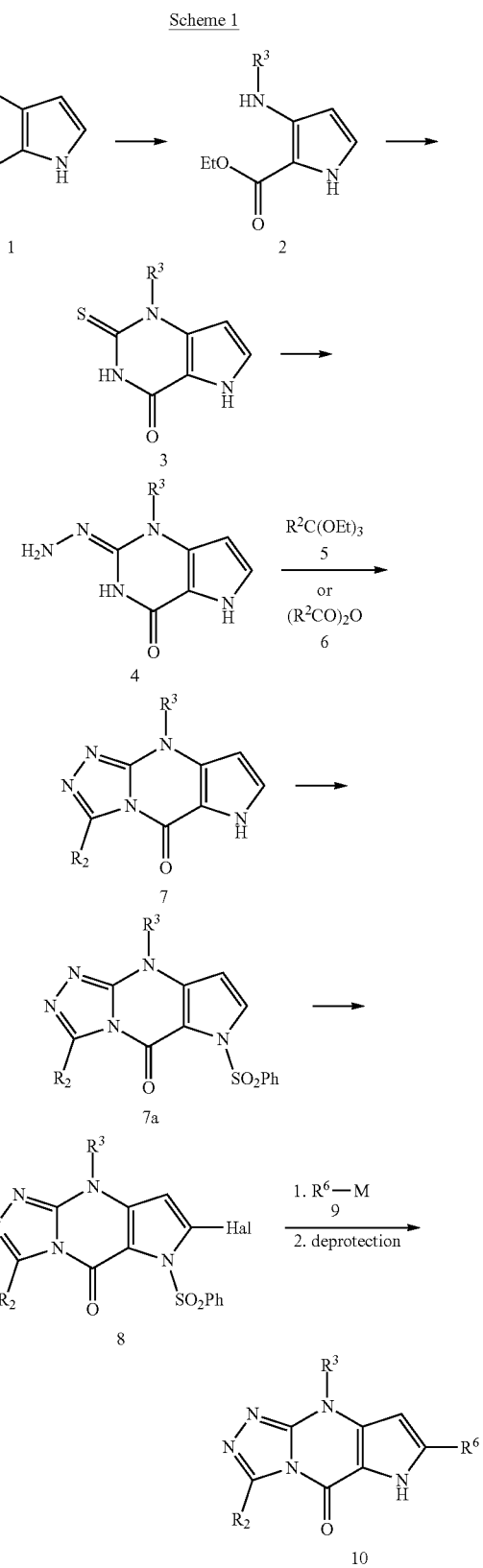

A compound of formula 13 can be prepared using the synthetic route outlined in Scheme 2. Compound 7 (prepared according to Scheme 1) is subjected to halogenation with an appropriate reagent, such as N-bromosuccinimide, to afford compound 11 (Hal is a halide, such as F, Cl, Br, or I). Compound 11 is coupled to an adduct of formula 12, in which M is a boronic acid, a boronic ester or an appropriately substituted metal [e.g., M is B(OR)$_2$, Sn(alkyl)$_3$, Zn-Hal, etc.], under standard Suzuki cross-coupling conditions (e.g., in the presence of a palladium catalyst and a suitable base), or standard Stille cross-coupling conditions (e.g. in the presence of a palladium catalyst) or standard Negishi cross-coupling conditions (e.g. in the presence of a palladium catalyst), to furnish a derivative of formula 13.

Scheme 2

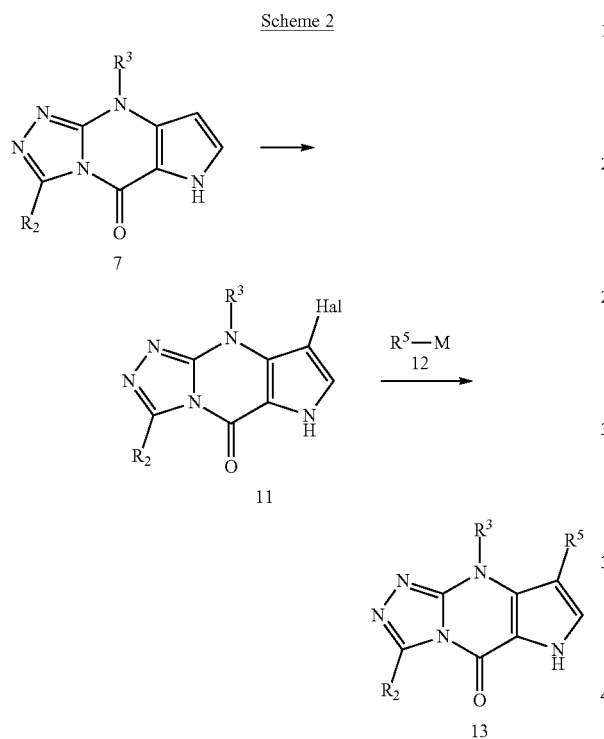

A compound of formula 16 can be prepared using the synthetic route outlined in Scheme 3. Compound 4 (prepared according to Scheme 1) is subjected to deamination using an appropriate procedure, such as first converting 4 to the diazonium salt using aqueous sodium nitrite, then cleaving the intermediate using a reductant such as zinc metal in acetic acid, to furnish 14. Condensation of compound 14 with a carbonyl adduct of formula 15 (Hal is a halide, such as F, Cl, Br, or I) at elevated temperature generates the tricylclic compound 16.

Scheme 3

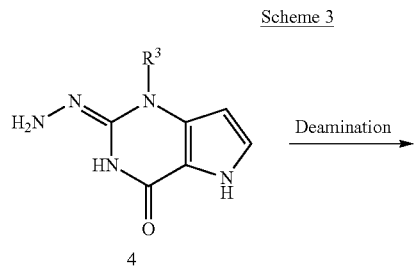

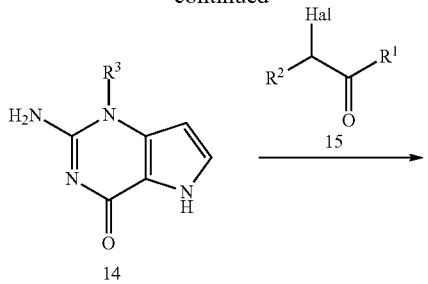

A compound of formula 9a (a subset of compounds of formula 9) can be prepared using the synthetic route outlined in Scheme 4. Compound 17 is subjected to an appropriate chemical transformation, such as a S$_N$2 reaction, with compound 18 (Hal is a halide, such as F, Cl, Br, or I) to furnish a derivative of formula 9a.

Scheme 4

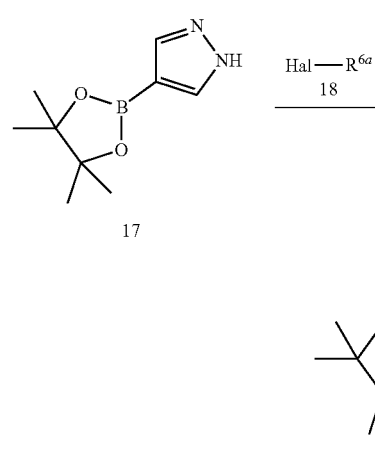

A compound of formula 22 can be prepared using the synthetic route outlined in Scheme 5. Compound 19 (prepared according to Scheme 1) is coupled to an adduct of formula 9b (prepared according to Scheme 4) under standard Suzuki cross-coupling conditions (e.g., in the presence of a palladium catalyst and a suitable base); then the protecting group (Boc is tert-butyloxycarbonyl) is removed under suitable conditions, such as in the presence of trifluoroactic acid, to furnish a derivative of compound 20. Compound 20 is then subjected to an appropriate chemical transformation, such as a S$_N$Ar reaction, with an adduct of formula 21 (Hal is a halide, such as F, Cl, Br, or I) to furnish a derivative of formula 22.

Scheme 5

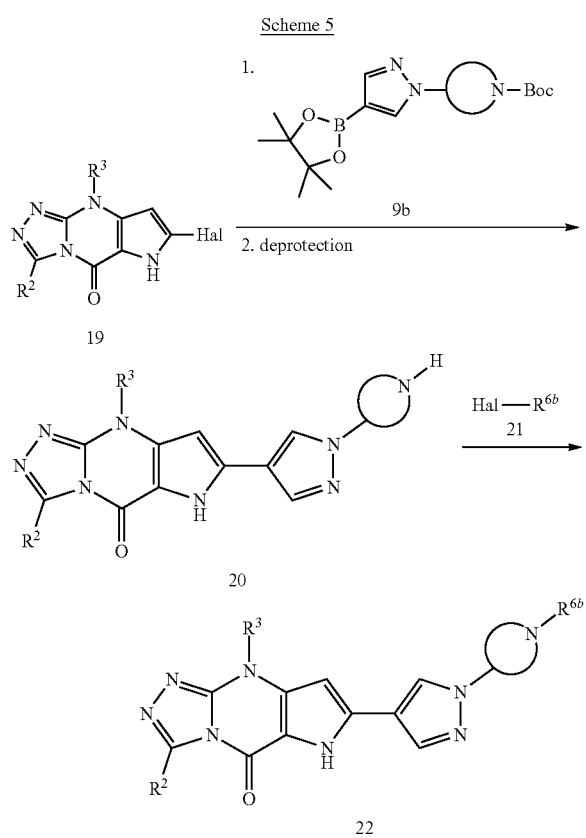

Methods of Use

The compounds of the present disclosure can modulate the activity of adenosine receptors, such as subtypes A2A and A2B receptors. Accordingly, the compounds, salts or stereoisomers described herein can be used in methods of inhibiting adenosine receptors (e.g., A2A and/or A2B receptors) by contacting the receptor with any one or more of the compounds, salts, or compositions described herein. In some embodiments, the compounds or salts can be used in methods of inhibiting activity of an adenosine receptor in an individual/patient in need of the inhibition by administering an effective amount of a compound or salt of described herein. In some embodiments, modulating is inhibiting. In some embodiments, the contacting is in vivo. In some embodiments, the contacting is ex vivo or in vitro.

The compounds or salts described herein can be selective. By "selective," it is meant that the compound binds to or inhibits an adenosine receptor with greater affinity or potency, respectively, compared to at least one other receptor, kinase, etc. The compounds of the present disclosure can also be dual antagonists (i.e., inhibitors) of adenosine receptors, e.g., A2A and A2B adenosine receptors.

Another aspect of the present disclosure pertains to methods of treating an adenosine receptor associated disease or disorder in an individual (e.g., patient) by administering to the individual in need of such treatment a therapeutically effective amount or dose of one or more compounds of the present disclosure or a pharmaceutical composition thereof. An adenosine receptor associated disease or disorder can include any disease, disorder or condition that is directly or indirectly linked to expression or activity of the adenosine receptor, including overexpression and/or abnormal activity levels.

The compounds of the present disclosure are useful in the treatment of diseases related to the activity of adenosine receptors including, for example, cancer, inflammatory diseases, cardiovascular diseases, neurodegenerative diseases, immunomodulatory disorders, central nerve system diseases, and diabetes.

Based on the compelling roles of adenosine, e.g., A2A, A2B, receptors in multiple immunosuppressive mechanisms, developing inhibitors can boost immune system to suppress tumor progression. Adenosine receptor inhibitors can be used to treat, alone or in combination with other therapies, bladder cancer, lung cancer (e.g., non-small cell lung cancer (NSCLC), lung metastasis), melanoma (e.g., metastatic melanoma), breast cancer, cervical cancer, ovarian cancer, colorectal cancer, pancreatic cancer, esophageal cancer, prostate cancer, kidney cancer, skin cancer, thyroid cancer, liver cancer, uterine cancer, head and neck cancer, and renal cell carcinoma (Antonioli, L. et al., *Nature Reviews Cancer*, 2013, 13, 842-857). See also, https://globenewswire.com/news-release/2017/04/04/954192/0/en/Corvus-Pharmaceuticals-Announces-Interim-Results-from-Ongoing-Phase-1-1b-Study-Demonstrating-Safety-and-Clinical-Activity-of-Lead-Checkpoint-Inhibitor-CPI-444-in-Patients-with-Adva.html; Cekic C. et al., *J Immunol*, 2012, 188:198-205; Iannone, R. et al., *Am. J Cancer Res.* 2014, 4:172-181 (study shows that both A2A and CD73 blockade enhance the antitumor activity of anti-CTLA-4 mAb therapy in a B16F10 murine melanoma model); Iannone, R. et al., *Neoplasia*, 2013, 15:1400-1410 and Beavis P A., et al., *Proc Natl Acad Sci. USA*, 2013, 110:14711-14716 (study shows that A2A and CD73 blockade decreased metastasis in 4T1 breast tumor model with has high CD73 expression). In some embodiments, the prostate cancer is metastatic castrate-resistant prostate carcinoma (mCRPC). In some embodiments, the colorectal cancer is colorectal carcinoma (CRC).

In some embodiments, the compounds of the disclosure can be used in treating pulmonary inflammation, including bleomycin-induced pulmonary fibrosis and injury related to adenosine deaminase deficiency (Baraldi, et al., *Chem. Rev.*, 2008, 108, 238-263).

In some embodiments, the compounds of the disclosure can be used as a treatment for inflammatory disease such as allergic reactions (e.g., A2B adenosine receptor dependent allergic reactions) and other adenosine receptor dependent immune reactions. Further inflammatory diseases that can be treated by compounds of the disclosure include respiratory disorders, sepsis, reperfusion injury, and thrombosis.

In some embodiments, the compounds of the disclosure can be used as a treatment for cardiovascular disease such as coronary artery disease (myocardial infarction, angina pectoris, heart failure), cerebrovascular disease (stroke, transient ischemic attack), peripheral artery disease, and aortic atherosclerosis and aneurysm. Atherosclerosis is an underlying etiologic factor in many types of cardiovascular disease. Atherosclerosis begins in adolescence with fatty streaks, which progress to plaques in adulthood and finally results in thrombotic events that cause occlusion of vessels leading to clinically significant morbidity and mortality. Antagonists to the A2B adenosine receptor and A2A adenosine receptor may be beneficial in preventing atherosclerotic plaque formation (Eisenstein, A. et al., *J. Cell Physiol.*, 2015, 230(12), 2891-2897).

In some embodiments, the compounds of the disclosure can be used as a treatment for disorders in motor activity; deficiency caused by degeneration of the striatonigral dopamine system; and Parkinson's disease; some of the motivational symptoms of depression (Collins, L. E. et al. *Pharmacol. Biochem. Behav.,* 2012, 100, 498-505).

In some embodiments, the compounds of the disclosure can be used as a treatment for diabetes and related disorders, such as insulin resistance. Diabetes affects the production of adenosine and the expression of A2B adenosine receptors (A2BRs) that stimulate IL-6 and CRP production, insulin resistance, and the association between $A_{2B}R$ gene single-nucleotide polymorphisms (ADORA2B SNPs) and inflammatory markers. The increased A2BR signaling in diabetes may increase insulin resistance in part by elevating pro-inflammatory mediators. Selective A2BR blockers may be useful to treat insulin resistance (Figler, R. A. et al. *Diabetes,* 2011, 60 (2), 669-679).

Combination Therapies

I. Immune-Checkpoint Therapies

In some embodiments, A2A and A2B dual inhibitors provided herein can be used in combination with one or more immune checkpoint inhibitors for the treatment of cancer as described herein. In one embodiment, the combination with one or more immune checkpoint inhibitors as described herein can be used for the treatment of melanoma. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1 BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the A2A and A2B dual inhibitors provided herein can be used in combination with one or more agonists of immune checkpoint molecules, e.g., OX40, CD27, OX40, GITR, and CD137 (also known as 4-1 BB).

In some embodiments, the inhibitor of an immune checkpoint molecule is anti-PD 1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD 1 antibody is pembrolizumab. In some embodiments, the anti-PD-1 monoclonal antibody is MGA012. In some embodiments, the anti-PD 1 antibody is SHR-1210. Other anti-cancer agent(s) include antibody therapeutics such as 4-1 BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MED14736, MPDL3280A (also known as RG7446), or MSB0010718C.

In some embodiments, the anti-PD-L1 monoclonal antibody is MPDL3280A or MED14736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein.

The compounds of the present disclosure can be used in combination with one or more additional pharmaceutical agents such as, for example, chemotherapeutics, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF and FAK kinase inhibitors. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, taxotere, taxol, camptostar, epothilones, 5-fluorouracil, SCH 66336, R115777, L778,123, BMS 214662, IRESSA™ (gefitinib), TARCEVA™ (erlotinib), antibodies to EGFR, GLEEVEC™ (imatinib mesylate), intron, ara-C, adriamycin, cytoxan, chlormethine, triethylenemelamine, triethylenethiophosphoramine, busulfan, 6-mercaptopurine, 6-thioguanine, fludarabine phosphate, ELOXATIN™ (oxaliplatin), vindesine, mithramycin, deoxycoformycin, L-asparaginase, 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, medroxyprogesteroneacetate, leuprolide, flutamide, goserelin, hydroxyurea, amsacrine, navelbene, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), aphidicolon, rituxan, Sml1, triapine, didox, trimidox, amidox, 3-AP, and MDL-101, 731.

The compounds of the present disclosure can further be used in combination with other methods of treating cancers, for example by chemotherapy, irradiation therapy, tumortargeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the disclosure can be used in combination with one or more other kinase inhibitors including imatinib, particularly for treating patients resistant to imatinib or other kinase inhibitors.

The compounds can be used in combination with tumor vaccines and CAR (Chimeric antigen receptor) T cell treatment as a booster for T cell activation. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV).

In some embodiments, the compounds of the present disclosure can be used in combination with tumor specific antigen such as heat shock proteins isolated from tumor tissue itself. In some embodiments, the compounds can be combined with dendritic cells immunization to activate potent anti-tumor responses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the disclosure contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the disclosure contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the disclosure contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the disclosure.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

Another aspect of the present disclosure relates to labeled compounds of the disclosure (radio-labeled, fluorescent-labeled, etc.) that would be useful not only in imaging techniques but also in assays, both in vitro and in vivo, for localizing and quantitating A2A and/or A2B receptors in tissue samples, including human, and for identifying A2A and/or A2B antagonists by inhibition binding of a labeled compound. Substitution of one or more of the atoms of the compounds of the present disclosure can also be useful in generating differentiated ADME (Adsorption, Distribution, Metabolism and Excretion.) Accordingly, the present disclosure includes adenosine receptor (e.g., A2A and/or A2B) assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^3$H, $^{14}$C, $^{82}$Br, $^{125}$I, $^{131}$I Or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the disclosure can be used in a screening assay to identify/evaluate compounds. For example, a newly synthesized or identified compound (i.e., test compound) which is labeled can be evaluated for its ability to bind an adenosine receptor by monitoring its concentration variation when contacting with the adenosine receptor, through tracking of the labeling. For example, a test compound (labeled) can be evaluated for its ability to reduce binding of another compound which is known to bind to a an adenosine receptor (i.e., standard compound). Accordingly, the ability of a test compound to compete with the standard compound for binding to the adenosine receptor directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, for example, in the treatment or prevention of adenosine receptor-associated diseases or disorders (such as, e.g., cancer, an inflammatory disease, a cardiovascular disease, or a neurodegenerative disease) which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of an adenosine receptor (e.g., A2A and/or A2B) according to at least one assay described herein.

EXAMPLES

Preparatory LC-MS purifications of some of the compounds prepared were performed on Waters mass directed fractionation systems. The basic equipment setup, protocols, and control software for the operation of these systems have been described in detail in the literature (see e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Haque, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004)). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm, 30×100 mm or Waters XBridge™ $C_{18}$ 5 μm, 30×100 mm column, eluting with mobile phase A: 0.1% TFA (trifluoroacetic acid) in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J. Comb. Chem.*, 6, 874-883 (2004)).

pH=10 purifications: Waters XBridge™ $C_{18}$ 5 μm, 30×100 mm column, eluting with mobile phase A: 0.1% $NH_4OH$ in water and mobile phase B: acetonitrile; the flow rate was 60 mL/minute, the separating gradient was optimized for each compound using the Compound Specific Method Optimization protocol as described in the literature (see e.g. "Preparative LCMS Purification: Improved Compound Specific Method Optimization", K. Blom, B. Glass, R. Sparks, A. Combs, *J Comb. Chem.*, 6, 874-883 (2004)).

Example 1. 3-Methyl-9-pentyl-6,9-dihydro-5H-pyrrolo[3,2-d][1,2,4]triazolo[4,3-a]pyrimidin-5-one

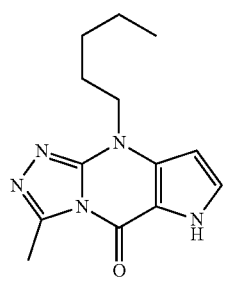 [SMILES: CCCCCn1c2cc[nH]c2c(=O)n2c(C)nnc12]

Step 1: Ethyl 3-(pentylamino)-1H-pyrrole-2-carboxylate

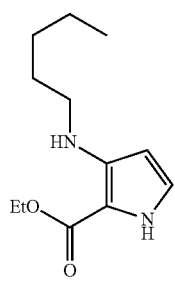 [SMILES: CCCCCNc1cc[nH]c1C(=O)OCC]

Ethyl 3-amino-1H-pyrrole-2-carboxylate (5 g, 32.4 mmol), pentanal (3.79 ml, 35.7 mmol), and sodium cyanoborohydride (2.038 g, 32.4 mmol) were mixed in methanol (64.9 ml) at room temperature overnight. The reaction mixture was concentrated under reduced pressure. The crude residue was purified by flash chromatography (0 to 100% EtOAc in hexanes) to give the desired product (4.4 g, 61%). LCMS calculated for $C_{12}H_{21}N_2O_2$ (M+H): 225.2. Found: 225.1.

Step 2: Ethyl 3-(3-(ethoxycarbonyl)-1-pentylthioureido)-1H-pyrrole-2-carboxylate

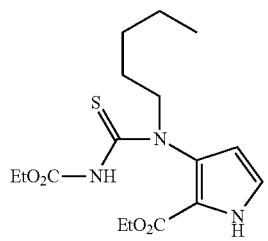

A vial was charged with ethyl 3-(pentylamino)-1H-pyrrole-2-carboxylate (4.4 g, 19.62 mmol), dichloromethane (39.2 ml), and ethoxycarbonyl isothiocyanate (2.78 ml, 23.54 mmol). The reaction mixture was stirred at room temperature overnight. The reaction mixture was quenched with water (40 ml), and the layers were separated. The aqueous layer was extracted with dichloromethane (3×40 mL) and the combined organic fractions were dried over $MgSO_4$, filtered, and concentrated. The crude material was used in the next step without further purification (7.3 g, quant.). LCMS calculated for $C_{1-6}H_{26}N_3O_4S$ (M+H): 356.2. Found: 356.1.

Step 3: 1-Pentyl-2-thioxo-2,3-dihydro-1H-pyrrolo[3,2-d]pyrimidin-4(5H)-one

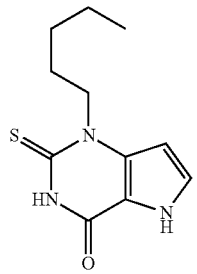 [SMILES: CCCCCn1c(=S)[nH]c(=O)c2[nH]ccc21]

A microwave vial was charged with ethyl 3-(3-(ethoxycarbonyl)-1-pentylthioureido)-1H-pyrrole-2-carboxylate (7.31 g, 20.57 mmol) and sodium ethoxide (21% w/w, 8.45 ml, 22.62 mmol) solution. The vial was capped and heated in a microwave reactor for 10 minutes at 120 degrees Celsius. The reaction mixture was brought to neutral pH on addition of 1M HCl solution and the solid product was filtered and dried (3.1 g, 64%). LCMS calculated for $C_{11}H_{16}N_3OS$ (M+H): 238.1. Found: 238.1.

Step 4: 2-Hydrazono-1-pentyl-2,3-dihydro-1H-pyrrolo[3,2-d]pyrimidin-4(5H)-one

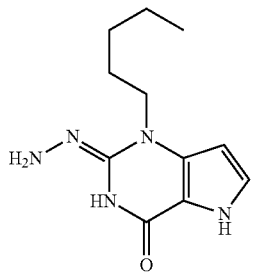 [SMILES: CCCCCn1/c(=N/N)[nH]c(=O)c2[nH]ccc21]

A vial was charged with 1-pentyl-2-thioxo-2,3-dihydro-1H-pyrrolo[3,2-d]pyrimidin-4(5H)-one (3.13 g, 13.19 mmol) and hydrazine hydrate (20 mL). The reaction mixture was stirred at 100 degrees Celsius overnight. The solid formed was filtered and washed with water to give the desired product (2.2 g, 70%). LCMS calculated for $C_{11}H_{18}N_5O$ (M+H): 236.1. Found: 236.1.

Step 5: 3-Methyl-9-pentyl-6,9-dihydro-5H-pyrrolo[3,2-d][1,2,4]triazolo[4,3-a]pyrimidin-5-one A vial was charged with (E)-2-hydrazono-1-pentyl-2,3-dihydro-1H-pyrrolo[3,2-d]pyrimidin-4(5H)-one (4.8 g, 20.40 mmol), a drop of trifluoroacetic acid, and triethyl orthoacetate (20 mL). The reaction mixture was heated to 110 degrees Celsius for three hours. The suspension was filtered, washed with hexanes, and dried (4.0 g, 76%). LCMS calculated for $C_{13}H_{18}N_5O$ (M+H): 260.1. Found: 260.2.

Example 2. 7-(1-((5-Chloropyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one

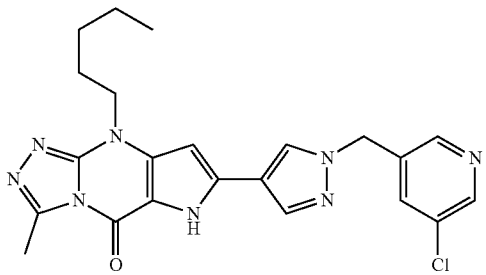 [SMILES: CCCCCn1c2cc(-c3cnn(Cc4cncc(Cl)c4)c3)[nH]c2c(=O)n2c(C)nnc12]

Step 1: 3-Methyl-9-pentyl-6-(phenylsulfonyl)-6,9-dihydro-5H-pyrrolo[3,2-d][1,2,4]triazolo[4,3-a]pyrimidin-5-one

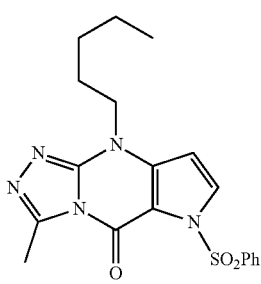

A vial was charged with 3-methyl-9-pentyl-6,9-dihydro-5H-pyrrolo[3,2-d][1,2,4]triazolo[4,3-a]pyrimidin-5-one (from Example 1) (4 g, 15.43 mmol), dichloromethane (40 mL), dimethylaminopyridine (0.188 g, 1.543 mmol), triethylamine (3.23 ml, 23.14 mmol), and benzenesulfonyl chloride (2.187 ml, 16.97 mmol). The reaction mixture was stirred at room temperature for one hour. The reaction mixture was quenched with water, and the layers were separated. The aqueous layer was extracted with dichloromethane (3×40 mL) and the combined organic fractions were dried over $MgSO_4$, filtered, and concentrated. The crude material was used in the next step without further purification (6.1 g, quant.). LCMS calculated for $C_{19}H_{22}N_5O$ (M+H): 400.1. Found: 400.1.

Step 2: 7-Bromo-3-methyl-9-pentyl-6-(phenylsulfonyl)-6,9-dihydro-5H-pyrrolo[3,2-d][1,2,4]triazolo[4,3-a]pyrimidin-5-one

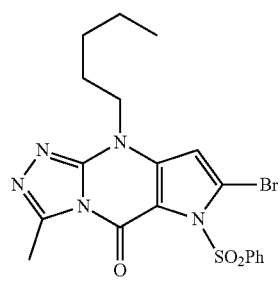

A vial was charged with 3-methyl-9-pentyl-6-(phenylsulfonyl)-6,9-dihydro-5H-pyrrolo[3,2-d][1,2,4]triazolo[4,3-a]pyrimidin-5-one (1 g, 2.503 mmol), dry THF (30 mL) and the mixture was cooled to −78 degrees Celsius. Lithium diisopropylamide solution (1M in hexanes/THF, 3.13 ml, 3.13 mmol) was added dropwise. The reaction mixture was maintained at −78° C. for 1.5 hours. A solution of 1,2-dibromo-1,1,2,2-tetrachloroethane (1.223 g, 3.75 mmol) in dry THF (3 ml) was added dropwise to the reaction mixture and the reaction mixture was maintained at −78° C. for a further 1.5 hours. The reaction mixture was quenched with sat. aq. $NH_4Cl$ solution (30 mL) and diluted with dichloromethane (30 mL). The layers were separated and the aqueous layer was extracted with DCM (3×30 mL). The combined organic fractions were dried over $MgSO_4$, filtered, and concentrated. The crude residue was purified by automated flash chromatography (0 to 100% EtOAc in DCM) to give the desired product (0.84 g, 70%). LCMS calculated for $C_{19}H_{21}BrN_5O_3S$ (M+H): 478.1. Found: 478.1.

Step 3: 3-Chloro-5-((4-(4,4,5,5-tetramethyl-1,3,2-dioxaborolan-2-yl)-1H-pyrazol-1-yl)methyl)pyridine

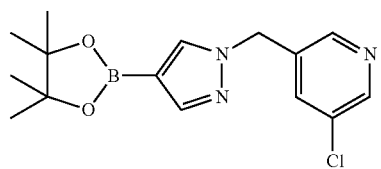 [SMILES: CC1(C)OB(c2cnn(Cc3cncc(Cl)c3)c2)OC1(C)C]

A vial was charged with 4-(4,4,5,5-tetramethyl-1,3,2-dioxaborolan-2-yl)-1H-pyrazole (0.5 g, 2.58 mmol), 3-(bromomethyl)-5-chloropyridine hydrobromide (0.741 g, 2.58 mmol), cesium carbonate (2.52 g, 7.73 mmol), and DMF (6.44 ml). The reaction mixture was stirred at 60 degrees Celsius for one hour. The reaction mixture was quenched with water (10 ml) and diluted with dichloromethane (10 ml). The layers were separated, and the aqueous layer was extracted with dichloromethane (3×10 mL). The combined dichloromethane extracts were dried over MgSO$_4$, filtered, and concentrated. Purification by automated flash chromatography (0 to 100% EtOAc in DCM) afforded the product (0.548 g, 67%). LCMS calculated for $C_{15}H_{20}BClN_3O_2$ (M+H): 320.1, 322.1. Found: 320.1, 322.1.

Step 4: 7-(1-((5-Chloropyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one A vial was charged with 7-bromo-3-methyl-9-pentyl-6-(phenylsulfonyl)-6,9-dihydro-5H-pyrrolo[3,2-d][1,2,4]triazolo[4,3-a]pyrimidin-5-one (0.01 g, 0.021 mmol), 3-chloro-5-((4-(4,4,5,5-tetramethyl-1,3,2-dioxaborolan-2-yl)-1H-pyrazol-1-yl)methyl)pyridine (0.013 g, 0.042 mmol), Chloro(2-dicyclohexylphosphino-2',4',6'-triisopropyl-1,1'-biphenyl)[2-(2'-amino-1,1'-biphenyl)]palladium(II) (5.00 mg, 0.006 mmol) and potassium phosphate tribasic (0.016 g, 0.074 mmol). 1,4-dioxane (0.35 ml) and water (0.07 ml) were added and the reaction mixture was sparged with nitrogen gas for 5 minutes then stirred at 90° C. for two hours. The reaction mixture was cooled to room temperature and sodium hydroxide (10 mg) was added. The reaction mixture was stirred at 40 degrees Celsius for 60 minutes. The reaction mixture was cooled to room temperature and diluted with DMF (5 ml). Purification by preparative HPLC (pH 2, acetonitrile/water with TFA) afforded the product as a TFA salt (2 mg, 21%). LCMS calculated for $C_{22}H_{24}ClN_8O$ (M+H): 451.2, 453.2. Found: 451.2, 453.2.

Example 3. 3-Methyl-7-(1-((5-methylpyridin-3-yl)methyl)-1H-pyrazol-4-yl)-9-pentyl-6,9-dihydro-5H-pyrrolo[3,2-d][1,2,4]triazolo[4,3-a]pyrimidin-5-one

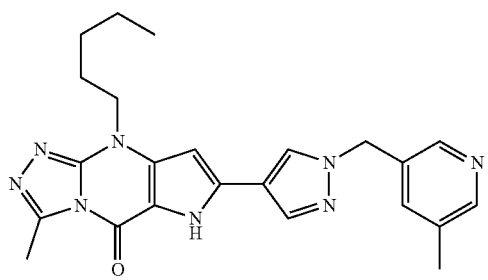 [SMILES: CCCCCn1c2cc(-c3cnn(Cc4cncc(C)c4)c3)[nH]c2c(=O)n2c(C)nnc12]

This compound was prepared using similar procedures as described in Example 2 using 3-(bromomethyl)-5-methylpyridine in place of 3-(bromomethyl)-5-chloropyridine hydrobromide in Step 3. LCMS calculated for $C_{23}H_{27}N_5O$ (M+H): 431.2. Found: 431.3.

Example 4. 3-Methyl-9-pentyl-7-(1-(thieno[3,2-b]pyridin-6-ylmethyl)-1H-pyrazol-4-yl)-6,9-dihydro-5H-pyrrolo[3,2-d][1,2,4]triazolo[4,3-a]pyrimidin-5-one

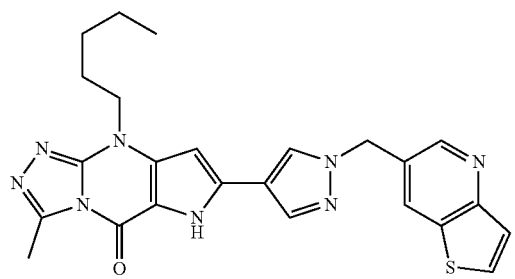 [SMILES: CCCCCn1c2cc(-c3cnn(Cc4cnc5ccsc5c4)c3)[nH]c2c(=O)n2c(C)nnc12]

This compound was prepared using similar procedures as described in Example 2 using 6-(bromomethyl)thieno[3,2-b]pyridine in place of 3-(bromomethyl)-5-chloropyridine hydrobromide in Step 3. LCMS calculated for $C_{24}H_{25}N_5OS$ (M+H): 473.2. Found: 473.3.

Example 5. 7-(1-(Imidazo[1,2-a]pyridin-7-ylmethyl)-1H-pyrazol-4-yl)-3-methyl-9-pentyl-6,9-dihydro-5H-pyrrolo[3,2-d][1,2,4]triazolo[4,3-a]pyrimidin-5-one

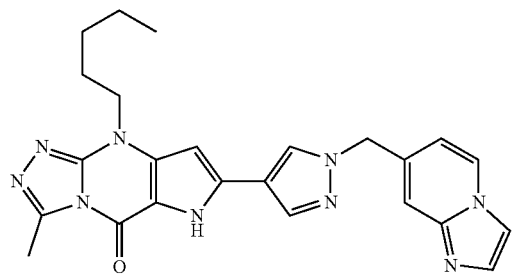 [SMILES: CCCCCn1c2cc(-c3cnn(Cc4ccn5ccnc5c4)c3)[nH]c2c(=O)n2c(C)nnc12]

This compound was prepared using similar procedures as described in Example 2 using 7-(bromomethyl)imidazo[1,2-a]pyridine in place of 3-(bromomethyl)-5-chloropyridine hydrobromide in Step 3. LCMS calculated for $C_{24}H_{26}N_9O$ (M+H): 456.2. Found: 456.3.

Example 6. 7-(1-((1,5-Naphthyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one

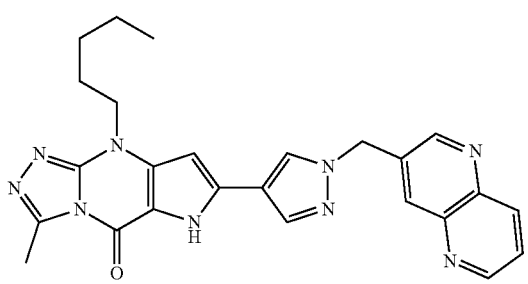 [SMILES: CCCCCn1c2cc(-c3cnn(Cc4cnc5cccnc5c4)c3)[nH]c2c(=O)n2c(C)nnc12]

This compound was prepared using similar procedures as described in Example 2 using 3-(bromomethyl)-1,5-naphthyridine in place of 3-(bromomethyl)-5-chloropyridine hydrobromide in Step 3. LCMS calculated for $C_{25}H_{26}N_9O$ (M+H): 468.2. Found: 468.2.

Example 7. 3-Methyl-7-(1-((1-methyl-1H-pyrazolo [4,3-b]pyridin-6-yl)methyl)-1H-pyrazol-4-yl)-9-pentyl-6,9-dihydro-5H-pyrrolo[3,2-d][1,2,4]triazolo [4,3-a]pyrimidin-5-one

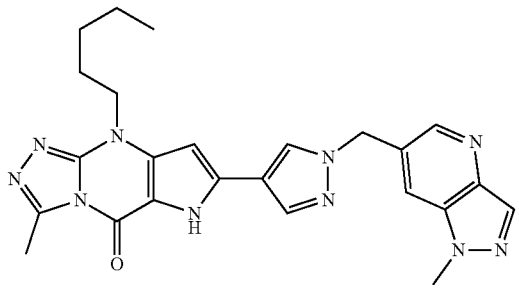 [SMILES: CCCCCn1c2cc(-c3cnn(Cc4cnc5cnn(C)c5c4)c3)[nH]c2c(=O)n2c(C)nnc12]

This compound was prepared using similar procedures as described in Example 2 using 6-(bromomethyl)-1-methyl-1H-pyrazolo[4,3-b]pyridine in place of 3-(bromomethyl)-5-chloropyridine hydrobromide in Step 3. LCMS calculated for $C_{24}H_{27}N_{10}O$ (M+H): 471.2. Found: 471.2.

Example 8. 3-Methyl-9-pentyl-7-(1-(pyridin-3-ylmethyl)-1H-pyrazol-4-yl)-6,9-dihydro-5H-pyrrolo[3,2-d][1,2,4]triazolo[4,3-a]pyrimidin-5-one

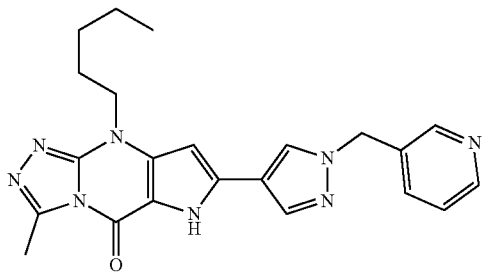 [SMILES: CCCCCn1c2cc(-c3cnn(Cc4cccnc4)c3)[nH]c2c(=O)n2c(C)nnc12]

This compound was prepared using similar procedures as described in Example 2 using 3-(bromomethyl)pyridine in place of 3-(bromomethyl)-5-chloropyridine hydrobromide in Step 3. LCMS calculated for $C_{22}H_{25}N_8O$ (M+H): 417.2. Found: 417.2.

Example 9. 7-(1-((5-Fluoropyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one

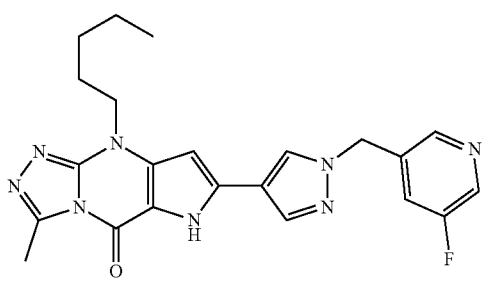 [SMILES: CCCCCn1c2cc(-c3cnn(Cc4cncc(F)c4)c3)[nH]c2c(=O)n2c(C)nnc12]

This compound was prepared using similar procedures as described in Example 2 using 3-(bromomethyl)-5-fluoropyridine in place of 3-(bromomethyl)-5-chloropyridine hydrobromide in Step 3. LCMS calculated for $C_{22}H_{24}FN_8O$ (M+H): 435.2. Found: 435.2.

Example 10. 7-(1-Benzyl-1H-pyrazol-4-yl)-3-methyl-9-pentyl-6,9-dihydro-5H-pyrrolo[3,2-d][1,2,4]triazolo[4,3-a]pyrimidin-5-one

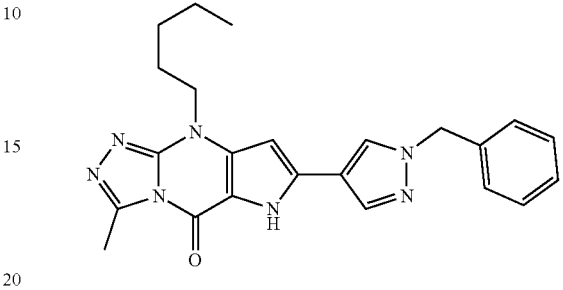

This compound was prepared using similar procedures as described in Example 2 using (bromomethyl)benzene in place of 3-(bromomethyl)-5-chloropyridine hydrobromide in Step 3. LCMS calculated for $C_{23}H_{26}N_7O$ (M+H): 416.2. Found: 416.2.

Example 11. 4-(3-Methyl-5-oxo-9-pentyl-6,9-dihydro-5H-pyrrolo[3,2-d][1,2,4]triazolo[4,3-a]pyrimidin-7-yl)-N-p-tolylbenzenesulfonamide

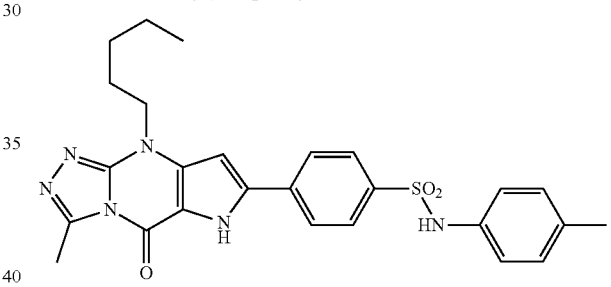

This compound was prepared using similar procedures as described in Example 2 using 4-(N-p-tolylsulfamoyl)phenylboronic acid in place of 3-chloro-5-((4-(4,4,5,5-tetramethyl-1,3,2-dioxaborolan-2-yl)-1H-pyrazol-1-yl)methyl) pyridine in Step 4. LCMS calculated for $C_{26}H_{29}N_6O_3S$ (M+H): 505.2. Found: 505.1.

Example 12. 7-(1-(((1,5-Naphthyridin-3-yl)methyl)-1H-pyrazol-4-yl)-9-pentyl-3-(trifluoromethyl)-6,9-dihydro-5H-pyrrolo[3,2-d][1,2,4]triazolo[4,3-a]pyrimidin-5-one

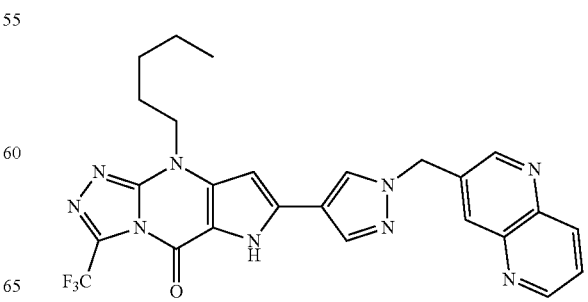

Step 1: 9-Pentyl-3-(trifluoromethyl)-6,9-dihydro-5H-pyrrolo[3,2-d][1,2,4]triazolo[4,3-a]pyrimidin-5-one

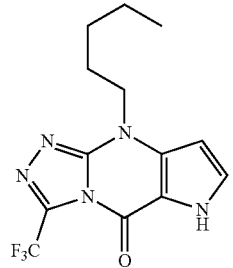 [SMILES: CCCCCn1c2cc[nH]c2c(=O)n2c(C(F)(F)F)nnc12]

A 100-mL round bottom flask was charged with (E)-2-hydrazono-1-pentyl-2,3-dihydro-1H-pyrrolo[3,2-d]pyrimidin-4(5H)-one (from Example 1, Step 4) (1.16 g, 4.93 mmol) and trifluoroacetic anhydride (50 mL). The reaction mixture was stirred at reflux overnight. The solvent was removed under reduced pressure, and the crude residue dissolved into dichloromethane. Saturated aqueous NaHCO$_3$ was added slowly and the biphasic mixture was stirred rapidly for 30 minutes. The layers were separated, and the aqueous phase was extracted 3× with DCM. The combined organic fractions were dried over MgSO$_4$, filtered, and concentrated to afford the product (1.48 g, 96%). LCMS calculated for $C_{13}H_{15}F_3N_5O$ (M+H): 314.1. Found: 314.2.

Step 2: 9-Pentyl-6-(phenylsulfonyl)-3-(trifluoromethyl)-6,9-dihydro-5H-pyrrolo[3,2-d][1,2,4]triazolo[4,3-a]pyrimidin-5-one

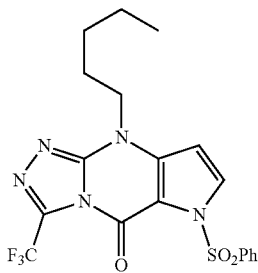

A vial was charged with 9-pentyl-3-(trifluoromethyl)-6,9-dihydro-5H-pyrrolo[3,2-d][1,2,4]triazolo[4,3-a]pyrimidin-5-one (1.48 g, 4.72 mmol), dichloromethane (12 mL), dimethylaminopyridine (0.058 g, 0.472 mmol), triethylamine (1.00 ml, 7.09 mmol), and benzenesulfonyl chloride (0.67 ml, 5.20 mmol). The reaction mixture was stirred at room temperature for one hour. The reaction mixture was quenched with water, and the layers were separated. The aqueous layer was extracted with dichloromethane (3×40 mL), and the combined organic fractions were dried over MgSO$_4$, filtered, and concentrated. The crude material was used in the next step without further purification (2.14 g, quant.). LCMS calculated for $C_{19}H_{19}F_3N_5O_3S$ (M+H): 454.1. Found: 454.1.

Step 3: 7-Bromo-9-pentyl-6-(phenylsulfonyl)-3-(trifluoromethyl)-6,9-dihydro-5H-pyrrolo[3,2-d][1,2,4]triazolo[4,3-a]pyrimidin-5-one

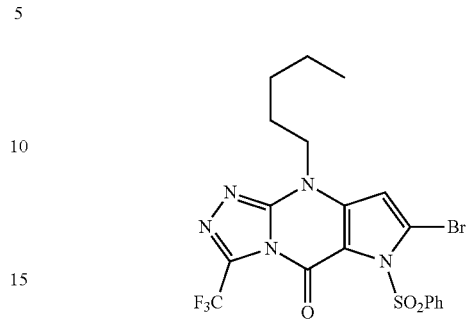

A vial was charged with 9-pentyl-6-(phenylsulfonyl)-3-(trifluoromethyl)-6,9-dihydro-5H-pyrrolo[3,2-d][1,2,4]triazolo[4,3-a]pyrimidin-5-one (1 g, 2.21 mmol), dry THF (40 mL) and the mixture was cooled to −78 degrees Celsius. Lithium diisopropylamide solution (1M in hexanes/THF, 3.31 ml, 3.31 mmol) was added dropwise. The reaction mixture was maintained at −78° C. for 1.5 hours. A solution of 1,2-dibromo-1,1,2,2-tetrachloroethane (1.44 g, 4.41 mmol) in dry THF (3 ml) was added dropwise to the reaction mixture and the reaction mixture was maintained at −78° C. for a further 1.5 hours. The reaction mixture was quenched with sat. aq. NH$_4$Cl solution (30 mL) and diluted with dichloromethane (30 mL). The layers were separated and the aqueous layer was extracted with DCM (3×30 mL). The combined organic fractions were dried over MgSO4, filtered, and concentrated. The crude residue was purified by flash chromatography (0 to 15% EtOAc in DCM) to give the desired product (0.35 g, 30%). LCMS calculated for $C_{19}H_{18}BrF_3N_5O_3S$ (M+H): 532.0. Found: 532.0.

Step 4: 7-(1-((1,5-Naphthyridin-3-yl)methyl)-1H-pyrazol-4-yl)-9-pentyl-3-(trifluoromethyl)-6,9-dihydro-5H-pyrrolo[3,2-d][1,2,4]triazolo[4,3-a]pyrimidin-5-one

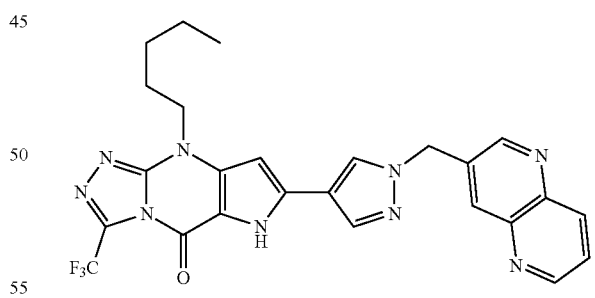

A vial was charged with 7-bromo-9-pentyl-6-(phenylsulfonyl)-3-(trifluoromethyl)-6,9-dihydro-5H-pyrrolo[3,2-d][1,2,4]triazolo[4,3-a]pyrimidin-5-one (0.015 g, 0.028 mmol), 3-((4-(4,4,5,5-tetramethyl-1,3,2-dioxaborolan-2-yl)-1H-pyrazol-1-yl)methyl)-1,5-naphthyridine (0.019 g, 0.056 mmol), Chloro(2-dicyclohexylphosphino-2',4',6'-triisopropyl-1,1'-biphenyl)[2-(2'-amino-1,1'-biphenyl)]palladium(II) (6.64 mg, 0.008 mmol) and potassium phosphate tribasic (0.020 g, 0.093 mmol). 1,4-dioxane (0.47 ml) and water (0.1 ml) were added, and the reaction mixture was sparged with nitrogen gas for 5 minutes then stirred at 90° C. for two hours. The reaction mixture was cooled to room temperature and diluted with DMF (5 ml). Purification by preparative HPLC (pH 2, acetonitrile/water with TFA) afforded the product as a TFA salt (3 mg, 21% yield). LCMS calculated for $C_{25}H_{23}F_3N_9O$ (M+H): 522.2. Found: 522.2.

Example 13. 8-Bromo-3-methyl-9-pentyl-6,9-dihydro-5H-pyrrolo[3,2-d][1,2,4]triazolo[4,3-a]pyrimidin-5-one

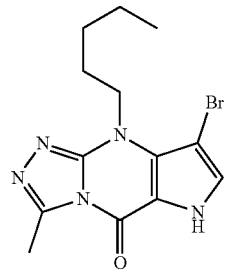 [SMILES: CCCCCn1c2c(Br)c[nH]c2c(=O)n2c(C)nnc12]

A vial was charged with 3-methyl-9-pentyl-6,9-dihydro-5H-pyrrolo[3,2-d][1,2,4]triazolo[4,3-a]pyrimidin-5-one (from Example 1) (0.02 g, 0.077 mmol), THF (0.77 ml), and NBS (0.014 g, 0.077 mmol). The reaction mixture was stirred overnight at room temperature in the dark. The solvent was removed under reduced pressure, and the crude residue was suspended in water then filtered. The crude material was used in the next step without further purification (0.026 g, quant.). $^1$H NMR (500 MHz, DMSO) δ 12.85 (s, 1H), 7.70 (d, J=3.4 Hz, 1H), 4.50-4.41 (m, 2H), 2.74 (s, 3H), 1.85-1.74 (m, 2H), 1.42-1.29 (m, 4H), 0.92-0.84 (m, 3H). LCMS calculated for $C_{13}H_{17}BrN_5O$ (M+H): 338.1. Found: 338.0.

Example 14. 3,8-Dimethyl-9-pentyl-6,9-dihydro-5H-pyrrolo[3,2-d][1,2,4]triazolo[4,3-a]pyrimidin-5-one

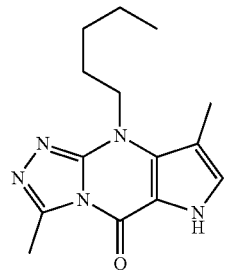 [SMILES: CCCCCn1c2c(C)c[nH]c2c(=O)n2c(C)nnc12]

In a sealed vial, a mixture of 8-bromo-3-methyl-9-pentyl-6,9-dihydro-5H-pyrrolo[3,2-d][1,2,4]triazolo[4,3-a]pyrimidin-5-one (0.015 g, 0.044 mmol). 2,4,6-trimethyl-1,3,5,2,4,6-trioxatriborinane (0.017 g, 0.133 mmol), Chloro(2-dicyclohexylphosphino-2',4',6'-triisopropyl-1,1'-biphenyl)[2-(2'-amino-1,1'-biphenyl)]palladium(II) (5.23 mg, 6.65 μmol), potassium phosphate tribasic (0.038 g, 0.177 mmol), 1,4-dioxane (0.5 ml), and water (0.1 ml) were sparged with $N_2$ for 5 minutes then stirred at 90° C. for two hours. The reaction mixture was cooled to room temperature and diluted with DMF (5 ml). Purification by preparative HPLC (pH 2, acetonitrile/water with TFA) afforded the product (5 mg, 42%). LCMS calculated for $C_{14}H_{20}N_5O$ (M+H): 274.2. Found: 274.2.

Example 15. 3-Methyl-9-pentyl-8-phenyl-6,9-dihydro-5H-pyrrolo[3,2-d][1,2,4]triazolo[4,3-a]pyrimidin-5-one

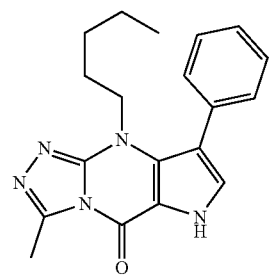 [SMILES: CCCCCn1c2c(-c3ccccc3)c[nH]c2c(=O)n2c(C)nnc12]

This compound was prepared using similar procedures as described in Example 14 using phenylboronic acid in place of 2,4,6-trimethyl-1,3,5,2,4,6-trioxatriborinane. LCMS calculated for $C_{19}H_{22}N_5O$ (M+H):336.2. Found: 336.1.

Example 16. 3-Methyl-5-oxo-9-pentyl-6,9-dihydro-5H-pyrrolo[3,2-d][1,2,4]triazolo[4,3-a]pyrimidine-8-carbonitrile

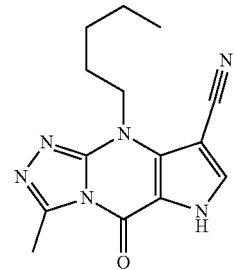 [SMILES: CCCCCn1c2c(C#N)c[nH]c2c(=O)n2c(C)nnc12]

In a sealed vial, a mixture of 8-bromo-3-methyl-9-pentyl-6,9-dihydro-5H-pyrrolo[3,2-d][1,2,4]triazolo[4,3-a]pyrimidin-5-one (from Example 13) (0.015 g, 0.044 mmol). potassium ferrocyanide (0.037 g, 0.089 mmol), [(2-Di-tert-butylphosphino-2',4',6'-triisopropyl-1,1'-biphenyl)-2-(2'-amino-1,1'-biphenyl)]palladium(II) methanesulfonate (8.8 mg, 11 μmol), potassium acetate (1.1 mg, 0.011 mmol), 1,4-dioxane (0.44 ml), and water (0.44 ml) were sparged with $N_2$ for 5 minutes, then stirred at 90° C. for two hours. The reaction mixture was cooled to room temperature and diluted with DMF (5 ml). Purification by preparative HPLC (pH 2, acetonitrile/water with TFA) afforded the product (5 mg, 38%). LCMS calculated for $C_{14}H_{17}N_6O$ (M+H): 285.1. Found: 285.0.

Example 17. 8-(1-Benzyl-1H-pyrazol-4-yl)-3-methyl-9-pentyl-6,9-dihydro-5H-pyrrolo[3,2-d][1,2,4]triazolo[4,3-a]pyrimidin-5-one

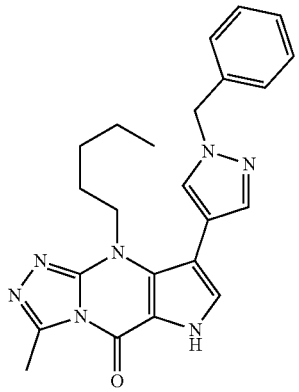 [SMILES: CCCCCn1c2c(-c3cnn(Cc4ccccc4)c3)c[nH]c2c(=O)n2c(C)nnc12]

This compound was prepared using similar procedures as described in Example 14 using 1-benzyl-4-(4,4,5,5-tetramethyl-1,3,2-dioxaborolan-2-yl)-1H-pyrazole in place of 2,4,6-trimethyl-1,3,5,2,4,6-trioxatriborinane. LCMS calculated for $C_{23}H_{26}N_7O$ (M+H): 416.2. Found: 416.2.

Example 18: 7-Methyl-4-pentyl-1H-imidazo[1,2-a]pyrrolo[3,2-d]pyrimidin-9(4H)-one

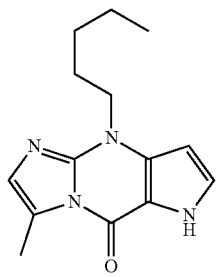 [SMILES: CCCCCn1c2cc[nH]c2c(=O)n2c(C)cnc12]

Step 1: 2-Amino-1-pentyl-1H-pyrrolo[3,2-d]pyrimidin-4(5H)-one

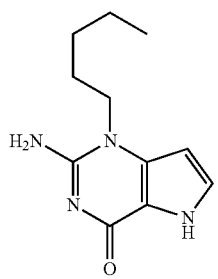 [SMILES: CCCCCn1c(N)nc(=O)c2[nH]ccc21]

To a solution of (E)-2-hydrazono-1-pentyl-1,2,3,5-tetrahydro-4H-pyrrolo[3,2-d]pyrimidin-4-one (from Example 1, Step 4) (1.5 g, 6.38 mmol) in acetic acid (22 ml) was added an aqueous solution of sodium nitrite (0.572 g, 8.29 mmol) (prepared by dissolving sodium nitrite into minimum amount of water) dropwise. The reaction mixture was allowed to stir overnight at room temperature. Zinc dust (2.92 g, 44.6 mmol) was added in portions, and the mixture was heated to 90 degrees Celsius for 7 hours. The reaction mixture was filtered. The solvent was concentrated, and the crude residue diluted with water. The product was allowed to precipitate out of the aqueous solution by stirring the suspension overnight. The solution was filtered to furnish the product as grey powder. LCMS calculated for $C_{11}H_{17}N_4O$ (M+H):221.1. Found: 221.1 Step 2: 7-Methyl-4-pentyl-1H-imidazo[1,2-a]pyrrolo[3,2-d]pyrimidin-9(4H)-one A vial was charged with 2-amino-1-pentyl-1H-pyrrolo[3,2-d]pyrimidin-4(5H)-one (0.7 g, 3.18 mmol), 2-bromopropanal (0.435 g, 3.18 mmol), triethylamine (1.329 ml, 9.53 mmol), and DMF (7.94 ml). The solution was sparged with $N_2$ for 5 minutes then heated to 100 degrees Celsius overnight. The solvent was removed under reduced pressure and the crude residue was dissolved into DCM/water. The layers were separated, and the aqueous layer was extracted three times with DCM. The combined organic fractions were dried over $MgSO_4$, filtered, and concentrated to furnish the desired product. (0.82 g, quant.). LCMS calculated for $C_{14}H_{19}N_4O$ (M+H):259.2. Found: 259.3.

Example 19. 3-Methyl-9-pentyl-7-(1-(1-(pyrimidin-2-yl)azetidin-3-yl)-1H-pyrazol-4-yl)-6,9-dihydro-5H-pyrrolo[3,2-d][1,2,4]triazolo[4,3-a]pyrimidin-5-one

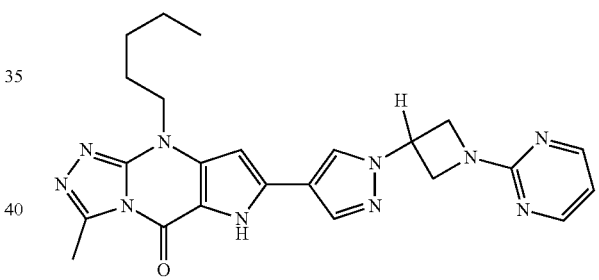

Step 1: Ethyl 3-(pentylamino)-1H-pyrrole-2-carboxylate

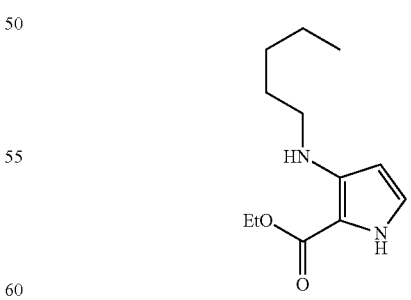

Ethyl 3-amino-1H-pyrrole-2-carboxylate (5 g, 32.4 mmol), pentanal (3.79 ml, 35.7 mmol), and sodium cyanoborohydride (2.038 g, 32.4 mmol) were mixed in methanol (64.9 ml) at room temperature overnight. The reaction mixture was concentrated under reduced pressure. The crude residue was purified by flash chromatography (0 to 100% EtOAc in hexanes) to give the desired product (4.4 g, 61%). LCMS calculated for $C_{12}H_{21}N_2O_2$ (M+H): 225.2. Found: 225.1.

Step 2: Ethyl 3-(3-(ethoxycarbonyl)-1-pentylthioureido)-1H-pyrrole-2-carboxylate

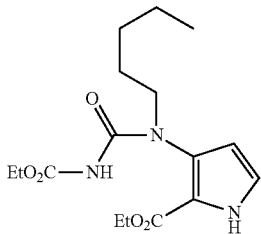 [SMILES: CCCCCN(C(=O)NC(=O)OCC)c1cc[nH]c1C(=O)OCC]

A vial was charged with ethyl 3-(pentylamino)-1H-pyrrole-2-carboxylate (4.4 g, 19.62 mmol), dichloromethane (39.2 ml), and ethoxycarbonyl isothiocyanate (2.78 ml, 23.54 mmol). The reaction mixture was stirred at room temperature overnight. The reaction mixture was quenched with water (40 ml), and the layers were separated. The aqueous layer was extracted with dichloromethane (3×40 mL), and the combined organic fractions were dried over MgSO₄, filtered, and concentrated. The crude material was used in the next step without further purification (7.3 g, quant.). LCMS calculated for $C_{16}H_{26}N_3O_4S$ (M+H): 356.2. Found: 356.1.

Step 3: 1-Pentyl-2-thioxo-2,3-dihydro-1H-pyrrolo[3,2-d]pyrimidin-4(5H)-one

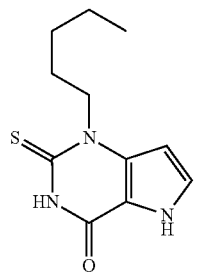 [SMILES: CCCCCn1c(=S)[nH]c(=O)c2[nH]ccc21]

A microwave vial was charged with ethyl 3-(3-(ethoxycarbonyl)-1-pentylthioureido)-1H-pyrrole-2-carboxylate (7.31 g, 20.57 mmol) and sodium ethoxide (21% w/w, 8.45 ml, 22.62 mmol) solution. The vial was capped and heated in a microwave reactor for 10 minutes at 120 degrees Celsius. The reaction mixture was brought to neutral pH on addition of 1M HCl solution and the solid product was filtered and dried (3.1 g, 64%). LCMS calculated for $C_{11}H_{16}N_3OS$ (M+H): 238.1. Found: 238.1.

Step 4: 2-Hydrazono-1-pentyl-2,3-dihydro-1H-pyrrolo[3,2-d]pyrimidin-4(5H)-one

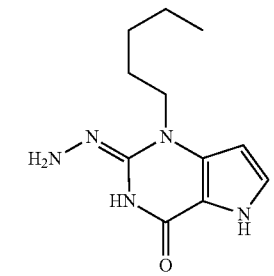 [SMILES: CCCCCn1/c(=N/N)[nH]c(=O)c2[nH]ccc21]

A vial was charged with 1-pentyl-2-thioxo-2,3-dihydro-1H-pyrrolo[3,2-d]pyrimidin-4(5H)-one (3.13 g, 13.19 mmol) and hydrazine hydrate (20 mL). The reaction mixture was stirred at 100 degrees Celsius overnight. The solid formed was filtered and washed with water to give the desired product (2.2 g, 70%). LCMS calculated for $C_{11}H_{19}8N_5O$ (M+H): 236.1. Found: 236.1.

Step 5: 3-Methyl-9-pentyl-6,9-dihydro-5H-pyrrolo[3,2-d][1,2,4]triazolo[4,3-a]pyrimidin-5-one

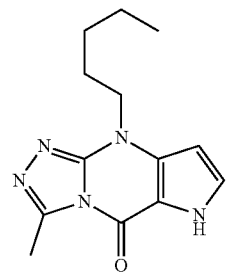 [SMILES: CCCCCn1c2cc[nH]c2c(=O)n2c(C)nnc12]

A vial was charged with (E)-2-hydrazono-1-pentyl-2,3-dihydro-1H-pyrrolo[3,2-d]pyrimidin-4(5H)-one (4.8 g, 20.40 mmol), a drop of trifluoroacetic acid, and triethyl orthoacetate (20 mL). The reaction mixture was heated to 110 degrees Celsius for three hours. The suspension was filtered, washed with hexanes, and dried to give the product (4.0 g, 76%). LCMS calculated for $C_{13}H_{18}N_5O$ (M+H): 260.1. Found: 260.2.

Step 6: 3-Methyl-9-pentyl-6-(phenylsulfonyl)-6,9-dihydro-5H-pyrrolo[3,2-d][1,2,4]triazolo[4,3-a]pyrimidin-5-one

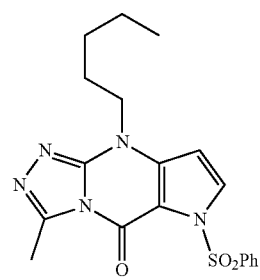

A vial was charged with 3-methyl-9-pentyl-6,9-dihydro-5H-pyrrolo[3,2-d][1,2,4]triazolo[4,3-a]pyrimidin-5-one (4 g, 15.43 mmol), dichloromethane (40 mL), dimethylaminopyridine (0.188 g, 1.543 mmol), triethylamine (3.23 ml, 23.14 mmol), and benzenesulfonyl chloride (2.187 ml, 16.97 mmol). The reaction mixture was stirred at room temperature for one hour. The reaction mixture was quenched with water, and the layers were separated. The aqueous layer was extracted with dichloromethane (3×40 mL), and the combined organic fractions were dried over MgSO$_4$, filtered, and concentrated. The crude material was used in the next step without further purification (6.1 g, quant.). LCMS calculated for $C_{19}H_{22}N_5O_3S$ (M+H): 400.1. Found: 400.1.

Step 7: 7-Bromo-3-methyl-9-pentyl-6-(phenylsulfonyl)-6,9-dihydro-5H-pyrrolo[3,2-d][1,2,4]triazolo[4,3-a]pyrimidin-5-one

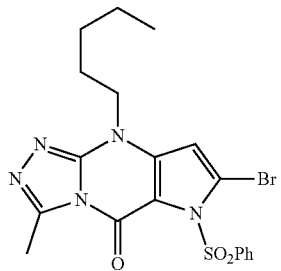

A vial was charged with 3-methyl-9-pentyl-6-(phenylsulfonyl)-6,9-dihydro-5H-pyrrolo[3,2-d][1,2,4]triazolo[4,3-a]pyrimidin-5-one (1 g, 2.503 mmol), dry THF (30 mL) and the mixture was cooled to −78 degrees Celsius. Lithium diisopropylamide solution (1M in hexanes/THF, 3.13 ml, 3.13 mmol) was added dropwise. The reaction mixture was maintained at −78° C. for 1.5 hours. A solution of 1,2-dibromo-1,1,2,2-tetrachloroethane (1.223 g, 3.75 mmol) in dry THF (3 ml) was added dropwise to the reaction mixture, and the reaction mixture was maintained at −78° C. for a further 1.5 hours. The reaction mixture was quenched with sat. aq. NH$_4$Cl solution (30 mL) and diluted with dichloromethane (30 mL). The layers were separated, and the aqueous layer was extracted with DCM (3×30 mL). The combined organic fractions were dried over MgSO$_4$, filtered, and concentrated. The crude residue was purified by flash chromatography (0 to 100% EtOAc in DCM) to give the desired product (0.84 g, 70%). LCMS calculated for $C_{19}H_{21}BrN_5O_3S$ (M+H): 478.1. Found: 478.1.

Step 8: 7-Bromo-3-methyl-9-pentyl-6,9-dihydro-5H-pyrrolo[3,2-d][1,2,4]triazolo[4,3-a]pyrimidin-5-one

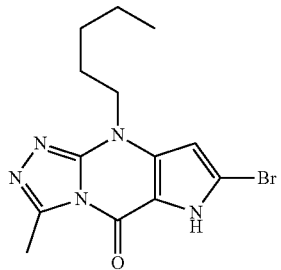 [SMILES: CCCCCn1c2cc(Br)[nH]c2c(=O)n2c(C)nnc12]

TBAF (1.0 M in THF) (2.0 ml, 2.0 mmol) was added to a solution of 7-bromo-3-methyl-9-pentyl-6-(phenylsulfonyl)-6,9-dihydro-5H-pyrrolo[3,2-d][1,2,4]triazolo[4,3-a]pyrimidin-5-one (0.360 g, 0.753 mmol) in THF (4.0 ml), and then the reaction was stirred at 50° C. for 1 h. The solvent was removed and the product was purified by column chromatography eluting with CH$_2$Cl$_2$/MeOH (max. MeOH 10%). LCMS calculated for $C_{13}H_{17}BrN_5O$ (M+H)+: m/z=338.1; found 338.1.

Step 9: tert-Butyl 3-(4-(3-methyl-5-oxo-9-pentyl-6,9-dihydro-5H-pyrrolo[3,2-d][1,2,4]triazolo[4,3-a]pyrimidin-7-yl)-1H-pyrazol-1-yl)azetidine-1-carboxylate

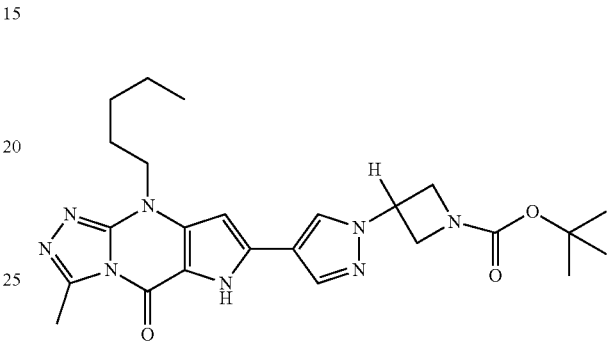

A mixture of 7-bromo-3-methyl-9-pentyl-6,9-dihydro-5H-pyrrolo[3,2-d][1,2,4]triazolo[4,3-a]pyrimidin-5-one (0.200 g, 0.591 mmol), tert-butyl 3-(4-(4,4,5,5-tetramethyl-1,3,2-dioxaborolan-2-yl)-1H-pyrazol-1-yl)azetidine-1-carboxylate (0.248 g, 0.710 mmol), dichloro[1,1'-bis(dicyclohexylphosphino)ferrocene]palladium(II), dichloromethane adduct (Pd-127) (0.045 g, 0.059 mmol) and cesium fluoride (0.449 g, 2.96 mmol) in t-BuOH (4 ml)/Water (1.5 ml) was vacuumed and replaced with N$_2$ for 3 times. The reaction was stirred at 105° C. for 3 h. The mixture was diluted with ethyl acetate and washed with water, dried and concentrated. The product was purified by column eluting with CH$_2$Cl$_2$/MeOH (max. MeOH 10%). LCMS calculated for $C_{24}H_{33}N_8O_3$ (M+H)+: m/z=481.3; found 481.3.

Step 10: 7-(1-(Azetidin-3-yl)-1H-pyrazol-4-yl)-3-methyl-9-pentyl-6,9-dihydro-5H-pyrrolo[3,2-d][1,2,4]triazolo[4,3-a]pyrimidin-5-one

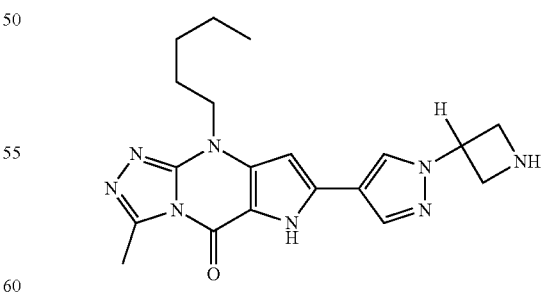

TFA (1.0 ml) was added to a solution of tert-butyl 3-(4-(3-methyl-5-oxo-9-pentyl-6,9-dihydro-5H-pyrrolo[3,2-d][1,2,4]triazolo[4,3-a]pyrimidin-7-yl)-1H-pyrazol-1-yl)azetidine-1-carboxylate (100.0 mg, 0.208 mmol) in CH$_2$Cl$_2$ (1.0 ml) and then the reaction was stirred at room temperature for 30 min. The solvent was removed to provide the crude product as a TFA salt. LCMS calculated for C$_{19}$H$_{25}$N$_5$O (M+H)+: m/z=381.2; found 381.2.

Step 11: 3-Methyl-9-pentyl-7-(1-(1-(pyrimidin-2-yl)azetidin-3-yl)-H-pyrazol-4-yl)-6,9-dihydro-5H-pyrrolo[3,2-d][1,2,4]triazolo[4,3-a]pyrimidin-5-one 2-Chloropyrimidine (9.03 mg, 0.079 mmol) was added to a solution of 7-(1-(azetidin-3-yl)-1H-pyrazol-4-yl)-3-methyl-9-pentyl-6,9-dihydro-5H-pyrrolo[3,2-d][1,2,4]triazolo[4,3-a]pyrimidin-5-one (10.0 mg, 0.026 mmol) and triethylamine (0.022 ml, 0.158 mmol) in DMF (0.8 ml), and then the reaction was stirred at room temperature overnight. The mixture was diluted with acetonitrile/water and purified by prep HPLC (pH 2, acetonitrile/water with TFA) to provide the desired compound as its TFA salt. $^1$H NMR (500 MHz, DMSO) δ 12.54 (s, 1H), 8.58 (s, 1H), 8.43 (d, J=4.8 Hz, 2H), 8.20 (s, 1H), 6.78 (t, J=4.8 Hz, 1H), 6.68 (d, J=2.3 Hz, 1H), 5.55-5.18 (m, 1H), 4.66-4.45 (m, 2H), 4.42-4.25 (dd, J=9.5, 5.3 Hz, 2H), 4.16 (t, J=7.4 Hz, 2H), 2.79 (s, 3H), 1.91-1.73 (m, 2H), 1.49-1.21 (m, 4H), 0.97-0.74 (m, 3H). LC-MS calculated for C$_{23}$H$_{27}$N$_{10}$O (M+H)+: m/z=459.2; found 459.2.

Example 20. 2-(3-(4-(3-Methyl-5-oxo-9-pentyl-6,9-dihydro-5H-pyrrolo[3,2-d][1,2,4]triazolo[4,3-a]pyrimidin-7-yl)-1H-pyrazol-1-yl)azetidin-1-yl)pyrimidine-4-carbonitrile

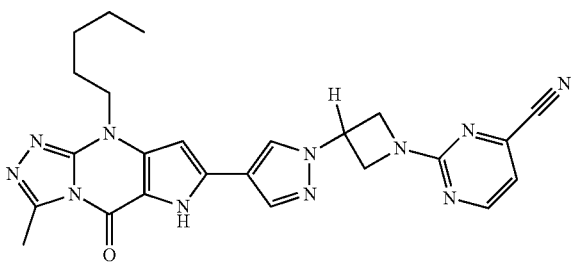 [SMILES: CCCCCn1c2cc(-c3cnn(C4CN(c5nccc(C#N)n5)C4)c3)[nH]c2c(=O)n2c(C)nnc12]

This compound was prepared using a similar procedure as described for Example 19, replacing 2-chloropyrimidine with 2-chloropyrimidine-4-carbonitrile in Step 11. LC-MS calculated for C$_{24}$H$_{26}$N$_{11}$O (M+H)+: m/z=484.2; found 484.2.

Example 21. 7-(1-(1-(4-Aminopyrimidin-2-yl)azetidin-3-yl)-1H-pyrazol-4-yl)-3-methyl-9-pentyl-6,9-dihydro-5H-pyrrolo[3,2-d][1,2,4]triazolo[4,3-a]pyrimidin-5-one

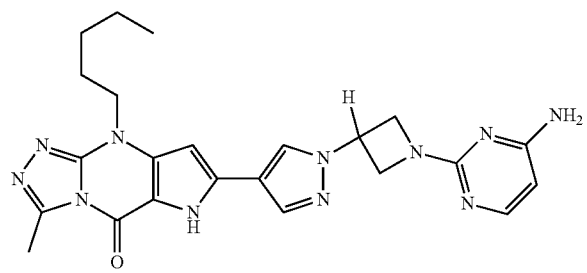 [SMILES: CCCCCn1c2cc(-c3cnn(C4CN(c5nccc(N)n5)C4)c3)[nH]c2c(=O)n2c(C)nnc12]

2-Chloropyrimidin-4-amine (3.40 mg, 0.026 mmol) was added to a solution of 7-(1-(azetidin-3-yl)-1H-pyrazol-4-yl)-3-methyl-9-pentyl-6,9-dihydro-5H-pyrrolo[3,2-d][1,2,4]triazolo[4,3-a]pyrimidin-5-one (from Example 19, Step 3) (10.0 mg, 0.026 mmol) and triethylamine (0.022 ml, 0.157 mmol) in DMSO (0.5 ml), and then the reaction was stirred at 130° C. for 1 h. The mixture was diluted with acetonitrile/water and purified by prep HPLC (pH 2, acetonitrile/water with TFA) to provide the desired compound as a TFA salt. LC-MS calculated for C$_{23}$H$_{28}$N$_{11}$O (M+H)+: m/z=474.2; found 474.2.

Example 22. 7-(1-(1-(4-(2-Hydroxyethylamino)pyrimidin-2-yl)azetidin-3-yl)-1H-pyrazol-4-yl)-3-methyl-9-pentyl-6,9-dihydro-5H-pyrrolo[3,2-d][1,2,4]triazolo[4,3-a]pyrimidin-5-one

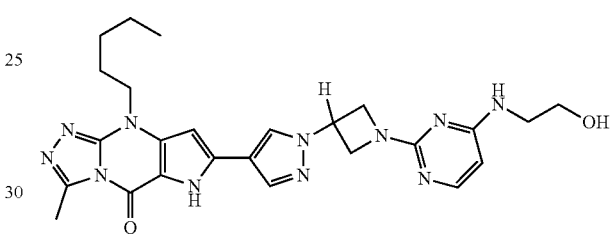

This compound was prepared using a similar procedure as described for Example 21, replacing 2-chloropyrimidin-4-amine with 2-((2-chloropyrimidin-4-yl)amino)ethan-1-ol. LC-MS calculated for C$_{25}$H$_{32}$N$_1$O$_2$ (M+H)+: m/z=518.3; found 518.3.

Example 23. 3-Methyl-7-(1-(1-(4-(methylamino)pyrimidin-2-yl)azetidin-3-yl)-1H-pyrazol-4-yl)-9-pentyl-6,9-dihydro-5H-pyrrolo[3,2-d][1,2,4]triazolo[4,3-a]pyrimidin-5-one

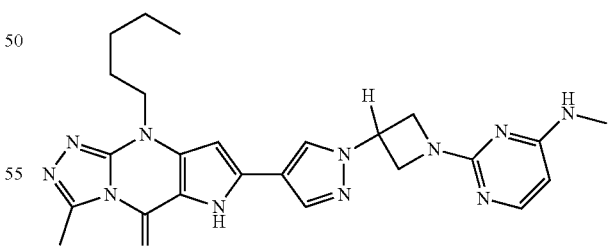

This compound was prepared using a similar procedure as described for Example 21, replacing 2-chloropyrimidin-4-amine with 2-chloro-N-methylpyrimidin-4-amine. LC-MS calculated for C$_{24}$H$_{30}$N$_{11}$O (M+H)+: m/z=488.3; found 488.3.

Example 24. 9-Butyl-3-methyl-7-(1-(1-(pyrimidin-2-yl)azetidin-3-yl)-1H-pyrazol-4-yl)-6,9-dihydro-5H-pyrrolo[3,2-d][1,2,4]triazolo[4,3-a]pyrimidin-5-one

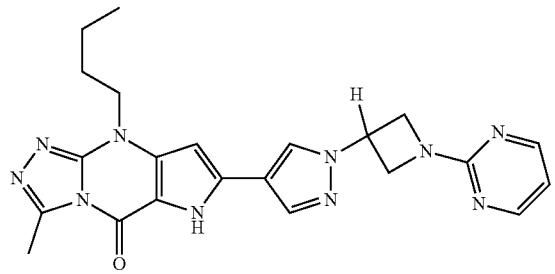 [SMILES: CCCCn1c2cc(-c3cnn(C4CN(c5ncccn5)C4)c3)[nH]c2c(=O)n2c(C)nnc12]

Step 1: 7-(1-(Azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one

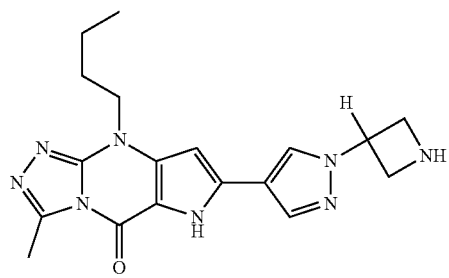 [SMILES: CCCCn1c2cc(-c3cnn(C4CNC4)c3)[nH]c2c(=O)n2c(C)nnc12]

This compound was prepared using a similar procedure as described for Example 19 Step 1 to 10, replacing pentanal with butyraldehyde in Step 1. LC-MS calculated for $C_{18}H_{23}N_8O$ (M+H): m/z=367.2; found 367.2.

Step 2: 9-Butyl-3-methyl-7-(1-(1-(pyrimidin-2-yl)azetidin-3-yl)-1H-pyrazol-4-yl)-6,9-dihydro-5H-pyrrolo[3,2-d][1,2,4]triazolo[4,3-a]pyrimidin-5-one 2-Chloropyrimidine (9.38 mg, 0.082 mmol) was added to a solution of 7-(1-(azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one (10.0 mg, 0.027 mmol) and triethylamine (0.023 ml, 0.164 mmol) in DMF (0.8 ml), and then the reaction was stirred at 70° C. for 1 h. The mixture was diluted with acetonitrile/water and purified by prep HPLC (pH 2, acetonitrile/water with TFA) to provide the desired compound as its TFA salt. LC-MS calculated for $C_{22}H_{25}N_{10}O$ (M+H)+: m/z=445.2; found 445.2.

Example 25. 2-(3-(4-(9-Butyl-3-methyl-5-oxo-6,9-dihydro-5H-pyrrolo[3,2-d][1,2,4]triazolo[4,3-a]pyrimidin-7-yl)-1H-pyrazol-1-yl)azetidin-1-yl)pyrimidine-4-carbonitrile

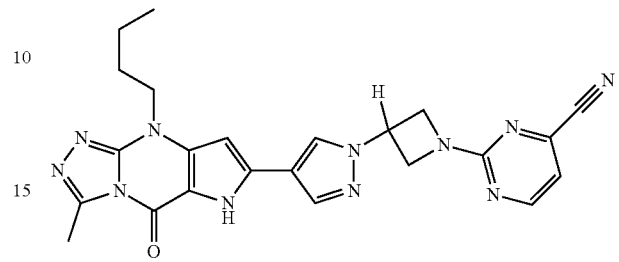

2-Chloropyrimidine-4-carbonitrile (11.42 mg, 0.082 mmol) was added to a solution of 7-(1-(azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one (10.0 mg, 0.027 mmol) and triethylamine (0.023 ml, 0.164 mmol) in DMF (0.8 ml), and then the reaction was stirred at room temperature for 3 h. The mixture was diluted with acetonitrile/water and purified by prep HPLC (pH 2, acetonitrile/water with TFA) to provide the desired compound as its TFA salt. LC-MS calculated for $C_{23}H_{24}N_{11}O$ (M+H)+: m/z=470.2; found 470.1.

Example 26. 9-Butyl-3-methyl-7-(1-(1-(4-methylpyrimidin-2-yl)azetidin-3-yl)-1H-pyrazol-4-yl)-6,9-dihydro-5H-pyrrolo[3,2-d][1,2,4]triazolo[4,3-a]pyrimidin-5-one

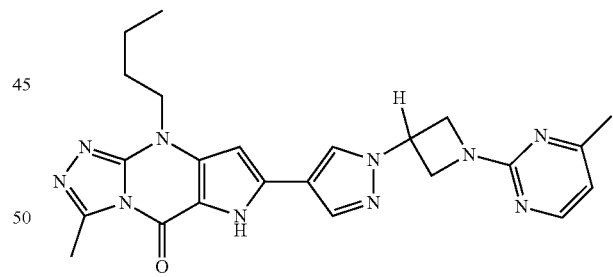

2-Chloro-4-methylpyrimidine (10.5 mg, 0.082 mmol) was added to a solution of 7-(1-(azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one (10.0 mg, 0.027 mmol) and triethylamine (0.023 ml, 0.164 mmol) in DMSO (0.50 ml), and then the reaction was stirred at 70° C. for 2 h. The mixture was diluted with acetonitrile/water and purified by prep HPLC (pH 2, acetonitrile/water with TFA) to provide the desired compound as its TFA salt. LC-MS calculated for $C_{23}H_{27}N_{10}O$ (M+H)+: m/z=459.2; found 459.2.

Example 27. 9-Butyl-7-(1-(1-(4-methoxypyrimidin-2-yl)azetidin-3-yl)-1H-pyrazol-4-yl)-3-methyl-6,9-dihydro-5H-pyrrolo[3,2-d][1,2,4]triazolo[4,3-a]pyrimidin-5-one

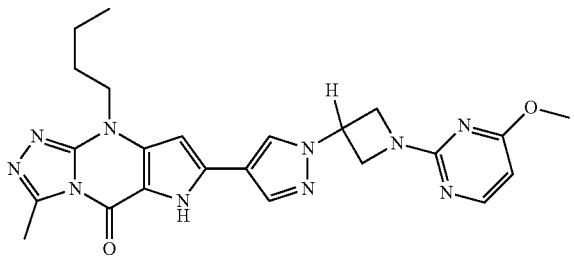 [SMILES: CCCCn1c2cc(-c3cnn(C4CN(c5nccc(OC)n5)C4)c3)[nH]c2c(=O)n2c(C)nnc12]

This compound was prepared using a similar procedure as described for Example 26 replacing 2-chloro-4-methylpyrimidine with 2-chloro-4-methoxypyrimidine. LC-MS calculated for $C_{23}H_{27}N_{10}O_2$(M+H)+: m/z=475.2; found 475.2.

Example 28. 7-(1-(1-(4-Aminopyrimidin-2-yl)azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one

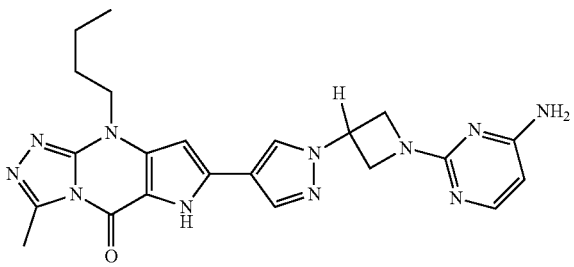 [SMILES: CCCCn1c2cc(-c3cnn(C4CN(c5nccc(N)n5)C4)c3)[nH]c2c(=O)n2c(C)nnc12]

2-Chloropyrimidin-4-amine (10.61 mg, 0.082 mmol) was added to a solution of 7-(1-(azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one (10.0 mg, 0.027 mmol) and triethylamine (0.023 ml, 0.164 mmol) in DMSO (0.5 ml), and then the reaction was stirred at 130° C. for 1 h. The mixture was diluted with acetonitrile/water and purified by prep HPLC (pH 2, acetonitrile/water with TFA) to provide the desired compound as its TFA salt. LC-MS calculated for $C_{22}H_{26}N_{11}O$ (M+H)+: m/z=460.2; found 460.2.

Example 29. 7-(1-(1-(4-Amino-5-fluoropyrimidin-2-yl)azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one

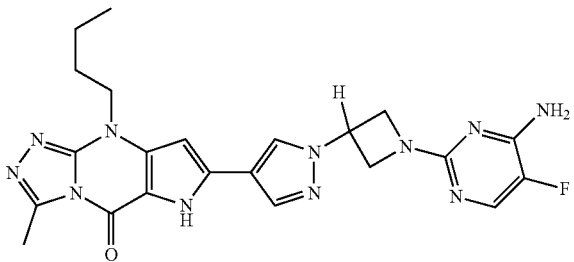 [SMILES: CCCCn1c2cc(-c3cnn(C4CN(c5ncc(F)c(N)n5)C4)c3)[nH]c2c(=O)n2c(C)nnc12]

This compound was prepared using a similar procedure as described for Example 28 replacing 2-chloropyrimidin-4-amine with 2-chloro-5-fluoropyrimidin-4-amine. LC-MS calculated for $C_{22}H_{25}FN_{11}O$ (M+H)+: m/z=478.2; found 478.2.

Example 30. 7-(1-((2-(2-(Dimethylamino)acetyl)-1,2,3,4-tetrahydroisoquinolin-6-yl)methyl)-1H-pyrazol-4-yl)-3-methyl-9-pentyl-6,9-dihydro-5H-pyrrolo[3,2-d][1,2,4]triazolo[4,3-a]pyrimidin-5-one

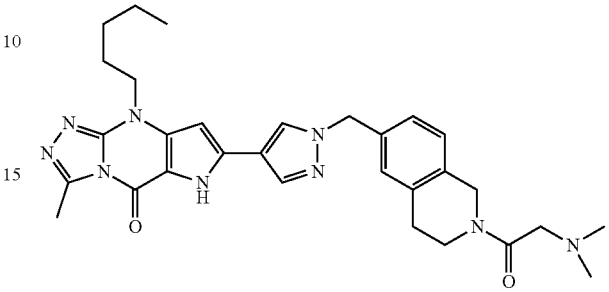

Step 1: tert-Butyl 6-((4-(4,4,5,5-tetramethyl-1,3,2-dioxaborolan-2-yl)-1H-pyrazol-1-yl)methyl)-3,4-dihydroisoquinoline-2(1H)-carboxylate

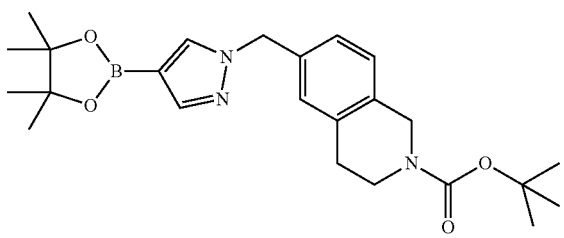 [SMILES: CC(C)(C)OC(=O)N1CCc2cc(Cn3cc(B4OC(C)(C)C(C)(C)O4)cn3)ccc2C1]

A flask was charged with 4-(4,4,5,5-tetramethyl-1,3,2-dioxaborolan-2-yl)-1H-pyrazole (0.5 g, 2.58 mmol), tert-butyl 6-(hydroxymethyl)-3,4-dihydroisoquinoline-2(1H)-carboxylate (0.339 g, 1.288 mmol), triphenylphosphine (0.743 g, 2.83 mmol), and THF (12 ml). The solution was cooled to 0° C. and DIAD (0.601 ml, 3.09 mmol) was added dropwise. The reaction mixture was stirred overnight at room temperature. The mixture was diluted with ethyl acetate and washed with water, dried and concentrated. The product was purified by column chromatography eluting with Hexane/EtOAc (max. EtOAc 60%) to afford the product. LCMS calculated for $C_{24}H_{35}BN_3O_4$(M+H)+: m/z=440.3; found 440.3.

Step 2: tert-Butyl 6-((4-(3-methyl-5-oxo-9-pentyl-6,9-dihydro-5H-pyrrolo[3,2-d][1,2,4]triazolo[4,3-a]pyrimidin-7-yl)-1H-pyrazol-1-yl)methyl)-3,4-dihydroisoquinoline-2(1H)-carboxylate

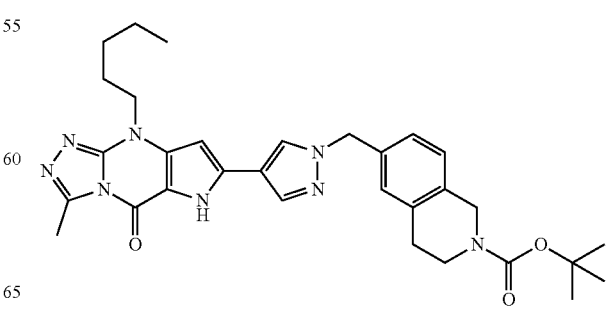

A mixture of 7-bromo-3-methyl-9-pentyl-6,9-dihydro-5H-pyrrolo[3,2-d][1,2,4]triazolo[4,3-a]pyrimidin-5-one (from Example 19, Step 8) (0.040 g, 0.118 mmol), tert-butyl 6-((4-(4,4,5,5-tetramethyl-1,3,2-dioxaborolan-2-yl)-1H-pyrazol-1-yl)methyl)-3,4-dihydroisoquinoline-2(1H)-carboxylate (0.062 g, 0.142 mmol), dichloro[1,1'-bis(dicyclohexylphosphino)ferrocene]palladium(II), dichloromethane adduct (Pd-127) (8.94 mg, 0.012 mmol) and cesium fluoride (0.090 g, 0.591 mmol) in t-BuOH (1.5 ml)/Water (0.6 ml) was vacuumed and replaced with $N_2$ for 3 times. The reaction was then stirred at 105° C. for 2 h, cooled to rt, diluted with ethyl acetate, washed with water, dried and concentrated. The product was purified by column eluting with $CH_2Cl_2$/MeOH (max. MeOH 10%). LCMS calculated for $C_{31}H_{39}N_5O_3$ (M+H)+: m/z=571.3; found 571.5.

Step 3: 3-Methyl-9-pentyl-7-(1-((1,2,3,4-tetrahydroisoquinolin-6-yl)methyl)-1H-pyrazol-4-yl)-6,9-dihydro-5H-pyrrolo[3,2-d][1,2,4]triazolo[4,3-a]pyrimidin-5-one

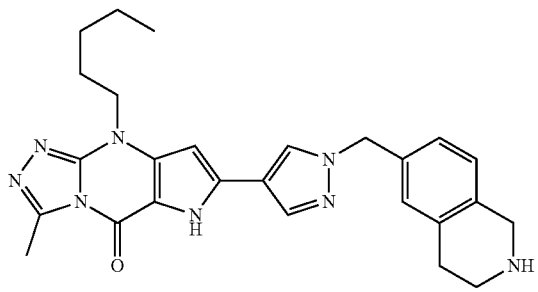 [SMILES: CCCCCn1c2cc(-c3cnn(Cc4ccc5c(c4)CCNC5)c3)[nH]c2c(=O)n2c(C)nnc12]

TFA (0.5 ml, 6.49 mmol) was added to a solution of tert-butyl 6-((4-(3-methyl-5-oxo-9-pentyl-6,9-dihydro-5H-pyrrolo[3,2-d][1,2,4]triazolo[4,3-a]pyrimidin-7-yl)-1H-pyrazol-1-yl)methyl)-3,4-dihydroisoquinoline-2(1H)-carboxylate (50.0 mg, 0.088 mmol) in $CH_2Cl_2$ (0.5 ml), and then the reaction was stirred at room temperature for 30 min. The solvent was then removed to provide the crude product as TFA salt. LCMS calculated for $C_{26}H_{31}N_5O$ (M+H)+: m/z=471.3; found 471.2.

Step 4: 7-(1-((2-(2-(Dimethylamino)acetyl)-1,2,3,4-tetrahydroisoquinolin-6-yl)methyl)-1H-pyrazol-4-yl)-3-methyl-9-pentyl-6,9-dihydro-5H-pyrrolo[3,2-d][1,2,4]triazolo[4,3-a]pyrimidin-5-one Dimethylglycinoyl chloride (3.10 mg, 0.026 mmol) was added to a solution of 3-methyl-9-pentyl-7-(1-((1,2,3,4-tetrahydroisoquinolin-6-yl)methyl)-1H-pyrazol-4-yl)-6,9-dihydro-5H-pyrrolo[3,2-d][1,2,4]triazolo[4,3-a]pyrimidin-5-one (6.0 mg, 0.013 mmol) and triethylamine (8.89 μl, 0.064 mmol) in $CH_2Cl_2$ (0.8 ml) at room temperature and stirred for 30 min. The solvent was removed, and the mixture was diluted with acetonitrile/water and purified by prep HPLC (pH 2, acetonitrile/water with TFA) to provide the desired compound as its TFA salt. LC-MS calculated for $C_{30}H_{38}N_9O_2$ (M+H)+: m/z=556.3; found 556.3.

Example A. Adenosine A2A Receptor Cyclic AMP GS Assay

Stably transfected HEK-293 cells expressing the human adenosine A2A receptor (Perkin Elmer) are maintained in MEM culture medium with 10% FBS and 400 μg/ml Geneticin (Life Technologies). 18 to 24 hours prior to assay, geneticin is removed from culture. The cisbio cAMP-GS Dynamic kit utilizing the FRET (Fluorescence Resonance Energy Transfer) technology is used to measure cAMP accumulation in the cells. Compounds of the present disclosure at an appropriate concentration are mixed with 10000 cells/well in white 96 well half area plates (Perkin Elmer) for 30 min at room temperature gently shaking. Agonist, CGS21680 (R&D Technologies) at 4 nM is added to each well for 60 min at room temperature gently shaking. Detection reagents, d2-labeled cAMP (acceptor) and anti-cAMP cryptate (donor) are added to each well for 60 min at room temperature gently shaking. Plates are read on Pherastar (BMG Labtech), fluorescence ratio 665/620 is calculated and $EC_{50}$ determination is performed by fitting the curve of percent of control versus the log of the compound concentration using GraphPad Prism.

Example B. Adenosine A2B Receptor Cyclic AMP GS Assay

Stably transfected HEK-293 cells expressing the human adenosine A2B receptor (Perkin Elmer) were maintained in MEM culture medium with 10% FBS and 100 μg/ml Geneticin (Life Technologies). 18 to 24 hours prior to assay, geneticin was removed from culture. The cisbio cAMP-GS Dynamic kit utilizing the FRET (Fluorescence Resonance Energy Transfer) technology was used to measure cAMP accumulation in the cells. Compounds of the present disclosure at an appropriate concentration were mixed with 10000 cells/well in white 96 well half area plates (Perkin Elmer) for 30 min at room temperature gently shaking. Agonist, NECA (R&D Technologies) at 12 nM was added to each well for 60 min at room temperature gently shaking. Detection reagents, d2-labeled cAMP (acceptor) and anti-cAMP cryptate (donor) were added to each well for 60 min at RT gently shaking. Plates were read on Pherastar (BMG Labtech), fluorescence ratio 665/620 was calculated and $EC_{50}$ determination was performed by fitting the curve of percent of control versus the log of the compound concentration using GraphPad Prism. The $EC_{50}$ data for the Examples obtained via this method are shown in Table 1.

Example C. A2A Tag-Lite® HTRF Assay

Assays were conducted in black low volume 384-well polystyrene plates (Greiner 784076-25) in a final volume of 10 μL. Test compounds were first serially diluted in DMSO and 100 nl added to the plate wells before the addition of other reaction components. The final concentration of DMSO was 1%. Tag-lite® Adenosine A2A labeled cells (CisBio C1TT1A2A) were diluted 1:5 into Tag-lite buffer (CisBio LABMED) and spun 1200 g for 5 mins. The pellet was resuspended at a volume 10.4× the initial cell suspension volume in Tag-lite buffer, and Adenosine A2A Receptor Red antagonist fluorescent ligand (CisBio L0058RED) added at 12.5 nM final concentration. 10 ul of the cell and ligand mix was added to the assay wells and incubated at room temperature for 45 minutes before reading on a PHERAstar FS plate reader (BMG Labtech) with HTRF 337/620/665 optical module. Percent binding of the fluorescent ligand was calculated; where 100 nM of A2A antagonist control ZM 241385 (Tocris 1036) displaces the ligand 100% and 1% DMSO has 0% displacement. The % binding data versus the log of the inhibitor concentration was fitted to a one-site competitive binding model (Graph- Pad Prism version 7.02) where the ligand constant=12.5 nM and the ligand Kd=1.85 nM. The $K_i$ data for the Examples obtained via this method are shown in Table 1.

Example D. A2B Filter Binding Assay

Assays are conducted in deep well polypropylene plates (Greiner 786201) in a final volume of 550 µL. Test compounds are first serially diluted in DMSO and 5.5 ul is then added to the plate wells before the addition of other reaction components. The final concentration of DMSO is 3%. HEK293 cell membranes overexpressing the human adenosine receptor A2B (Perkin Elmer ES-113-M400UA) are diluted to 40 µg/ml in 50 mM HEPES pH 7.0, 5 mM $MgCl_2$, 1 mM EDTA (Assay buffer). [3H] 8-cyclopentyl-1,3-dipropylxanthine (Perkin Elmer NET974001MC) is diluted in assay buffer+22% DMSO to 24.2 nM, and then further diluted to 1 nM by addition to the diluted membranes. 545 µl of the membrane and ligand mix is added to the assay wells and incubated on a shaker at room temperature for 1 hour. The membrane mix is then filtered over a UniFilter GF/C filter plate (Perkin Elmer 6005174) pre-soaked in 50 mM HEPES pH 6.5, 5 mM $MgCl_2$, 1 mM EDTA 0.5% BSA and then washed with 5 ml ice cold 50 mM HEPES pH 6.5, 5 mM $MgCl_2$, 1 mM EDTA 0.2% BSA. 50 µl MicroScint™ cocktail (Perkin Elmer 6013621) is added and plates are read on a Topcount NXT FS (Perkin Elmer). Percent binding of the [3H] ligand is calculated, where 1000 nM of LUF 5834 (Tocris 4603) control displaces the ligand 100% and 3% DMSO has 0% displacement. The % binding data versus the log of the inhibitor concentration is fitted to a one-site competitive binding model (GraphPad Prism version 7.02) where the ligand constant=2 nM and the ligand Kd=13 nM.

Example E. A1 and A3 SPA Binding Assays

Both assays are conducted in white 384-well polystyrene plates (Greiner 781075) in a final volume of 50 µL. Inhibitors are first serially diluted in DMSO and 100 nL is added to the plate wells before the addition of other reaction components. The final concentration of DMSO is 2%.

Wheatgerm agglutinin-coated yttrium silicate SPA beads (Perkin Elmer RPNQ0023) and CHO-K1 cell membranes overexpressing each human adeonsine receptor are incubated in 50 mM HEPES pH 7.0, 5 mM $MgCl_2$, 1 mM EDTA (Assay buffer) on a rotary stirrer for 2 hours at 4° C. The beads are pelleted by centrifugation at 6000 g for one minute, and then the supernatant with unbound membrane is discarded. The beads are re-suspended to the original volume in assay buffer. Each radioligand is diluted in assay buffer+22% DMSO at 12.2× the final concentration, and then added to the SPA bead suspension. 50 µl of the SPA bead reaction mix is added to the assay wells and the plates shaken at 600 rpm for 1 hour at room temperature. The beads are then allowed to settle for 1 hour before reading on a Topcount NXT FS (Perkin Elmer). Percent binding of the radiolabeled ligand is calculated, where a control at >100× Ki displaces the ligand 100% and 2% DMSO has 0% displacement. The % binding data versus the log of the inhibitor concentration is fitted to a one-site competitive binding model (GraphPad Prism version 7.02). Assay conditions are provided in the table below.

| Assay Component | A1 | A3 |
|---|---|---|
| SPA beads in Hepes buffer | 3 mg/ml | 1.25 mg/ml |
| Membrane | 60 µg/ml Perkin Elmer ES-010 | 20 µg/ml Perkin Elemer ES-012 |
| Radioligand | 1 nM [3H] DP-CPX (Perkin Elmer NET974) $K_D$ = 1 nM | 0.1 nM [125I] MECA (Perkin Elmer NEX312) $K_D$ = 0.8 nM |
| Control | 1 µM DPCPX (Tocris 0439) | 0.1 µM IB-MECA (Tocris 1066) |

The $A_{2A}\_K_i$ data and $A_{2B}\_cAMP\_EC_{50}$ data as measured according to the assays in Examples B and C are provided below. The symbol "†" indicates $A_{2A}\_K_i$ or $A_{2B}\_cAMP\_EC_{50}$≤10 nM, "††" indicates $A_{2A}\_K_i$ or $A_{2B}\_cAMP\_EC_{50}$>10 nM but ≤100 nM. "†††" indicates $A_{2A}\_K_i$ or $A_{2B}\_cAMP\_EC_{50}$>100 nM but ≤1 µM; and "††††" indicates $A_{2A}\_K_i$ or $A_{2B}\_cAMP\_EC_{50}$ is greater than 1 µM.

TABLE 1

| Ex. No. | $A_{2A}\_K_i$ (nM) | $A_{2B}\_cAMP\_EC_{50}$ (nM) |
|---|---|---|
| 1 | ††† | N/A |
| 2 | † | †† |
| 3 | † | † |
| 4 | † | † |
| 5 | † | †† |
| 6 | † | †† |
| 7 | † | †† |
| 8 | † | †† |
| 9 | † | †† |
| 10 | † | N/A |
| 11 | †† | N/A |
| 12 | † | † |
| 13 | †† | N/A |
| 14 | ††† | N/A |
| 15 | ††† | N/A |
| 16 | ††† | N/A |
| 17 | ††† | N/A |
| 18 | †† | N/A |
| 19 | † | †† |
| 20 | † | †† |
| 21 | † | †† |
| 22 | † | †† |
| 23 | † | †† |
| 24 | † | †† |
| 25 | † | †† |
| 26 | † | †† |
| 27 | † | †† |
| 28 | † | †† |
| 29 | † | †† |
| 30 | † | † |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound, selected from:
   3-methyl-9-pentyl-6,9-dihydro-5H-pyrrolo[3,2-d][1,2,4] triazolo[4,3-a]pyrimidin-5-one;
   7-(1-((5-chloropyridin-3-yl)methyl)-1H-pyrazol-4-yl)-3-methyl-9-pentyl-6,9-dihydro-5H-pyrrolo[3,2-d][1,2,4] triazolo[4,3-a]pyrimidin-5-one;
   3-methyl-7-(1-((5-methylpyridin-3-yl)methyl)-1H-pyrazol-4-yl)-9-pentyl-6,9-dihydro-5H-pyrrolo[3,2-d][1,2,4]triazolo[4,3-a]pyrimidin-5-one;

3-methyl-9-pentyl-7-(1-(thieno[3,2-b]pyridin-6-ylmethyl)-1H-pyrazol-4-yl)-6,9-dihydro-5H-pyrrolo[3,2-d][1,2,4]triazolo[4,3-a]pyrimidin-5-one;
7-(1-(imidazo[1,2-a]pyridin-7-ylmethyl)-1H-pyrazol-4-yl)-3-methyl-9-pentyl-6,9-dihydro-5H-pyrrolo[3,2-d][1,2,4]triazolo[4,3-a]pyrimidin-5-one;
7-(1-(((1,5-naphthyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one;
3-methyl-7-(1-((1-methyl-1H-pyrazolo[4,3-b]pyridin-6-yl)methyl)-1H-pyrazol-4-yl)-9-pentyl-6,9-dihydro-5H-pyrrolo[3,2-d][1,2,4]triazolo[4,3-a]pyrimidin-5-one;
3-methyl-9-pentyl-7-(1-(pyridin-3-ylmethyl)-1H-pyrazol-4-yl)-6,9-dihydro-5H-pyrrolo[3,2-d][1,2,4]triazolo[4,3-a]pyrimidin-5-one;
7-(1-((5-fluoropyridin-3-yl)methyl)-1H-pyrazol-4-yl)-3-methyl-9-pentyl-6,9-dihydro-5H-pyrrolo[3,2-d][1,2,4]triazolo[4,3-a]pyrimidin-5-one;
7-(1-benzyl-1H-pyrazol-4-yl)-3-methyl-9-pentyl-6,9-dihydro-5H-pyrrolo[3,2-d][1,2,4]triazolo[4,3-a]pyrimidin-5-one;
4-(3-methyl-5-oxo-9-pentyl-6,9-dihydro-5H-pyrrolo[3,2-d][1,2,4]triazolo[4,3-a]pyrimidin-7-yl)-N-p-tolylbenzenesulfonamide;
7-(1-(((1,5-naphthyridin-3-yl)methyl)-1H-pyrazol-4-yl)-9-pentyl-3-(trifluoromethyl)-6,9-dihydro-5H-pyrrolo[3,2-d][1,2,4]triazolo[4,3-a]pyrimidin-5-one;
8-bromo-3-methyl-9-pentyl-6,9-dihydro-5H-pyrrolo[3,2-d][1,2,4]triazolo[4,3-a]pyrimidin-5-one;
3,8-dimethyl-9-pentyl-6,9-dihydro-5H-pyrrolo[3,2-d][1,2,4]triazolo[4,3-a]pyrimidin-5-one;
3-methyl-9-pentyl-8-phenyl-6,9-dihydro-5H-pyrrolo[3,2-d][1,2,4]triazolo[4,3-a]pyrimidin-5-one;
3-methyl-5-oxo-9-pentyl-6,9-dihydro-5H-pyrrolo[3,2-d][1,2,4]triazolo[4,3-a]pyrimidine-8-carbonitrile;
8-(1-benzyl-1H-pyrazol-4-yl)-3-methyl-9-pentyl-6,9-dihydro-5H-pyrrolo[3,2-d][1,2,4]-triazolo[4,3-a]pyrimidin-5-one;
3-methyl-9-pentyl-7-(1-(1-(pyrimidin-2-yl)azetidin-3-yl)-1H-pyrazol-4-yl)-6,9-dihydro-5H-pyrrolo[3,2-d][1,2,4]triazolo[4,3-a]pyrimidin-5-one;
2-(3-(4-(3-Methyl-5-oxo-9-pentyl-6,9-dihydro-5H-pyrrolo[3,2-d][1,2,4]triazolo[4,3-a]pyrimidin-7-yl)-1H-pyrazol-1-yl)azetidin-1-yl)pyrimidine-4-carbonitrile;
7-(1-(1-(4-aminopyrimidin-2-yl)azetidin-3-yl)-1H-pyrazol-4-yl)-3-methyl-9-pentyl-6,9-dihydro-5H-pyrrolo[3,2-d][1,2,4]triazolo[4,3-a]pyrimidin-5-one;
7-(1-(1-(4-(2-hydroxyethylamino)pyrimidin-2-yl)azetidin-3-yl)-1H-pyrazol-4-yl)-3-methyl-9-pentyl-6,9-dihydro-5H-pyrrolo[3,2-d][1,2,4]triazolo[4,3-a]pyrimidin-5-one;
3-methyl-7-(1-(1-(4-(methylamino)pyrimidin-2-yl)azetidin-3-yl)-1H-pyrazol-4-yl)-9-pentyl-6,9-dihydro-5H-pyrrolo[3,2-d][1,2,4]triazolo[4,3-a]pyrimidin-5-one;
9-butyl-3-methyl-7-(1-(1-(pyrimidin-2-yl)azetidin-3-yl)-1H-pyrazol-4-yl)-6,9-dihydro-5H-pyrrolo[3,2-d][1,2,4]triazolo[4,3-a]pyrimidin-5-one;
2-(3-(4-(9-butyl-3-methyl-5-oxo-6,9-dihydro-5H-pyrrolo[3,2-d][1,2,4]triazolo[4,3-a]pyrimidin-7-yl)-1H-pyrazol-1-yl)azetidin-1-yl)pyrimidine-4-carbonitrile;
9-butyl-3-methyl-7-(1-(1-(4-methylpyrimidin-2-yl)azetidin-3-yl)-1H-pyrazol-4-yl)-6,9-dihydro-5H-pyrrolo[3,2-d][1,2,4]triazolo[4,3-a]pyrimidin-5-one;
9-butyl-7-(1-(1-(4-methoxypyrimidin-2-yl)azetidin-3-yl)-1H-pyrazol-4-yl)-3-methyl-6,9-dihydro-5H-pyrrolo[3,2-d][1,2,4]triazolo[4,3-a]pyrimidin-5-one;
7-(1-(1-(4-aminopyrimidin-2-yl)azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one;
7-(1-(1-(4-amino-5-fluoropyrimidin-2-yl)azetidin-3-yl)-1H-pyrazol-4-yl)-9-butyl-3-methyl-6,9-dihydro-5H-pyrrolo[3,2-d][1,2,4]triazolo[4,3-a]pyrimidin-5-one; and
7-(1-(4(2-(2-(dimethylamino)acetyl)-1,2,3,4-tetrahydroisoquinolin-6-yl)methyl)-1H-pyrazol-4-yl)-3-methyl-9-pentyl-6,9-dihydro-5H-pyrrolo[3,2-d][1,2,4]triazolo[4,3-a]pyrimidin-5-one;
or a pharmaceutically acceptable salt of any of the aforementioned.

2. A pharmaceutical composition comprising a compound of claim 1, or a pharmaceutically acceptable salt thereof, and a pharmaceutically acceptable excipient or carrier.

* * * * *